US010421790B2

(12) United States Patent
Shehu et al.

(10) Patent No.: US 10,421,790 B2
(45) Date of Patent: Sep. 24, 2019

(54) FELINE CALICIVIRUS VACCINE

(71) Applicant: Intervet Inc., Madison, NJ (US)

(72) Inventors: Erald Shehu, London (GB); Amrut Shridhar Bhogle, Milton Keynes (GB)

(73) Assignee: Intervet, Inc., Madison, NJ (US)

( * ) Notice: Subject to any disclaimer, the term of this patent is extended or adjusted under 35 U.S.C. 154(b) by 0 days.

(21) Appl. No.: 16/064,650

(22) PCT Filed: Dec. 22, 2016

(86) PCT No.: PCT/EP2016/082330

§ 371 (c)(1),
(2) Date: Jun. 21, 2018

(87) PCT Pub. No.: WO2017/109045

PCT Pub. Date: Jun. 29, 2017

(65) Prior Publication Data

US 2018/0371026 A1 Dec. 27, 2018

(30) Foreign Application Priority Data

Dec. 23, 2015 (EP) .................................... 15202594

(51) Int. Cl.

| | |
|---|---|
| ***A61K 39/00*** | (2006.01) |
| ***C12N 7/00*** | (2006.01) |
| ***C07K 14/005*** | (2006.01) |
| ***A61K 39/12*** | (2006.01) |
| ***C12Q 1/70*** | (2006.01) |
| ***C07K 14/08*** | (2006.01) |
| ***C12N 7/02*** | (2006.01) |
| ***C12N 7/04*** | (2006.01) |

(52) U.S. Cl.

CPC .............. *C07K 14/08* (2013.01); *A61K 39/12* (2013.01); *C12N 7/02* (2013.01); *C12N 7/04* (2013.01); *C12N 2710/16034* (2013.01); *C12N 2770/16021* (2013.01); *C12N 2770/16034* (2013.01); *C12N 2770/16061* (2013.01); *C12N 2770/32022* (2013.01); *C12N 2770/32034* (2013.01)

(58) Field of Classification Search

CPC .............. A61K 39/12; A61K 2039/552; C07K 14/005; C12N 7/00; C12N 2770/16034

See application file for complete search history.

(56) References Cited

U.S. PATENT DOCUMENTS 6,541,458 B1 4/2003 Audonnet et al.

FOREIGN PATENT DOCUMENTS

| | | | |
|---|---|---|---|
| WO | 9101332 | A1 | 2/1991 |
| WO | 0076538 | A1 | 12/2000 |
| WO | 2005080416 | A1 | 9/2005 |
| WO | 2007012944 | A2 | 2/2007 |

OTHER PUBLICATIONS

GenBank AAD47337.1 alignment, Mar. 2019: pdf pag 1.*
Carter, M.J., et al., The Complete Nucleotide Sequence of a Feline Calicivirus, Virology, 1992, pp. 443-448, 190.
Clarke, I.N. and Lambden, P.R., Organization and Expression of Calicivirus Genes, The Journal of Infectious Diseases, 2000, pp. S309-S316, 181 (suppl 2).
Coyne, K.P. et al., Large-Scale Spatial and Temporal Genetic Diversity of Feline Calicivirus, Journal of Virology, Oct. 2012, pp. 11356-11367, vol. 86, No. 20.
European Search report for application 15202594.6, dated May 25, 2016, 6 pages.
Huang, C. et al., A dual-strain feline calicivirus vaccine stimulates broader cross-neutralization antibodies than a single-strain vaccine and lessens clinical signs . . . , Journal of feline Medicine and Surgery, 2010, pp. 12-137, 12.
International Search Report for PCT/EP2016/082330 dated Apr. 7, 2017, 12 pages.
Neill, J.D. et al., Recovery and Altered Neutralization Specificities of Chimeric Viruses Containing Capsid Protein Domain Exchanges from Antigenically Distinct Strains of Feline Calicivirus, Journal of Virology, Feb. 2000, pp. 1079-1084, vol. 74, No. 3.
Oka, T., et al., Complete Genome Sequence of the Feline Calicivirus 2280 Strain from the American Tissue Culture Collection, Genome Announcements, 2013, doi:10.1128/genomeA.00349-13, vol. 1, Issue 3.
Poulet, H. et al., Efficacy of a bivalent inactivated non-adjuvanted feline calicivirus vaccine: Relation between in vitro cross-neutralization and heterologous protection in vivo, Vaccine, 2008, pp. 3647-3654, 26.
Scherk, M.A., et al., 2013 AAFP Feline Vaccination Advisory Panel Report, Journal of Feline Medicine and Surgery, 2013, pp. 785-808, 15.
Yokoyama, N., et al., Further development of a Recombinant Feline Herpesvirus Type 1 Vector Expressing Feline Calicivirus Immunogenic Antigen, J. Vet. Med. Sci., 1998, pp. 717-723, 60(6).

* cited by examiner

*Primary Examiner* — Barry A Chestnut

(57) ABSTRACT

The present invention relates to a new feline capsid protein, to live attenuated feline calicivirus comprising that capsid protein, to live recombinant carrier viruses and live attenuated hybrid feline calicivirus comprising that capsid protein, to vaccines comprising such live attenuated feline caliciviruses, live recombinant carrier viruses and live attenuated hybrid feline calicivirus, and to methods for the preparation of such viruses.

19 Claims, 47 Drawing Sheets

Figure 1:
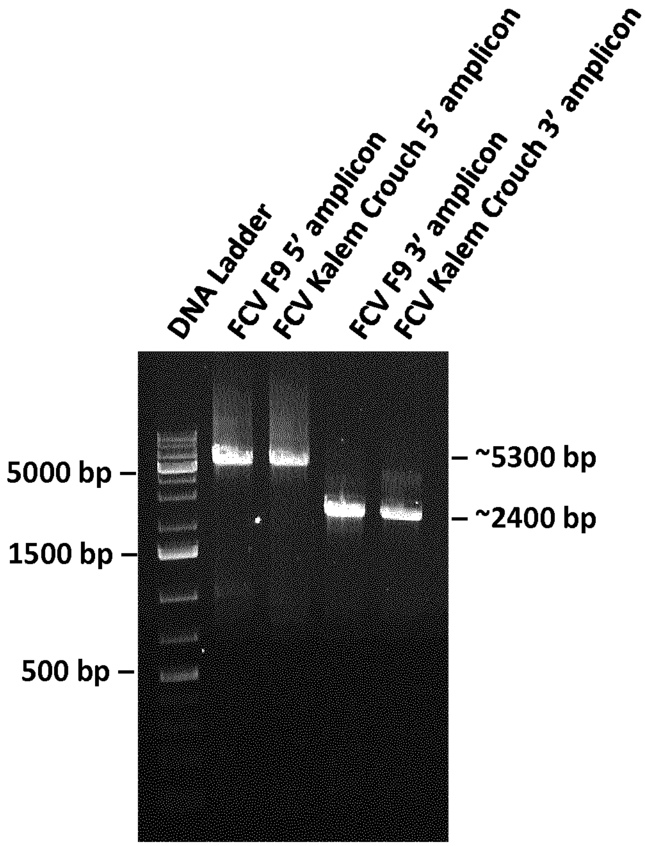

Specification includes a Sequence Listing.

CONTINUED ON FIG.5-2

| | | |
|---|---|---|
| FCV Kalem | 1 | mcstcanvlkyydwdphfklvidpnkflsvgfcdnplmccypellpefgtvwdcdqsplqiyles |
| FCV-F9 | 1 | mcstcanvlkyydwdphfklvinpnnflsvgfcsnplmccypellpefgtvwdcdrspleiyles |
| FCV-UTCVM-NH3 | 1 | mcstcanvlkyydwdphfkliinpnkflsvgfcdnplmccypellpefgtvwncnqsplqiyles |
| FCV-12Q087-5 | 1 | mcstcanvlkyydwdphfrltinpnkflsvgfcdnplmccypellpefgtvwdcnqspleiyles |
| FCV-12Q087-1 | 1 | mcstcanvlkyydwdphfrltinpnkflsvgfcdnplmccypellpefgtvwdcdqspleiyles |
| FCV-1874 | 1 | mcstcanvlkyynwdphfklvinpnkflpigfcdnplmccypellpefgtvwdcdqsplqiyles |
| FCV-2024 | 1 | mcstcanvlkyydwdphirlvidpnrflsvsfcdkpllccypdllpefgtvwdcnqspleiyles |
| FCV-2280 | 1 | mcstcanvlkyygwdphfrlvvnpnkflsvgfcdnplmccypdllpefgtlwdcdqsplqiyles |
| FCV-3786 | 1 | mcstcanvlkyydwdphfrliinpnkflsvgfcdnplmccypellpefgtvwdcdqspleifles |
| FCV-5789 | 1 | mcstcanvlkyydwdphfklvinpnkflpigfcdnpllccypellpefgtvwdcgqsplqiyles |
| FCV-20879 | 1 | mcstcanvlkyydwdphiqlvinpnkflpvgfcdnplmccfpellpefgtvwdcdqsplqiyles |
| FCV-21223 | 1 | mcstcanvlkyydwdphfrliinpnkflsvgfcdnplmccypellpefgtvwdcdqspleiyles |
| FCV-21749 | 1 | mcstcanvlkyydwdphfklvinpnkflavgfcdnplmccypellpefgtvwdcnqsplqiyles |
| FCV-DD-2006-GE | 1 | mcstcanvlkyydwdphfrlvidpnkflsvgfcnnplmccypellpefgtvwdcdqaplqiyles |
| FCV-F4 | 1 | mcstcanvlkyydwdphfrliinpnkflpigfcdnplmccypdllpefgtvwdcdqsplqiyles |
| FCV-F65 | 1 | mcstcanvlkyynwdphiklsinpnkflsvgfcdnplmccypellpefgtmwdcdqsplqiyles |
| FCV-FB-NJ-13 | 1 | mcstcanvlkyygwdphfrltinpndflsvgfcdnplmccypellpefgtvwdcndsplqiyles |
| FCV-GD | 1 | mcstcanvlkyygwdphfdlvinpndflsvgfcdnplmccypellpefgtvwdcndsplqiyles |
| FCV-HRB-SS | 1 | mcstcanvlkyynwdphfkmvvnpnkflsvgfcdkpllccypdllpefgtvwdcnqspleiyles |
| FCV-Urbana | 1 | mcstcanvlkyynwdphfklvinpnkflsigfcdnplmccypellpefgtvwdcdqsplqiyles |
| FCV-USDA | 1 | mcstcanvlkyydwdphirlvidpnrflsvsfcdkpllccypdllpefgtvwdcnqspleiyles |
| FCV-UTCVM-H1 | 1 | mcstcanvlkyydwdphfrlnvnpneflsvgfcdkplmccypellpefgtvwdcsrapleiyles |
| FCV-UTCVM-NH2 | 1 | mcstcanvlkyygwdphfklvinpnnflpvgfcsnplmccypellpefgtvwdcdrspleiyles |
| FCV-UTCVM-H2 | 1 | mcstcanvlkyydwdphirlvinpnkflpigfcdnplmccypellpefgtvwdcdqsplqiyles |
| FCV-UTCVM-NH1 | 1 | mcstcanvlkyydwdphfrlvidpnkflsvgfcdnplmccypellpefgtvwdcdqsplqiyles |

CONTINUED ON FIG.5-3

FIG.5-1

CONTINUED FROM FIG.5-1

```
FCV Kalem        1 ilgddewsstyeaidpvvppmhwdkmgkifqphpgmlmhhiigevakgwdpnlplfrlead-dgs
FCV-F9           1 ilgddewastfdavdpvvppmhwgaagkifqphpgvlmhhligkvaagwdpdlplirlead-dgs
FCV-UTCVM-NH3    1 ilgddewvstyeaidpvvppmhwneagklfqphpgilmhhiigevakawdpnlplfrlead-dgs
FCV-12Q087-5     1 ilgddewastyeaidpvvppmhwdcagkifqphpgvlmhhlisevakgwdpnlpsfrlead-dgs
FCV-12Q087-1     1 ilgddewastyeaidpvvppmhwdcagkifqphpgvlmhhlisevakgwdpnlpsfrlead-dgs
FCV-1874         1 ilgddewsstyeaidpvvppmhwdkagkifqphpgvlmhyiigevakawdpnlplfrlead-dgs
FCV-2024         1 ilgddewsstfeaidpvvppmhwdeagkifqphpgvlmhhlinqvakawdpnlplfrlead-dgs
FCV-2280         1 ilgddewastyeaidpsvppmhwdamgkifqphpgvlmhhiigevakawdpnlplfrlead-dgs
FCV-3786         1 ilgddewastyeaidpvvppmhwdsagkifqphpgvlmhhligevakawdpnlplfrlead-dgs
FCV-5789         1 ilgddewsstyeaidpvvppmhwdeagkifqphpgvlmnyiigevakawdpnlplfrlead-dgs
FCV-20879        1 ilgddewastfeavepsvppmhwdeagkifqphpgvlmhhligevakawdpnlplfrlead-dgs
FCV-21223        1 ilgddewastyeaidpvvppmhwdsagkifqphpgvlmhhligevakawdpnlplfrlead-dgs
FCV-21749        1 ilgddewsstyeaidpvvppmhwdeagkifqphpgvlmhhligevakawdpnlplfrlead-dgs
FCV-DD-2006-GE   1 ilgddewsstfeaidpvvppmhwngagkifqphpgilthhllsevakgwdpnlplfrlegdsdss
FCV-F4           1 ilgddewastheaidpsvppmhwdsagkifqphpgvlmhhligevakawdpnlplfrlead-dgs
FCV-F65          1 ilgddewastyeaidpvvppmhwdemgkifqphpgvlmhhiigevakgwdpnlplfrlead-dgs
FCV-FB-NJ-13     1 ilgddewsstyeaidpvvppmhwdqagkifqphpgvlmhhllgkvakgwdpnlpsfrlesd-dgs
FCV-GD           1 ilgddewsstyeaidpvvppmhwkqagkifqphpghlmhhligkvskgwdpnlpnfrlead-dgs
FCV-HRB-SS       1 ilgddewsstfeaidpvvppmhwddagkifqphpgvlmhhlisevakgwdpnlplfrlead-dgs
FCV-Urbana       1 ilgddewsstyeaidpvvppmhwneagkifqphpgvlmhhiigevakawdpnlplfrlead-dgs
FCV-USDA         1 ilgddewsstfeaidpvvppmhwdeagkifqphpgvlmhhlinqvakawdpnlplfrlead-dgs
FCV-UTCVM-H1     1 ilgddewsstheaidpvvppmhwdeagkifqphpgvlmhhlinkvarawdpnlplfrlead-dgs
FCV-UTCVM-NH2    1 ilgddewastfdavdpvvppmhwsaagkifqphpgvlmhhligkvaagwdpdlplirlead-dgs
FCV-UTCVM-H2     1 ilgddewastydaidpvvppmhwddagkifqphpgvlmhflinevakgwdpslpsfrlead-dgs
FCV-UTCVM-NH1    1 ilgddewastyeaidpsvppmhwdsagkifqphpgvlmhyiigevakawdpnlpnfrlead-dgs
```

CONTINUED ON FIG.5-4

FIG.5-2

CONTINUED FROM FIG.5-1

CONTINUED ON FIG.5-4

| | | |
|---|---|---|
| FCV Kalem | 388 | vttpeqgtmvggviaepsaqmstaadmasgksvdsew-eaffsfhtsvnwstsetqgkilfkqsl |
| FCV-F9 | 388 | itapeqgtmvggviaepsaqmstaadmatgksvdsew-eaffsfhtsvnwstsetqgkilfkqsl |
| FCV-UTCVM-NH3 | 388 | ittpeqgtpvggviaepsaqmsaaadmatgksvdsew-eaffsfhtsvnwstsetqgkilfkqsl |
| FCV-12Q087-5 | 388 | ittpeqgtpvggviaepsaqmstaadmasgksvdsewgkaffsfhtsvnwstsetqgkilfkqsl |
| FCV-12Q087-1 | 388 | ittpeqgtpvggviaepsaqmstaadmasgksvdsewgkaffsfhtsvnwstsetqgkilfkqsl |
| FCV-1874 | 388 | ittpeqgtvvggviaepssqmstaadmasgksvdsew-eaffsfhtsvnwstsetqgkilfkqsl |
| FCV-2024 | 388 | itspeqgtmvggviaepsaqmstaadmatgksvdsew-eaffsfhtsvnwstsetqgkilfkqsl |
| FCV-2280 | 388 | itapeqgtvvggviaepsaqmstaadmatgksvdsew-eaffsfhtsvnwsttetqgkilfkqsl |
| FCV-3786 | 388 | ittpeqgtsvggviaepsaqmstaadmatgktvdsew-eaffsfhtsvnwstsetqgkilfkqsl |
| FCV-5789 | 388 | itapeqgtvvggviaepssqmstaadmasgksvdsew-eaffsfhtsvnwstsetqgkilfkqsl |
| FCV-20879 | 388 | ittpeqgtmvggviaepsaqmstaadmatgksvdsew-eaffsfhtsvnwstsetqgkilfkqsl |
| FCV-21223 | 388 | ittpeqgtsvggviaepsaqmstaadmatgktvdsew-eaffsfhtsvnwstsetqgkilfkqsl |
| FCV-21749 | 388 | ittpeqgtsvggviaepsaqmaaaadmatgksvdsew-eaffsfhtsvnwsttetqgkilfkqsl |
| FCV-DD-2006-GE | 391 | vttpeqgtmvggviaepsaqmstaadmasgksvdsew-eaffsfhtsvnwstsetqgkilfkqsl |
| FCV-F4 | 388 | ittpeqgtavggviaepsaqmstaadmasgksvdsew-eaffsfhtsvnwstsetqgkilfkqsl |
| FCV-F65 | 388 | ittpeqgtmvggviaepsaqmstaadmatgksvdsew-eaffsfhtsvnwstsetqpkilfkqsl |
| FCV-FB-NJ-13 | 388 | ittpeqgtlvggviaepstqmataadmatgktvdsew-eaffsfhtsvnwstsetqgkilfkqnl |
| FCV-GD | 388 | itapeqgtlvggviaepsaqmstaadmatgktvdsew-eaffsfhtsvnwstsetqgkilfkqsl |
| FCV-HRB-SS | 388 | itapeqgtvvggviaepspqmavaadtatgksvdsew-eaffsfhtsvnwstsetqgkilfkqsl |
| FCV-Urbana | 388 | itapeqgtvvggviaepssqmstaadmasgksvdsew-eaffsfhtsvnwstsetqgkilfkqsl |
| FCV-USDA | 388 | itspeqgtmvggviaepsaqmstaadmatgksvdsew-eaffsfhtsvnwstsetqgkilfkqsl |
| FCV-UTCVM-H1 | 388 | ittpeqgtlvggviaepssqmsaaadmatgksvdsew-eaffsfhtsvnwstsetqgkilfkqsl |
| FCV-UTCVM-NH2 | 388 | itapeqgtmvggviaepsaqmstaadmatgksvdsew-eaffsfhtsvnwstsetqgkilfkqsl |
| FCV-UTCVM-H2 | 388 | ittpeqgtavggviaqpsaqmsaaadmasgksvdsew-eeffsfhtsvnwsttetqgkilfkqsl |
| FCV-UTCVM-NH1 | 388 | ittpeqgtmvggviaepsaqmataadtatgksvdsew-eaffsfhtsvnwstsetqgkilfkqsl |

CONTINUED ON FIG.5-5

FIG.5-3

CONTINUED FROM FIG.5-3

CONTINUED FROM FIG.5-2

| | | |
|---|---|---|
| FCV Kalem | 388 | gpllnpylehisklyvawsgsievrfsisgsgvfggklaaivvppgvdpvqstsmlqyphvlfda |
| FCV-F9 | 388 | gpllnpylehlaklyvawsgsievrfsisgsgvfggklaaivvppgvdpvqstsmlqyphvlfda |
| FCV-UTCVM-NH3 | 388 | gpllnpylshlaklyvawsgsievrfsisgsgvfggklaaiivppgiepvqstsmlqyphvlfda |
| FCV-12Q087-5 | 388 | gpllnpylehlaklyvawsgsvevrfsisgsgvfggklaaivvppgvdpvqstsmlqyphvlfda |
| FCV-12Q087-1 | 388 | gpllnpylehlaklyvawsgsvevrfsisgsgvfggklaaivvppgvdpvqstsmlqyphvlfda |
| FCV-1874 | 388 | gpllnpylehlsklyvawsgsvevrfsisgsgvfggklaaivvppgvdpiqstsmlqyphvlfda |
| FCV-2024 | 388 | gpllnpylehlaklyvawsgsvdvrfsisgsgvfggklaaivvppgvnpvqstsmlqyphvlfda |
| FCV-2280 | 388 | gpllnpylehlaklyvawsgsidvrfsisgsgvyggklaaivvppgvdpvqstsmlqyphvlfda |
| FCV-3786 | 388 | gpllnpylthlaklyvawsgsvevrfsisgsgvfggklaaivvppgvdpvqstsmlqyphvlfda |
| FCV-5789 | 388 | gpllnpylehlsklyvawsgsvevrfsisgsgvfggklaaivvppgvdpiqstsmlqyphvlfda |
| FCV-20879 | 388 | gpllnpylthlaklyvawsgsievrfsisgsgvfggklaaivvppgidpvqstsmlqyphvlfda |
| FCV-21223 | 388 | gpllnpylthlaklyvawsgsvevrfsisgsgvfggklaaivvp?gvdpvqstsmlqyphvlfda |
| FCV-21749 | 388 | gpllnpylehlaslyvawsgsievrfsisgsgvfggklaaivvppginpvqstsmlqyphvlfda |
| FCV-DD-2006-GE | 391 | gpllnpylehlaklyvawsgsievrfsisgsgvfggklaaivvppgvnpvqstsmlqyphvlfda |
| FCV-F4 | 388 | gpllnpylehlsklyvawsgsievrfsisgsgvfggklaaivvppgvdpvqstsmlqyphvlfda |
| FCV-F65 | 388 | gpllnpylqhlaklyvawsgsievrfsisgsgvfggklaaivvppgvdpvqstsmlqyphvlfda |
| FCV-FB-NJ-13 | 388 | gpllnpylehiaqlyvawsgsvdvrfsisgsgvfggklaaivvppgvqpvqstsmlqyphvlfda |
| FCV-GD | 388 | gpllnpylghlaqlyvawsgsvdvrfsisgsgvfggklaaivvppgvrpvqstsmlqyphvlfda |
| FCV-HRB-SS | 388 | gpllnpylehlsklyvawsgsvevrfsisgsgvfggklaaivvppgvdpvqstsmlqyphvlfda |
| FCV-Urbana | 388 | gpllnpylehlsklyvawsgsvevrfsisgsgvfggklaaivvppgvdpiqstsmlqyphvlfda |
| FCV-USDA | 388 | gpllnpylehlaklyvawsgsvdvrfsisgsgvfggklaaivvppgvnpvqstsmlqyphvlfda |
| FCV-UTCVM-H1 | 388 | gpllnpylehlsklyvawsgsvevrfsisgsgvfggklaaivvppgvdpvqstsmlqyphvlfda |
| FCV-UTCVM-NH2 | 388 | gpllnpylehlaklyvawsgsievrfsisgsgvfggklaaivvppgvdpvqstsmlqyphvlfda |
| FCV-UTCVM-H2 | 388 | gpllnpylehlsklyvawsgsidvrfsisgsgvfggklaaivvppgvdpvqstsmlqyphvlfda |
| FCV-UTCVM-NH1 | 388 | gpllnpylthlaklyvawsgsievrfsisgsgvfggklaaivvppgidpvqstsmlqyphvlfda |

CONTINUED ON FIG.5-6

FIG.5-4

CONTINUED FROM FIG.5-3

CONTINUED ON FIG.5-6

```
FCV Kalem       775 rqvepvifsipdlrnslyhlmsdtdttslvimvyndlinpyandsnssgcivtvetkpgidfkfh
FCV-F9          775 rqvepvifclpdlrstlyhlmsdtdttslvimvyndlinpyandanssgcivtvetkpgpdfkfh
FCV-UTCVM-NH3   775 rqvepviftipdlrsnlyhlmsdtdttslvimiyndlinpyandsnssgcivtvetkpgadfkfh
FCV-12Q087-5    778 rqvepviftipdlrnslyhlmsdtdttslvimvyndlinpyasdsnssgcivtvetkpgpdfkfh
FCV-12Q087-1    778 rqvepviftipdlrnslyhlmsdtdttslvimvyndlinpyasdsnssgcivtvetkpgpdfkfh
FCV-1874        775 rqvepviftipdlrstlyhlmsdtdttslvvmvyndlinpyandsnssgcivtvetkpgsdfkfh
FCV-2024        775 rqvepvifsipdlrstlyhlmsdtdttslvimvyndlinpyasdsnssgcivtvetkpgpdfkfh
FCV-2280        775 rqvepvifsipdlrstlyhlisdtdttslvimvyndlinpyasdtnssgcivtvetkpgpdfkfh
FCV-3786        775 rqvepviftipdlrstlyhlmsdtdttslvimvyndlinpyandtnssgcivtvetkpgpdfkfh
FCV-5789        775 rqvepviftipdlrsnlyhlmsdtdttslvimvyndlinpyandsnssgcivtvetkpgpdfkfh
FCV-20879       775 rqvdpviftipdlrstlyhlmsdtdttslvimvyndlinpyasdsnssgcivtvetkpgpdfkfh
FCV-21223       775 rqvepviftipdlrstlyhlmsdtdttslvimvyndlinpyandtnssgcivtvetkpgpdfkfh
FCV-21749       775 rqvepvifsipdlrnslyhlmsdtdttslvimvyndlinpyandtnssgcivtvetkpgpdfkfh
FCV-DD-2006-GE  778 rqvepvifsipdlrstlyhlmsdtdttslvimvyndlinpyandtnssgcivtvetkpgpdfrfh
FCV-F4          775 rqvepviftipdlrstlyhvmsdtdttslvimvyndlinpyandsnssgcivtvetkpgpdfkfh
FCV-F65         775 rqvdpviftipdlrstlyhlmsdtdttplvimvyndlinpyandsnssgcivtvetkpgpdfkfh
FCV-FB-NJ-13    775 rqvepvifsipdlrsnlyhlmsdtdttslvimvyndlinpyandsnssgciitvetkpgpdfkfh
FCV-GD          775 rqvepvifsipdlrsslyhlmsdtdttslvimvyndlinpyagdsnssgciitvetkpgadfkfh
FCV-HRB-SS      775 rqvepviftlpdlrnslyhlmsdtdttslvimvyndlinpyandsnssgcvvtvetkpgadfkfh
FCV-Urbana      775 rqvepviftipdlrstlyhlmsdtdttslvimvyndlinpyandsnssgcivtvetkpgsdfkfh
FCV-USDA        775 rqvepvifsipdlrstlyhlmsdtdttslvimvyndlinpyasdsnssgcivtvetkpgpdfkfh
FCV-UTCVM-H1    775 rqvdpviftipdlrsnlyhlmsdtdttslvimvyndlinpyandsnssgcivtvetkpgpdfkfh
FCV-UTCVM-NH2   775 rqvepvifsipdlrstlyhlmsdtdttslvimvyndlinpyandanssgcivtvetkpgpdfkfh
FCV-UTCVM-H2    775 rqvepvifslpdlrnslyhlisdtdttslvimvyndlinpyaneanssgcivtvetkpgpdfkfh
FCV-UTCVM-NH1   775 rqvepviftipdlrstlyhlmsdtdttslvimvyndlinpyandsnssgciltvetkpgpdfkfh
```

CONTINUED ON FIG.5-7

FIG.5-5

CONTINUED FROM FIG.5-5

CONTINUED FROM FIG.5-4

| | | |
|---|---|---|
| FCV Kalem | 775 | llkppgsmlthgsipsdlipksssl wignrhwtditdfvirpfvfqanrhfdfnqetagwstprf |
| FCV-F9 | 775 | llkppgsmlthgsipsdlipktssl wignrywsditdfvirpfvfqanrhfdfnqetagwstprf |
| FCV-UTCVM-NH3 | 775 | llkppgsmlthgsipsdlipksssl wignrhwtditefvvrpfvfqanrhfdfnqetagwstprf |
| FCV-12Q087-5 | 778 | llkppgsmlthgsvpsdlipksssl wignrywsditdfvirpfvfqanrhfdfnqetagwstprf |
| FCV-12Q087-1 | 778 | llkppgsmlthgsvpsdlipksssl wigiclwrgitdfvirpfvfqvnrhfdfnqetagwstprf |
| FCV-1874 | 775 | llkppgsvlthgsvpsdliprtssl wignrfwtditdfvirpfvfqanrhfdfnqetagwstprf |
| FCV-2024 | 775 | llkppgsmlthgsvpsdlipksssl wignrhwtditdfvirpfvfqanrhfdfnqetagwstprf |
| FCV-2280 | 775 | llkppgsmlthgsipadlipksssl wignrywsditefvvrpfvfqanrhfdfnqetagwstprf |
| FCV-3786 | 775 | llkppgsmlthgsvpsdlipksssl wignrywsditdfvirpfvfqanrhfdfnqetagwstprf |
| FCV-5789 | 775 | llkppgsmlthgsvpsdliprtssl wvgnrfwgditdfvirpfvfqanrhfdfnqetagwstpqf |
| FCV-20879 | 775 | llkppgsmlthgsvpsdlipksssl wignrhwtditdfvirpfvfqanrhfdfnqetagwstprf |
| FCV-21223 | 775 | llkppgsmlthgsvpsdlipksssl wignrywsditdfvirpfvfqanrhfdfnqetagwstprf |
| FCV-21749 | 775 | llkppgsmlthgsipsdlipksssl wignrywsditdfiirpfvfqanrhfdfnqetagwstprf |
| FCV-DD-2006-GE | 778 | llkppgsmlthgsvpsdlipksssl wignrhwtditdfvirpfvfqanrhfdfnqetagwstprf |
| FCV-F4 | 775 | llkppgsvlthgsipsdlipksssl wignrywtditdfvirpfvfqanrhfdfnqetagwstprf |
| FCV-F65 | 775 | llkppgsmlthgsvpsdlipksssl wignrhwtditdfvirpfvfqanrhfdfnqetagwstpry |
| FCV-FB-NJ-13 | 775 | llkppgsmlvhgsipsnlipksssl wignrhwsditdfvirpsvfqanrhfdfkqetagwstprf |
| FCV-GD | 775 | llkppgsvlthgsvpsdlipktssl wignrhwaditdfvirpsvfqanrhfdfkqetagwstprf |
| FCV-HRB-SS | 775 | llkppgsmlthgsvpsdliprsssl wignrywtditdfvirpfvfqanrhfdfnqetagwstprf |
| FCV-Urbana | 775 | llkppgsmlthgsvpsdlipktssl wignrfwsditdfvirpfvfqanrhfdfnqetagwstprf |
| FCV-USDA | 775 | llkppgsmlthgsvpsdlipksssl wignrhwtditdfvirpfvfqanrhfdfnqetagwstprf |
| FCV-UTCVM-H1 | 775 | llkppgsmlthgsvpsdlipksssl wignrhwtditdfvirpfvfqanrhfdfnqetagwstprf |
| FCV-UTCVM-NH2 | 775 | llkppgsmlthgsvpsdlipktssl wignrywsditdfvirpfvfqanrhfdfnqetagwstprf |
| FCV-UTCVM-H2 | 775 | llkppgsmlthgsipsdliprsssl wignrhwtditdfvirpfvfqanrhfdfnqetagwstprf |
| FCV-UTCVM-NH1 | 775 | llkppgsmlthgsvpsdlipksssl wignrywsdindfvirpfvfqanrhfdfnqetagwstprf |

CONTINUED ON FIG.5-8

FIG.5-6

CONTINUED FROM FIG.5-5

CONTINUED ON FIG.5-8

```
FCV Kalem     1165 rplavtvsqskgaklgngiatdyivpgipdgwpdttiptkltptgdyaitssdgndietkleyen
FCV-F9        1165 rpisvtiteqngaklgigvatdyivpgipdgwpdttipgelipagdyaitngtgndittatgydt
FCV-UTCVM-NH3 1165 rpitvtvsekggsklgigvatdsivpgipdgwpdtsisdtlipsgdyaitsgngndiitgadyds
FCV-12Q087-5  1168 rpltitisveggaklgtgvatdyivpgipdgwpdttipekltpagdyaitdgngsdivtaakydt
FCV-12Q087-1  1168 rpltitisvkeganselgvatdyivpgipdgwpdttipekltpagdyaitdssgsdittaakyda
FCV-1874      1165 rpitvtisekdgaklgigvatdfivpgipdgwpdttigerlvpvgdyaitnsagidittasqydt
FCV-2024      1165 rpititisekdgsklgigvamdsivpgipdgwpdttipeklvpagnyaiangtgndittakdyds
FCV-2280      1165 rpitvtvsesggsklgigvatdyivpgipdgwpdttipekltpagnyaittsnnsdiatateydh
FCV-3786      1165 rpititisvkesaklgtgvatdyivpgipdgwpdttipeeltpagdyaitnssgndittaagfda
FCV-5789      1165 rpitvtisvkngeklgigiatdfivpgipdgwpdttigeelvpagdyaittssgndittaqqyda
FCV-20879     1165 rpititisvnnaaklgtgvatdyivpgipdgwpdttipseltpagdyaitnssgndittavgydt
FCV-21223     1165 rpititisvkelaklgtgvatdyivpgipdgwpdttipeeltpagdyaitnssgndittaadfda
FCV-21749     1165 rpitvtisqkegeklgigvatdyivpgipdgwpdttipgkltpvgnyaitdesgsdivtaaefds
FCV-DD-2006-GE1168 rpltvtisqkdgdklgtgvatdyivpgipdgwpdttipgelipagdyaittgngtdittaqvfds
FCV-F4        1165 rpititisekngsklgigvatdyiipgipdgwpdttiadklipagdysittgegndiktaqaydt
FCV-F65       1165 rpitvsisqqegaklgigvaidyivpgipdgwprstipsklvpaggyaitakngndittaaqyda
FCV-FB-NJ-13  1165 rpmtitisqkqsaklgiavalesivpgipdgwpdttidsnlipagdyaitnqadndittameyda
FCV-GD        1165 rpmtvtisqsggaklgigiahetivpgipdgwpdttipgelvpageyaivnqtsndiatavdydt
FCV-HRB-SS    1165 rpititisekngeklgigvatdyivpgipdgwpdttiaekltpagdyaittgdgndiitanaydt
FCV-Urbana    1165 rpitvtisekngaklgvgvatdfivpgipdgwpdttigeklvpagdyaitngsgndittanqyda
FCV-USDA      1165 rpititisekdgsklgigvamdsivpgipdgwpdttipeklvpagdyaiangtgndittakdyds
FCV-UTCVM-H1  1165 rplsvtisqsggaklgigiatdyivpgipdgwpdttipgeltpagdyaivnqnnsdiatkqayes
FCV-UTCVM-NH2 1165 rpisvtisqqdgaklgigvatdyivpgipdgwpdttipgelipagdyaitnnigddittatgydt
FCV-UTCVM-H2  1165 rpitinisqkegarlgtaiavdtilpgipdgwpdttiptvltpagkyaitsgnnsdiltrndyen
FCV-UTCVM-NH1 1165 rpitvtisvkesaklgigvatdyivpgipdgwpdttiptdltpagdyaitdstgndittpsgyds
```

CONTINUED ON FIG.5-9

FIG.5-7

CONTINUED FROM FIG.5-7

CONTINUED FROM FIG.5-6

| | | |
|---|---|---|
| FCV Kalem | 1165 | advikknntnfrsmyicgslqrawgdkkisntgfittgvi---s---dnsispsntidqskivvyq |
| FCV-F9 | 1165 | adiiknntnfrgmyicgslqrawgdkkisntafittatldgdn---nnkinpcntidqskivvfq |
| FCV-UTCVM-NH3 | 1165 | advikknntnfrsmyicgslqrawgdkkvsetafittavr---n---ensispsnvidatklivyq |
| FCV-12Q087-5 | 1168 | advikknntnfkgmyicgslqrawgdkkisntafittgtv---e---nnsiepsntidatklavfq |
| FCV-12Q087-1 | 1168 | advienntnfkgmyicgslqrawgdkkisntafittgtv---e---dnfiepsntidatklavfq |
| FCV-1874 | 1165 | agviknntnfrgmyicgslqrawgdkkisntafittatv---n---rndlipsnvidqtkiaifq |
| FCV-2024 | 1165 | atviqnntnfkgmyicgslqrawgdkkisntafittatr---s---dntitpsnvidptkiavyq |
| FCV-2280 | 1165 | adeiknntnfksmyicgslqrawgdkkisntafittavk---e---gnsitpsntidmtklvvyq |
| FCV-3786 | 1165 | adviknntnfrgmyicgslqrawgdkkisntafittgtv---e---ggkirpsnvidqtkiavfq |
| FCV-5789 | 1165 | adiinnntnfksmyicgslqrawgdkkisntafittatv---s---gnklipsnvidqtkiaifq |
| FCV-20879 | 1165 | adeiknntnfrgmyicgslqrawgdkkisntafittgiv---t---gnklqpsntidqtkiavfq |
| FCV-21223 | 1165 | admiknntnfrgmyicgslqrawgdkkisntafittgtv---e---ggkirpsnvidqtkiavfq |
| FCV-21749 | 1165 | atgiknntefrgmyicgslqrawgdkkisntafittakv---n---nnmlepsnvidqtkiaifq |
| FCV-DD-2006-GE | 1168 | adviqnntnfrgmyicgslqrawgdkkisntafittaiv---k---ggklrpsnvidqtkiaifq |
| FCV-F4 | 1165 | aavvknttnfrgmyicgslqrawgdkkisntafittair---d---gneikpsntidmtklavyq |
| FCV-F65 | 1165 | ageivnntnfksmyicgalqrawgdkkvsntafvttatv---t---gntlkpsntidntkiaiyq |
| FCV-FB-NJ-13 | 1165 | ateiknntnfrsmyicgalqrawgdkkvsntafittadl---d---gntikpnnvinqsriivyq |
| FCV-GD | 1165 | ataitnntnfksmyicgalqrawgdkkisntafittadl---n---gnkikpnnvinqqrivifq |
| FCV-HRB-SS | 1165 | advvknntnfrgmyicgslqrawgdkkisntafittgtv---s---dnkikpsnvidptklavfq |
| FCV-Urbana | 1165 | adiirnntnfkgmyicgslqrawgdkkisntafittatv---e---gndlipsnvidqtkiaifq |
| FCV-USDA | 1165 | atviqnntnfkgmyicgslqrawgdkkisntafittatr---s---dntitpsnvidptkiavyq |
| FCV-UTCVM-H1 | 1165 | atsienntnfksmyicgslhrawgdkkisntafittatv---d---gnnlipsntigqdkiavfq |
| FCV-UTCVM-NH2 | 1165 | adiiknntnfkgmyicgslqrawgdkkisntafittatl---sgnnnnkinpcntidqskivvfq |
| FCV-UTCVM-H2 | 1165 | adviknntnfrsmyicgslqrawgdkdisntafittgtv---n---gnniepsntidptklavfq |
| FCV-UTCVM-NH1 | 1165 | aisivnntnfrgmyicgslqrawgdkkvsntafittgiv---t---gnklepsntidqtkiaifq |

CONTINUED ON FIG.5-10

FIG.5-8

CONTINUED FROM FIG.5-7

CONTINUED ON FIG.5-10

| | | |
|---|---|---|
| FCV Kalem | 1537 | dnhvnsevqtsditlailgytgigeeaiganrdsvvrisvlpetgarggnhpifyknsmklgyvi |
| FCV-F9 | 1546 | dnhvgkkaqtsddtlallgytgigeqaigsdrdrvvristlpetgarggnhpifyknsiklgyvi |
| FCV-UTCVM-NH3 | 1537 | dahvetdvqtsdvtlailgytgigeeaigldrdkvvrisilpetgtrggnhpifyknsiklgyvi |
| FCV-12Q087-5 | 1540 | dthvghevqtsddtlallgytgigeqaigsdrdrvvrisvlpetgarggnhpifyknsiklgyvi |
| FCV-12Q087-1 | 1540 | dthvgrevqtsddtlallgytgigeqaigsdrdrvvrisvlpetgarggnhpifyknsiklgyvv |
| FCV-1874 | 1537 | dnhvgvdvqtsddtlallgytgigeeaigadrervvristlpetgarggnhpifyknsiklgyvv |
| FCV-2024 | 1537 | dthvgaevqtsddtlailgytgigeeaigadrdrvvrisvlpetgarggnhpifyknsiklgyvi |
| FCV-2280 | 1537 | dahvgndvqtsdvtlallgytgigeqaigsdrdrvvrisvlpetgarggnhpifykntiklgyvi |
| FCV-3786 | 1537 | dthanrevqtsddtlallgytgigeeaigadrdrvvrisvlpetgarggnhpifyknsiklgyvi |
| FCV-5789 | 1537 | dthanqgvqtsddtlailgytgigeeaiganrervvristlpeagarggnhpifykntmklgyvi |
| FCV-20879 | 1537 | dthankdpqtsddtlallgytgigeeaigadrdrvvrisvlpeagarggnhpifyknsiklgyvi |
| FCV-21223 | 1537 | dthvnqevqtsddtlallgytgigeeaigadrdrvvrisvlpetgarggnhpifyknsiklgyvi |
| FCV-21749 | 1537 | dnhvgrdvqtsddtlallgytgigeqaigsdrdrvvrisilpeagarggnhpifyknsiklgyvl |
| FCV-DD-2006-GE | 1540 | dnhvqagiqtsddtlavlgytgigeqaigadrdrvvrisvlpetgarggnhpifyknsiklgyvi |
| FCV-F4 | 1537 | dthvgqevqtsddtlallgytgigeeaigsnrdrvvrisvlpeagarggnhpifyknsiklgyvi |
| FCV-F65 | 1537 | dnhvnsdvqtsdvtlsllgytgigeeavgadrdklvrisvlpetgarggnhpifyknsiklgyvi |
| FCV-FB-NJ-13 | 1537 | dnhvnlqvqtsevtlamlgytgigeeviganrdrvvrinvlpevsarggnhpiyyknslklgyvi |
| FCV-GD | 1537 | dnhvgseaqtsdvtlamlgytgigeevigadrdrvvrinvlpevsarggnhpifykntlklgyvi |
| FCV-HRB-SS | 1537 | dnhvgadaqtsddtlallgytgigehaigadrervvristlpetgarggnhpifyknsiklgyvi |
| FCV-Urbana | 1537 | dnhvqdevqtsddtlallgytgigeeaiganrervvristlpetgarggnhpifyknsiklgyvi |
| FCV-USDA | 1537 | dthvgaevqtsddtlailgytgigeeaigadrdrvvrisvlpetgarggnhpifyknsiklgyvi |
| FCV-UTCVM-H1 | 1537 | dnhvnaevqtsdvtlatlgytgigeeaigairdrvvrisvlpetgarggnhpifyknamklgyvi |
| FCV-UTCVM-NH2 | 1546 | dnhvgkevqtsddtlallgytgigeqaigsdrdrvvristlpetgarggnhpifyknsiklgyvi |
| FCV-UTCVM-H2 | 1537 | dnhvksevqtsdvtlsvlgytgigeeavgadrdkvvrisvlpetgarggnhpifyknsmklgyvi |
| FCV-UTCVM-NH1 | 1537 | dthanrdtqisddtlallgytgigeeaigadrdrvvrisvlpetgarggnhpifyknsiklgyvi |

CONTINUED ON FIG.5-11

FIG.5-9

CONTINUED FROM FIG.5-9

CONTINUED FROM FIG.5-8

| | | |
|---|---|---|
| FCV Kalem | 1537 | ssidvfnsqilhtsrqlslnnyllppdsfavyriidsngswfdigidsdgfsfvgvssfpklefp |
| FCV-F9 | 1546 | rsidvfnsqilhtsrqlslnhyllppdsfavyriidsngswfdigidsdgfsfvgvsgfgklefp |
| FCV-UTCVM-NH3 | 1537 | rsidvmnsqilhtsrqlslnnyslppdsfavyriidsagswfdigidsdgfsfvgisnvgklifp |
| FCV-12Q087-5 | 1540 | rsidvfnsqilhtsrqlslnhyllppdsfavyriidsngswfdigidsdgfsfvgvssitklefp |
| FCV-12Q087-1 | 1540 | rsidvfnsqilhtsrqlslnhyllppdsfavyriidsngswfdigidsdgfsfvgvssitklefp |
| FCV-1874 | 1537 | rsidvfnsqilhtsrqlslnnyllppdsfavyriidsngswfdigidtdgfsfvgvsnigklefp |
| FCV-2024 | 1537 | rsidvfnsqilhtsrqlslnnyllppdsfavyritdsngswfdigidsdgfsfvgasnvgklefp |
| FCV-2280 | 1537 | rsidvfnsqilhtsrqlslnhyllppdsfavyriidsngswfdigidsdgfsfvgvsslptlefp |
| FCV-3786 | 1537 | rsidvfnsqilhtsrqlslnhyllspdslavyritdsngswfdigidsdgfsfvgvsnigklefp |
| FCV-5789 | 1537 | rsidvfnsqilhtsrqlslnnyllppdsfavyritdsngswfdigidtdgfsfvgvssignlefp |
| FCV-20879 | 1537 | rsidvfnsqilhtsrqlslnhyllspdsfavyriidsngswfdigidsegfsfvgvssigklefp |
| FCV-21223 | 1537 | rsidvfnsqilhtsrqlslnhyllspdslavyritdsngswfdigidsdgfsfvgvsnigklefp |
| FCV-21749 | 1537 | rsidvfnsqilhtsrqlslnhyllspdsfavyriidsngswfdigidsdgfsfvgvsaigkleyp |
| FCV-DD-2006-GE | 1540 | rsidvfnsqilhtsrqlslnhyllppdsfavyriidsngswfdigidsdgfsfvgvsnigklefp |
| FCV-F4 | 1537 | rsidvfnsqilhtsrqlslnhyllppdsfavyriidsngswfdigidsegfsfvgvsdigklefp |
| FCV-F65 | 1537 | rsidvfnsqilhtsrqlslnnyllppdsfavyriidangswfdigidsdgfsfvgvsnigklefp |
| FCV-FB-NJ-13 | 1537 | rsidvfnsqilhtsrqlalnnylldpdcfavyritdsngswfdigidysgfsfvgvsnigalefp |
| FCV-GD | 1537 | rsidvfnsqilhtsrqlalnnylldpdsfavyritdsngswfdigidysgfsfvgvsnigelefp |
| FCV-HRB-SS | 1537 | rsidvfnsqilhtsrqlslnhyllppdsfavyriidsngswfdigidsdgfsfvgvtnigklefp |
| FCV-Urbana | 1537 | rsidvfnsqilhtsrqlslnhyllppdsfavyriidsngswfdvgidfdgfsfvgvsdvgklefp |
| FCV-USDA | 1537 | rsidvfnsqilhtsrqlslnnyllppdsfavyritdsngswfdigidsdgfsfvgasnvgklefp |
| FCV-UTCVM-H1 | 1537 | gdidvfnsqilhtsrqlslnnyllppdsfavyriidsngswfdvgidsdgfsfvgvssipklefp |
| FCV-UTCVM-NH2 | 1546 | rsidvfnsqilhtsrqlslnhyllppdsfavyriidsngswfdigidsdgfsfvgvsgfgklefp |
| FCV-UTCVM-H2 | 1537 | ssidvfnsqilhtsrqlslnhyllppdsfavyritdsngswfdigidndgfsfvgvshigklefp |
| FCV-UTCVM-NH1 | 1537 | rsidvfnsqilhtsrqlslnhyllspdsfavyritdsngswfdigidsdgfsfvgvnnigklefp |

FIG.5-10

CONTINUED FROM FIG.5-9

| | | |
|---|---|---|
| FCV Kalem | 1927 | lsasymgiqlakirlasnirssmtkl* |
| FCV-F9 | 1936 | lsasymgiqlakirlasnirspmtkl* |
| FCV-UTCVM-NH3 | 1927 | lsasymgiqlakirlasnirsamtkl* |
| FCV-12Q087-5 | 1930 | ltasymgiqlakirlasnirgqmtki* |
| FCV-12Q087-1 | 1930 | ltasymgiqlakirlasnirsqmtki* |
| FCV-1874 | 1927 | ltasymgiqlakirlasnirstmikl* |
| FCV-2024 | 1927 | ltasymgiqlakirlasnirssmtkl* |
| FCV-2280 | 1927 | lsasymgiqlakirlasnirssmtkl* |
| FCV-3786 | 1927 | ltasymgiqlakvrlasnirssmtkl* |
| FCV-5789 | 1927 | lsasymgiqlakirlasnirstmtkl* |
| FCV-20879 | 1927 | ltasymgiqlakirlasnirstltkl* |
| FCV-21223 | 1927 | ltasymgiqlakvrlasnirssmtkl* |
| FCV-21749 | 1927 | ltasymgiqlakvrlasnirssmtkl* |
| FCV-DD-2006-GE | 1930 | lsasymgiqlakirlasnirssmtkl* |
| FCV-F4 | 1927 | lsasymgiqlakirlasnirsrmtkl* |
| FCV-F65 | 1927 | lsasymgiqlakirlasnirstmtkl* |
| FCV-FB-NJ-13 | 1927 | ltasytgiqlakirlasnirssmtkl* |
| FCV-GD | 1927 | ltasymgvqlakirlasnirssmtkl* |
| FCV-HRB-SS | 1927 | lsasymgiqlakirlasnirssmikl* |
| FCV-Urbana | 1927 | ltasymgiqlakirlasnirstmtkl* |
| FCV-USDA | 1927 | ltasymgiqlakirlasnirssmtkl* |
| FCV-UTCVM-H1 | 1927 | lsasymgiqlakirlasnirstmtkl* |
| FCV-UTCVM-NH2 | 1936 | lsasymgiqlakirlasnirspmtkl* |
| FCV-UTCVM-H2 | 1927 | lsasymgiqlakirlasnirssmikl* |
| FCV-UTCVM-NH1 | 1927 | ltasymgiqlakirlasnirstmtkl* |

FIG.5-11

```
FCV-F9         1 gtaaaagaaatttgagacaatgtctcaaactctgagcttcgtgcttaaaactcacagtgt
FCV-Kalem      1 gtaaaagaaatttgagacaatgtctcaaactctgagcttcgtgcttaaaactcacagcgt
FCV-FK         1 gtaaaagaaatttgagacaatgtctcaaactctgagcttcgtgcttaaaactcacagtgt
FCV-KF         1 gtaaaagaaatttgagacaatgtctcaaactctgagcttcgtgcttaaaactcacagcgt

FCV-F9       121 tatttataacaagctctcacgcactatacgtgctgaggcttgcccttcttgtgctagtta
FCV-Kalem    121 tttctataacaagctctctcgttctatgcgagctgaagcttgtccttcttgtgccagtta
FCV-FK       121 tatttataacaagctctcacgcactatacgtgctgaggcttgcccttcttgtgctagtta
FCV-KF       121 tttctataacaagctctctcgttctatgcgagctgaagcttgtccttcttgtgccagtta

FCV-F9       241 gattccatcatgggaggatgtcacaaagtcttcaacctactctctcctgctctctgagga
FCV-Kalem    241 gatgccatcatgggaggatgtcacaaaaacctctacttactctcttctactctccgaaga
FCV-FK       241 gattccatcatgggaggatgtcacaaagtcttcaacctactctctcctgctctctgagga
FCV-KF       241 gatgccatcatgggaggatgtcacaaaaacctctacttactctcttctactctccgaaga

FCV-F9       361 gctatccactcagtcccacccggctaatgctgaaatgtgcaaagaacagctcactttctt
FCV-Kalem    361 gctttccactcagtctcatccggccaatgttgacatgtgcaaagaacagctcacgtcatt
FCV-FK       361 gctatccactcagtcccacccggccaatgctgaaatgtgcaaagaacagctcacttcctt
FCV-KF       361 gctttccactcagtctcatccggccaatgttgacatgtgcaaagaacagctcacgtcatt

FCV-F9       481 acaacacacggctgcacggttggaatggagggagaaattcttctctaaacctcttgactt
FCV-Kalem    481 acaacaccagacggctcgcattgaatggagggaaaagttcttctctaagccccttaactt
FCV-FK       481 acaacacacggctgcacggttggaatggagggagaaattcttctctaaacctcttgactt
FCV-KF       481 acaacaccagacggctcgcattgaatggagggaaaagttcttctctaagccccttaactt

FCV-F9       601 tatcttggaaaaagcatgctattgtaaatcctatggagagcagtggttcactgctgccaa
FCV-Kalem    601 catcttggagaaagcttgctactgcaaatcctatggtgaagagtggttcgatgctgcaaa
FCV-FK       601 tatcttggaaaaagcatgctattgtaaatcctatggagagcagtggttcactgctgccaa
FCV-KF       601 catcttggagaaagcttgctactgcaaatcctatggtgaagagtggttcgatgctgcaaa
```

```
FCV-F9         1 ccgaaaggactttgtgcactctgtcaagttaacacttgcacggaggcgcgatcttcagta
FCV-Kalem      1 ccgcaaggactttgtgcactccgtcaagctaacgcttgcacggaggcgcgatcttcagta
FCV-FK         1 ccgaaaggactttgtgcactctgtcaagttaacacttgcacggaggcgcgatcttcagta
FCV-KF         1 ccgcaaggactttgtgcactccgtcaagctaacgcttgcacggaggcgcgatcttcagta

FCV-F9       121 cgacgtatgtcctaactgcacctctggtgacgtcccggatgacgggtcttcgacaatgtc
FCV-Kalem    121 tgatgtatgtcctaactgcacttctagtgatatccctgatgatggttcatcaacaacgtt
FCV-FK       121 cgacgtatgtcctaactgcacctctggtgacgtcccggatgacgggtcttcgacaatgtc
FCV-KF       121 tgatgtatgtcctaactgcacttctagtgatatccctgatgatggttcatcaacaacgtt

FCV-F9       241 cacctccgacgagttatgccctgaggacttggttaatgtggctgctcatatccgtaaggc
FCV-Kalem    241 tacttctgacgagttgtctcctgacgaattggttcacgttgctgctcacattcgcaaggc
FCV-FK       241 cacctccgacgagttatgccctgaggacttggttaatgtggctgctcatatccgtaaggc
FCV-KF       241 tacttctgacgagttgtctcctgacgaattggttcacgttgctgctcacattcgcaaggc

FCV-F9       361 attagtcatggctgaggcgatgctgccccaacgatcccgagcgtcaatcccactgcacca
FCV-Kalem    361 attggtgatggctgaagctatgctgcctcaacggtcacgagcaacaatcccacttcatca
FCV-FK       361 attagtcatggctgaggcgatgctgccccaacgatcccgagcgtcaatcccactgcacca
FCV-KF       361 attggtgatggctgaagctatgctgcctcaacggtcacgagcaacaatcccacttcatca

FCV-F9       481 tctccttgaaagagttggtgtgtcaaaagatattctccaaactactgcgatttggaaaat
FCV-Kalem    481 cattcttgaaaagattggtgtttctaaagatattcttcaggttactgccctttggaaaat
FCV-FK       481 tctccttgaaagagttggtgtgtcaaaagatattctccaaactactgcgatttggaaaat
FCV-KF       481 cattcttgaaaagattggtgtttctaaagatattcttcaggttactgccctttggaaaat

FCV-F9       601 acaaaagttaagggaaatgaaaaactttgagagtgatacgctaaaacctcttattggtgg
FCV-Kalem    601 gaacaaactaagggagatgagaagcttcgaaagcaacacactcaaaccactggttggagc
FCV-FK       601 gcaaaagttaagggaaatgaaaaactttgagagtgatacgctaaaacctcttattggtgg
FCV-KF       601 gaacaaactaagggagatgagaagcttcgaaagcaacacactcaaaccactggttggagc
```

CONTINUED FROM FIG.6-1

CONTINUED ON FIG.6-4

FIG.6-2

CONTINUED FROM FIG.6-1

CONTINUED ON FIG.6-4

| | | |
|---|---|---|
| FCV-F9 | 721 | atttatagatggtctacggttcttgaccgtggacaacccaaacccgatgggtttcctccc |
| FCV-Kalem | 721 | tttcattgacggcttaaggtttatgactgtggataaccccaaccctatggcattcttacc |
| FCV-FK | 721 | atttatagatggtctacggttcttgaccgtggacaacccaaacccgatgggtttcctccc |
| FCV-KF | 721 | tttcattgacggcttaaggtttatgactgtggataaccccaaccctatggcattcttacc |
| | | |
| FCV-F9 | 841 | cacaatatctggctggatcatcacattaaccgcaataatggagctatacaacatcaccga |
| FCV-Kalem | 841 | cacactatcaggatggatcattaccctcactgcaattatggagttatacaacatcacaga |
| FCV-FK | 841 | cacaatatctggctggatcatcacattaaccgcaataatggagctatacaacatcaccga |
| FCV-KF | 841 | cacactatcaggatggatcattaccctcactgcaattatggagttatacaacatcacaga |
| | | |
| FCV-F9 | 961 | aaccaaatttacagttgtgttaaggcgctgttcactggatttagatctgaggacgtagc |
| FCV-Kalem | 961 | ccctaaattctacagtcagatcaaagcactgttcacgggatttaggacagaggatgtggc |
| FCV-FK | 961 | aaccaaatttacagttgtgttaaggcgctgttcactggatttagatctgaggacgtagc |
| FCV-KF | 961 | ccctaaattctacagtcagatcaaagcactgttcacgggatttaggacagaggatgtggc |
| | | |
| FCV-F9 | 1081 | aaacaacggcagattttcaaagataaaagcttgcctggccggagcgacaactcttgtatc |
| FCV-Kalem | 1081 | aaacaatgggaggttttcaaagattaaaacctgcctgtctggtgcaacgaccctggtatc |
| FCV-FK | 1081 | aaacaatggcagattttcaaagataaaagcttgcctggccggagcgacaactcttgtatc |
| FCV-KF | 1081 | aaacaatgggaggttttcaaagattaaaacctgcctgtctggtgcaacgaccctggtatc |
| | | |
| FCV-F9 | 1201 | tgttaatgagttgtcagcaagaactgttgccctatcagagctaaacaatccaacaacaac |
| FCV-Kalem | 1201 | tgttaacgaattatctgcaaggacagtggctatttctgaattgaataacccaactactac |
| FCV-FK | 1201 | tgttaatgagttgtcagcaagaactgttgccctatcagagctaaacaatccaacaacaac |
| FCV-KF | 1201 | tgttaacgaattatctgcaaggacagtggctatttctgaattgaataacccaactactac |
| | | |
| FCV-F9 | 1321 | caagattcatactctaaaccccatcatgcaatcatacaatccaatcttgagaaatttaat |
| FCV-Kalem | 1321 | caaagttcacactctgaatccaattatgcaatcatacaacccaattcttagaaatttaat |
| FCV-FK | 1321 | caagattcatactctaaaccccatcatgcaatcatacaatccaatcttgagaaatttaat |
| FCV-KF | 1321 | caaagttcacactctgaatccaattatgcaatcatacaacccaattcttagaaatttaat |

FIG.6-3

CONTINUED ON FIG.6-5

CONTINUED FROM FIG.6-3

CONTINUED FROM FIG.6-2

```
FCV-F9       721  aaaactcatagggcttgtaaaacccctgaatttggcgatgattattgataatcatgaaaa
FCV-Kalem    721  caagctaattgggcttatcaaacccctcaatttggcaatgataatcgacaatcatgaaaa
FCV-FK       721  aaaactcatagggcttgtaaaacccctgaatttggcgatgattattgataatcatgaaaa
FCV-KF       721  caagctaattgggcttatcaaacccctcaatttggcaatgataatcgacaatcatgaaaa

FCV-F9       841  atgcaccatagatattataacatcagtcattacggctttctatgataaaattggcaaggc
FCV-Kalem    841  atgcacaattgacataatcacttcactggtaacagcattctatgacaaaattgctaaagc
FCV-FK       841  atgcaccatagatattataacatcagtcattacggctttctatgataaaattggcaaggc
FCV-KF       841  atgcacaattgacataatcacttcactggtaacagcattctatgacaaaattgctaaagc

FCV-F9       961  gaattcctttggtacatggcagcagcgattctatgttacctgatcactgggttaatccc
FCV-Kalem    961  taattcattttggtatatggctgctgcaattctatgttacctgattacgggtataatccc
FCV-FK       961  gaattcctttggtacatggcagcagcgattctatgttacctgatcactgggttaatccc
FCV-KF       961  taattcattttggtatatggctgctgcaattctatgttacctgattacgggtataatccc

FCV-F9      1081  aggtatagttgccacacaaaagctagctgcaatgttcgcaacatggaactctgagtccat
FCV-Kalem   1081  gggtataattgccacacagaaacttgcagcaatgttcgctacatggaactctgaatccat
FCV-FK      1081  aggtatagttgccacacaaaagctagctgcaatgttcgcaacatggaactctgagtccat
FCV-KF      1081  gggtataattgccacacagaaacttgcagcaatgttcgctacatggaactctgaatccat

FCV-F9      1201  gtctgacacggattcggtagaacgactgctagaattggctaagatcttgcatgaggagat
FCV-Kalem   1201  ctctgacactgactctgttgagcggttgctcgaattggctaagatcttgcacgaggagat
FCV-FK      1201  gtctgacacggattcggtagaacgactgctagaattggctaagatcttgcatgaggagat
FCV-KF      1201  ctctgacactgactctgttgagcggttgctcgaattggctaagatcttgcacgaggagat

FCV-F9      1321  gtcaaccttggacggtgttataacatcatgcaacaagaggaaagctattgctcggaagag
FCV-Kalem   1321  gtccacactagacggtgttgtcacctcatgcaacaagagaagagcaattgccaaaaagag
FCV-FK      1321  gtcaaccttggacggtgttataacatcatgcaacaagaggaaagctattgctcggaagag
FCV-KF      1321  gtccacactagacggtgttgtcacctcatgcaacaagagaagagcaattgccaaaaagag
```

FIG.6-4

CONTINUED ON FIG.6-6

CONTINUED FROM FIG.6-3

CONTINUED ON FIG.6-6

```
FCV-F9      1441 acaggtgccagtttgttacatattaactggcccacctggatgtgggaaaacaaccgcagc
FCV-Kalem   1441 gcaagtcccagtttgctacatccttactggaccacctggatgtggcaagaccactgcggc
FCV-FK      1441 acaggtgccagtttgttacatattaactggcccacctggatgtgggaagacaaccgcagc
FCV-KF      1441 gcaagtcccagtttgctacatccttactggaccacctggatgtggcaagaccactgcggc

FCV-F9      1561 tcatcatgacacatatactggaaatgaggtatgtatcattgatgagtttgattcgtctga
FCV-Kalem   1561 tcatcatgatacttacactggcaatgaagtgtgcattgttgatgagtttgattcatcaga
FCV-FK      1561 tcatcatgacacatatactggaaatgaggtatgtatcattgatgagtttgattcgtctga
FCV-KF      1561 tcatcatgatacttacactggcaatgaagtgtgcattgttgatgagtttgattcatcaga

FCV-F9      1681 ttgtgacatgcttgagaacaagggaaagctcttcacctcaaagtatataattatgacttc
FCV-Kalem   1681 ttgtgatatgcttgaaaataagggaaagctctttacctctaagtacataataatgacttc
FCV-FK      1681 ttgtgacatgcttgagaacaagggaaagctcttcacctcaaagtatataattatgacttc
FCV-KF      1681 ttgtgatatgcttgaaaataagggaaagctctttacctctaagtacataataatgacttc

FCV-F9      1801 tactatcatcgatgtaactaacccttttgtggagtcgcacaagcgtgcaaggcctgggac
FCV-Kalem   1801 tacaatcattgacgttgcaaaccctttggtggaatctcacaagcgcgcgcgccctggaac
FCV-FK      1801 tactatcatcgatgtaactaaccctttggtggagtcgcacaagcgtgcaaggcctgggac
FCV-KF      1801 tacaatcattgacgttgcaaaccctttggtggaatctcacaagcgcgcgcgccctggaac

FCV-F9      1921 ggccgagtgctggtgcaaggaatacgttcttgaccctaaggggcttcaacaccaaagcat
FCV-Kalem   1921 ggctgagtgctggtgcaaggagtatgttttggaccccaagggacttcagcatcagagtat
FCV-FK      1921 ggccgagtgctggtgcaaggaatacgttcttgaccctaaggggcttcaacaccaaagcat
FCV-KF      1921 ggctgagtgctggtgcaaggagtatgttttggaccccaagggacttcagcatcagagtat

FCV-F9      2041 cttcttgctcaagaacatggctttgaggctgaagatgggtgcgcagaacatcgatatgg
FCV-Kalem   2041 cttcattcttaagaacatggcatttgaggcagagaatggctctagtgagcacaggtttgg
FCV-FK      2041 cttcttgctcaagaacatggctttgaggctgaagatgggtgcgcagaacatcgatatgg
FCV-KF      2041 cttcattcttaagaacatggcatttgaggcagagaatggctctagtgagcacaggtttgg
```

FIG.6-5

CONTINUED ON FIG.6-7

CONTINUED FROM FIG.6-5

CONTINUED FROM FIG.6-4

```
FCV-F9      1441 tcaagcattagctaagaaattgtctgatcaagagccgtcggtaattaaccttgatgttga
FCV-Kalem   1441 cctagcccttgcaaagaagctctctgatcaagagccatcagtgattaatttggatgttga
FCV-FK      1441 tcaagcattagctaagaaattgtctgatcaagagccgtcggtaattaaccttgatgttga
FCV-KF      1441 cctagcccttgcaaagaagctctctgatcaagagccatcagtgattaatttggatgttga

FCV-F9      1561 caaggtagactatgcaaattttgtgattgggatggtaaactctgctcctatggtgttaaa
FCV-Kalem   1561 caaagtggactatgcaaattttgtgattggtatggttaattcggcaccaatggttctaaa
FCV-FK      1561 caaggtagactatgcaaattttgtgattgggatggtaaactctgctcctatggtgttaaa
FCV-KF      1561 caaagtggactatgcaaattttgtgattggtatggttaattcggcaccaatggttctaaa

FCV-F9      1681 caactctgaaactccagtgaaaccctcttccaagcgcgcaggtgcattctaccgaagggt
FCV-Kalem   1681 taactctgaaacccctgtaaaaccctcttctaagcgtgcaggtgctttctaccgaagagt
FCV-FK      1681 caactctgaaactccagtgaaaccctcttccaagcgcgcaggtgcattctaccgaagggt
FCV-KF      1681 taactctgaaacccctgtaaaaccctcttctaagcgtgcaggtgctttctaccgaagagt

FCV-F9      1801 gtctgttcctcgtagctgctataagaaaaacttctcccatctctcacttgctaaacgagg
FCV-Kalem   1801 atctgtccctcgaagctgctacaagaagaactttcacacctttcacttgctaaacgagg
FCV-FK      1801 gtctgttcctcgtagctgctataagaaaaacttctcccatctctcacttgctaaacgagg
FCV-KF      1801 atctgtccctcgaagctgctacaagaagaactttcacacctttcacttgctaaacgagg

FCV-F9      1921 gaaggctccccctcctacctttcttaacattgactctttagctcagacgatgaagcaaga
FCV-Kalem   1921 caaggctcctcctcccactttcttaacattgattcccttgcccaaactatgaaacaaga
FCV-FK      1921 gaaggctccccctcctacctttcttaacattgactctttagctcagacgatgaagcaaga
FCV-KF      1921 caaggctcctcctcccactttcttaacattgattcccttgcccaaactatgaaacaaga

FCV-F9      2041 gtttgtgtgtcaacaggaagaggttgaaactgttcgcaggctcctcaacgcggttagggc
FCV-Kalem   2041 ctttgtctgtcagcagagtgaggtcgacactgttcgcaggctgcttaatgcaataagggc
FCV-FK      2041 gtttgtgtgtcaacaggaagaggttgaaactgttcgcaggctcctcaacgcggttagggc
FCV-KF      2041 ctttgtctgtcagcagagtgaggtcgacactgttcgcaggctgcttaatgcaataagggc
```

FIG.6-6

CONTINUED ON FIG.6-8

CONTINUED FROM FIG.6-5

CONTINUED ON FIG.6-8

```
FCV-F9      2161 aaggatgaatgctaccttcactgtgtgtgttggacccgagacctcgcactcgattggttg
FCV-Kalem   2161 acggcttaacgcgacattcactgtgtgcgttgggcctgagtcctcaaattccattgggtg
FCV-FK      2161 aaggatgaatgctaccttcactgtgtgtgttggacccgagacctcgcactcgattggttg
FCV-KF      2161 acggcttaacgcgacattcactgtgtgcgttgggcctgagtcctcaaattccattgggtg

FCV-F9      2281 atgtaacgaagcatcactttctgcccttgaaggtaactgtgtaaagtcagctttgggcgt
FCV-Kalem   2281 atgcaacgaagcctcccttgcagcactagaaggaaattgcgtgcagactgcgttgggcgt
FCV-FK      2281 atgtaacgaagcatcactttctgcccttgaaggtaactgtgtaaagtcagctttgggcgt
FCV-KF      2281 atgcaacgaagcctcccttgcagcactagaaggaaattgcgtgcagactgcgttgggcgt

FCV-F9      2401 tgacagtgttaggttggatgaactacccgccaatcagcatgtggtaaccgttaattcggt
FCV-Kalem   2401 tgatagtgtcaggctggacgaactacccgccaatcaacatgtggtaaccgtgaattcggt
FCV-FK      2401 tgacagtgttaggttggatgaactacccgccaatcagcatgtggtaaccgttaattcggt
FCV-KF      2401 tgatagtgtcaggctggacgaactacccgccaatcaacatgtggtaaccgtgaattcggt

FCV-F9      2521 cagagccgcatatgatgtgcttactgtccccgacaagatccctgcaatgttgcgtcactg
FCV-Kalem   2521 cagagccgcatatgatgtgctaactgtccccgacaaaattccagctatgttaaggcactg
FCV-FK      2521 cagagccgcatatgatgtgcttactgtccccgacaagatccctgcaatgttgcgtcactg
FCV-KF      2521 cagagccgcatatgatgtgctaactgtccccgacaaaattccagctatgttaaggcactg

FCV-F9      2641 catagtcatcctggagtcttgcggtggtgcacgcatctgggctttaggtcgcaacgtgat
FCV-Kalem   2641 tattgtcatcttggaatcatgtggtggagcacgtatctgggctttgggtcacaatgtgat
FCV-FK      2641 catagtcatcctggagtcttgcggtggtgcacgcatctgggctttaggtcacaacgtgat
FCV-KF      2641 tattgtcatcttggaatcatgtggtggagcacgtatctgggctttgggtcacaatgtgat

FCV-F9      2761 tgcgccaaccatgccatggtccgagatctttcgtgagctcttctctctcttaggtagaat
FCV-Kalem   2761 tgccccttctatgccatggtctgaactctttcgagaacttttctctttattgggtaggat
FCV-FK      2761 tgccccaaccatgccatggtccgagatctttcgtgagctcttctctctcttaggtagaat
FCV-KF      2761 tgccccttctatgccatggtctgaactctttcgagaacttttctctttattgggtaggat
```

FIG.6-7

CONTINUED ON FIG.6-9

CONTINUED FROM FIG.6-7

CONTINUED FROM FIG.6-6

```
FCV-F9      2161 cactgcgcacgtgttaactcccaatgagacctttaatggaaagaagtttgttgtgtcacg
FCV-Kalem   2161 tactgctcatgtcctcactcccgatgagcctttcaatgggaagaggtttgttgtatctcg
FCV-FK      2161 cactgcgcacgtgttaactcccaatgagacctttaatggaaagaagtttgttgtgtcacg
FCV-KF      2161 tactgctcatgtcctcactcccgatgagcctttcaatgggaagaggtttgttgtatctcg

FCV-F9      2281 gtgtatgtcagataaggatctcactcatttatgccacttcattaaagggaaaattgtcaa
FCV-Kalem   2281 atgcatgtccaacaaggatttaacccacctgtgccatttcataagagggaagattgtcaa
FCV-FK      2281 gtgtatgtcagataaggatctcactcatttatgccacttcattaaagggaaaattgtcaa
FCV-KF      2281 atgcatgtccaacaaggatttaacccacctgtgccatttcataagagggaagattgtcaa

FCV-F9      2401 gtttgatttggcctgggctgttcgtcgtcatctcacactggcagggcagtttcaagctat
FCV-Kalem   2401 atttgatttggcctgggctcttcgccgtcacctcacactatctggacagtttcaagcaat
FCV-FK      2401 gtttgatttggcctgggctcttcgtcgtcatctcacactggcagggcagtttcaagctat
FCV-KF      2401 atttgatttggcctgggctcttcgccgtcacctcacactatctggacagtttcaagcaat

FCV-F9      2521 gatggatgagacctccttttctgatgaccacgttgtaacacaatttgtaacacctggtgg
FCV-Kalem   2521 gatggatgaaacatccttttcggatgagcatgtagtcacacagtttgtaacgccaggtgg
FCV-FK      2521 gatggatgagacctccttttctgatgaccacgttgtgacacaatttgtaacacctggtgg
FCV-KF      2521 gatggatgaaacatccttttcggatgagcatgtagtcacacagtttgtaacgccaggtgg

FCV-F9      2641 ccgagcaggaggtgtcaccgcaaccccaaccggaggatgtgttaggttaatgggattatc
FCV-Kalem   2641 ccgcgctggaggtatcactgcaacaccaactggtggttgtgtcagattaatgggtctctc
FCV-FK      2641 ccgagcaggaggtgtcaccgcaaccccaaccggaggatgtgttaggttaatgggattgtc
FCV-KF      2641 ccgcgctggaggtatcactgcaacaccaactggtggttgtgtcagattaatgggtctctc

FCV-F9      2761 ttggtcatctgtcaaagtatcagccctagtactaactgctcttggaatgtacgcatctag
FCV-Kalem   2761 atggtctagtgttaaagtctccactcttgttctgaccgctcttggaatgtacgcatctag
FCV-FK      2761 ttggtcatctgtcaaagtatcagccctagtactaactgctcttggaatgtacgcatctag
FCV-KF      2761 atggtctagtgttaaagtctccactcttgttctgaccgctcttggaatgtacgcatctag
```

FIG.6-8

CONTINUED ON FIG.6-10

CONTINUED FROM FIG.6-7

CONTINUED ON FIG.6-10

```
FCV-F9      2881 atttagaccaaaatcggaagcaaaaggaaaaaccaaattgaagattgggacatacagggg
FCV-Kalem   2881 atttagacccaaatcagaagctaagggaaaaacaaaatccaaggttgggccctacagagg
FCV-FK      2881 atttagaccaaaatcggaagcaaaaggaaaaaccaaattgaagattggaacatacagggg
FCV-KF      2881 atttagacccaaatcagaagctaagggaaaaacaaaatccaaggttgggccctacagagg

FCV-F9      3001 aaaattggatttgtcagtggaggatttcttaatgttgcgccatcgtgccgctctaggagc
FCV-Kalem   3001 aaaattggacttatcagtagaagattttctgatgctgcgccatcgtgcagcacttggtgc
FCV-FK      3001 aaaattggatttgtcagtggaggatttcttaatgttgcgccatcgtgccgctctaggagc
FCV-KF      3001 aaaattggacttatcagtagaagattttctgatgctgcgccatcgtgcagcacttggtgc

FCV-F9      3121 tgattatgaggatgtcaccgtaattggcaaaggtggcgtcaaacatgaaaagatcagaac
FCV-Kalem   3121 tgattttgaagatgtcaccgtgattggaaaaggtggtgttaaacatgaaagaatcagaac
FCV-FK      3121 tgattatgaggatgtcaccgtaattggcaaaggtggcgtcaaacatgaaaagatcagaac
FCV-KF      3121 tgattttgaagatgtcaccgtgattggaaaaggtggtgttaaacatgaaagaatcagaac

FCV-F9      3241 aggcaccaagttccacaagaatgcaattggatctgtcacagatgtttgtggggagcacaa
FCV-Kalem   3241 cggcacaaaattccacaaaaacgccattggatctgtaactgatgtttgtggtgagcacaa
FCV-FK      3241 aggcaccaagttccacaagaatgcaattggatctgtcacagatgtttgtggggagcacaa
FCV-KF      3241 cggcacaaaattccacaaaaacgccattggatctgtaactgatgtttgtggtgagcacaa

FCV-F9      3361 ggattcatttttcttgggtgaaaggattttgatcttaagactaatggtgaattttgctg
FCV-Kalem   3361 tgattcattctttcttggtgagagaatatttgacctcaaaactaatggtgagttttgctg
FCV-FK      3361 ggattcatttttcttgggtgaaaggattttgatcttaagactaatggtgaattttgctg
FCV-KF      3361 tgattcattctttcttggtgagagaatatttgacctcaaaactaatggtgagttttgctg

FCV-F9      3481 tgatccgtggggatcccccgtggcaactgagtggaagcctaaaatgtacacaacaacctc
FCV-Kalem   3481 tgacccgtggggctcacctgttgccacagaatggaagccaaaaccatacaccactacatc
FCV-FK      3481 tgatccgtggggatcccccgtggcaactgagtggaagcctaaaatgtacacaacaacctc
FCV-KF      3481 tgacccgtggggctcacctgttgccacagaatggaagccaaaaccatacaccactacatc
```

FIG.6-9

CONTINUED ON FIG.6-11

CONTINUED FROM FIG.6-9

CONTINUED FROM FIG.6-8

```
FCV-F9      2881 tcgcggtgtagcgctgactgatgacgagtacgatgagtggcgcgaacacaacgcctccag
FCV-Kalem   2881 tcgtggtgtagcgctcactgatgatgagtacgatgaatggagggaacacaacgccacacg
FCV-FK      2881 tcgcggtgtagcgctgactgatgacgagtacgatgagtggcgcgaacacaacgcctccag
FCV-KF      2881 tcgtggtgtagcgctcactgatgatgagtacgatgaatggagggaacacaacgccacacg

FCV-F9      3001 cgacgacaatgatgcagtaaaattccggtcgtggtggaactccagaaccaaaatggccaa
FCV-Kalem   3001 tgatgatgcagatgcagttaaatttagatcatggtggaactcaagatcaaaattggcgga
FCV-FK      3001 cgacgacaatgatgcagtaaaattccggtcgtggtggaactccagaaccaaaatggccaa
FCV-KF      3001 tgatgatgcagatgcagttaaatttagatcatggtggaactcaagatcaaaattggcgga

FCV-F9      3121 caataccctaaaagctgtggatcgtggttatgacgtcagctttgctgaggaatcaggacc
FCV-Kalem   3121 aaacaatctcagagctgtggagcgtggatatgacgttagctttgctgaagaatcaggacc
FCV-FK      3121 caataccctaaaagctgtggatcgtggttatgacgtcagctttgctgaggaatcaggacc
FCV-KF      3121 aaacaatctcagagctgtggagcgtggatatgacgttagctttgctgaagaatcaggacc

FCV-F9      3241 aggctattgcatccacatgggccacggtgtttacgcatccgtagctcacgtggtgaaagg
FCV-Kalem   3241 gggatactgtgtccatatgggtcatggggtgtacgcctcagtagcccatgtggtgaaagg
FCV-FK      3241 aggctattgcatccacatgggccacggtgtttacgcatccgtagctcacgtggtgaaagg
FCV-KF      3241 gggatactgtgtccatatgggtcatggggtgtacgcctcagtagcccatgtggtgaaagg

FCV-F9      3361 ctttcgcagcacgaaaattctacctagtgctgcacctttcttttctgggaagcccactcg
FCV-Kalem   3361 ctttcgcagtacaaagatcttgcccagtgctgcgcctttcttctcaggcaaacccacccg
FCV-FK      3361 ctttcgcagcacgaagattctacctagtgctgcacctttcttttctgggaagcccactcg
FCV-KF      3361 ctttcgcagtacaaagatcttgcccagtgctgcgcctttcttctcaggcaaacccacccg

FCV-F9      3481 tggaaagattctggggtgctttgcaacaacttcaactgaaactcacccgggagactgtgg
FCV-Kalem   3481 agggaagattatagggtgttttgctacaacttcaactgaaacccacccaggtgattgtgg
FCV-FK      3481 tggaaagattctggggtgctttgcaacaacttcaactgaaactcacccgggagactgtgg
FCV-KF      3481 agggaagattatagggtgttttgctacaacttcaactgaaacccacccaggtgattgtgg
```

FIG.6-10

CONTINUED ON FIG.6-12

CONTINUED FROM FIG.6-9

CONTINUED ON FIG.6-12

```
FCV-F9     3601 cctcccatatattgatgacaacgggagggtgaccggcctccacactggctctggggacc
FCV-Kalem  3601 tctaccttacatcgatgacaatggtagagtcactggactgcacacaggatccggtggacc
FCV-FK     3601 cctcccatatattgatgacaacgggagggtgaccggcctccacactggctctggggacc
FCV-KF     3601 tctaccttacatcgatgacaatggtagagtcactggactgcacacaggatccggtggacc

FCV-F9     3721 cgtcactgctcaaaagtatgacgtaacaaagcctgatataagttacaaaggcttaatttg
FCV-Kalem  3721 tgttactgcccaaaagtatgacattacaaagcctgatattagttacaaaggattgatttg
FCV-FK     3721 cgtcactgctcaaaagtatgacgtaacaaagcctgatataagttacaaaggcttaatttg
FCV-KF     3721 tgttactgcccaaaagtatgacattacaaagcctgatattagttacaaaggattgatttg

FCV-F9     3841 ccacactgaggattatcaagaatgctcacaccaacccgcatcacttggaagcggggatcc
FCV-Kalem  3841 ccacacagatgattatgaggaatgttcgcaccaaccagcatcactaggtagtggtgatcc
FCV-FK     3841 ccacactgaggattatcaagaatgctcacaccaacccgcatcacttggaagcggggatcc
FCV-KF     3841 ccacacagatgattatgaggaatgttcgcaccaaccagcatcactaggtagtggtgatcc

FCV-F9     3961 cgttgagggtcctccacatgatgttttgcacagagttcaaaagatgcttatcgaccacct
FCV-Kalem  3961 ggttgagggcccccccatgatgttttgcatagggttcagaaaatgctaattgatcacct
FCV-FK     3961 ggttgagggtcctccacatgatgttttgcacagagttcaaaagatgcttatcgaccacct
FCV-KF     3961 ggttgagggcccccccatgatgttttgcatagggttcagaaaatgctaattgatcacct

FCV-F9     4081 actcaatcatgatacttcctctggaccatacttgggtggcagaaagaaagatcacatggc
FCV-Kalem  4081 actcaatcatgatacatcctctggcccatacttaggtggaagaaagaaagatcatatggt
FCV-FK     4081 actcaatcatgatacttcctctggaccatacttgggtggcagaaagaaagatcacatggc
FCV-KF     4081 actcaatcatgatacatcctctggcccatacttaggtggaagaaagaaagatcatatggt

FCV-F9     4201 ccaaggcatagcactaccacatgagtacacaattgggctaaaggacgagttaaggcccgt
FCV-Kalem  4201 tcaagggattgctctccctcatgagtacacaattgggctaaaagatgaattgagaccaat
FCV-FK     4201 ccaaggcatagcactaccacatgagtacacaattgggctaaaggacgagttaaggcccgt
FCV-KF     4201 tcaagggattgctctccctcatgagtacacaattgggctaaaagatgaattgagaccaat
```

FIG.6-11

CONTINUED ON FIG.6-13

CONTINUED FROM FIG.6-11

CONTINUED FROM FIG.6-10

```
FCV-F9      3601 caaaaccccaagtgccaagttggtggtgccatatgtgcatattgacatgaagactaaatc
FCV-Kalem   3601 caaaactcccagcgcaaaattggttgtcccctatgtccatattgatatgaaaacaaaatc
FCV-FK      3601 caaaaccccaagtgccaagttggtggtgccatatgtgcatattgacatgaagactaaatc
FCV-KF      3601 caaaactcccagcgcaaaattggttgtcccctatgtccatattgatatgaaaacaaaatc

FCV-F9      3721 taagcaattggatgagattaggattataccaaaaggcacacgtctccatgtctccccagc
FCV-Kalem   3721 caaacaattggatgaaattcggataataccaaaaggaacacgcctccacgtttctcctgc
FCV-FK      3721 taagcaattggatgagattaggattataccaaaaggcacacgtctccatgtctccccagc
FCV-KF      3721 caaacaattggatgaaattcggataataccaaaaggaacacgcctccacgtttctcctgc

FCV-F9      3841 ccgctgtccaaaatctctcactgctatagttgttgattctctaaaaccatactgtgagaa
FCV-Kalem   3841 acgatgtccaaaatcccttactgctattgtagttgactccttaaaaccctactgtgataa
FCV-FK      3841 ccgctgtccaaaatctctcactgctatagttgttgattctctaaaaccatactgtgagaa
FCV-KF      3841 acgatgtccaaaatcccttactgctattgtagttgactccttaaaaccctactgtgataa

FCV-F9      3961 ttcaggctttgtccctatgaacatttcctcggaaacctctatgctctcagctttccacaa
FCV-Kalem   3961 ctctggctttgttcctatgaatatctcttctgaaaactcaatgctctctgcatttcacaa
FCV-FK      3961 ttcaggctttgtccctatgaacatttcctcggaaacctctatgctctcagctttccacaa
FCV-KF      3961 ctctggctttgttcctatgaatatctcttctgaaaactcaatgctctctgcatttcacaa

FCV-F9      4081 taacggtgagccggacaagcagttattggatctcctgtctgcaaaatggaaattggcaac
FCV-Kalem   4081 aaatggtgagcctgacaaggcactgttggatttgctatcttcaaaatggaaacttgccac
FCV-FK      4081 taacggtgagccggacaagcagttattggatctcctgtctgcaaaatggaaattggccac
FCV-KF      4081 aaatggtgagcctgacaaggcactgttggatttgctatcttcaaaatggaaacttgccac

FCV-F9      4201 ggagaaggttagtgaagggaagagaaggatgatttggggttgtgatgttggcgtcgctac
FCV-Kalem   4201 tgagaaagttcaggaaggaaagagaaggatgatctggggttgtgatgttggggttgccac
FCV-FK      4201 ggagaaggttagtgaagggaagagaaggatgatttggggttgtgatgttggcgtcgctac
FCV-KF      4201 tgagaaagttcaggaaggaaagagaaggatgatctggggttgtgatgttggggttgccac
```

FIG.6-12

CONTINUED ON FIG.6-14

CONTINUED FROM FIG.6-11

CONTINUED ON FIG.6-14

```
FCV-F9      4321 tgtctgtgcagctgcgttcaagggtgttagcgatgccatcacagcaaaccaccagtacgg
FCV-Kalem   4321 agtttgcgctgctgcatttaaaggtgttagtgacgcaataacggcaaaccaccagtatgg
FCV-FK      4321 tgtctgtgcagctgcgttcaagggtgttagcgatgccatcacagcaaaccaccagtacgg
FCV-KF      4321 agtttgcgctgctgcatttaaaggtgttagtgacgcaataacggcaaaccaccagtatgg

FCV-F9      4441 caaaagcgcggccaaggtatttgcggtcgattattccaaatgggattcgacccaatcgcc
FCV-Kalem   4441 caagagcgctgccaaggtttttgcggtcgattactccaagtgggattcgactcaatcgcc
FCV-FK      4441 caaaagcgcggccaaggtatttgcggtcgattattccaaatgggattcgacccaatcgcc
FCV-KF      4441 caagagcgctgccaaggtttttgcggtcgattactccaagtgggattcgactcaatcgcc

FCV-F9      4561 tgactcagcctctaacacactgaagagccctcctgttgcaatctttaatggtgttgctgt
FCV-Kalem   4561 tgattcagctgcaaacaccttaaaaagtcctccaatagcggtgttcaatggtgttgcagt
FCV-FK      4561 tgactcagcctctaacacactgaagagccctcctgttgcaatctttaatggtgttgctgt
FCV-KF      4561 tgattcagctgcaaacaccttaaaaagtcctccaatagcggtgttcaatggtgttgcagt

FCV-F9      4681 tcattgtctgtatgttgggtgtgccattcttcaatccctagaagctaaggccattcccgt
FCV-Kalem   4681 tcactgcctatatgttggttgtgctatccttcaatctctggaatccaaaaacatacctgt
FCV-FK      4681 tcattgtctgtatgttgggtgtgccattcttcaatccctagaagctaaggccattcccgt
FCV-KF      4681 tcactgcctatatgttggttgtgctatccttcaatctctggaatccaaaaacatacctgt

FCV-F9      4801 gtttcctattatgtatgcaagtattagtgaccaaatttttggaaatctttcttcctatgg
FCV-Kalem   4801 gttccctatcatgtttgctagtgttagtgatcaaatctttggaaaccttactgcttatgg
FCV-FK      4801 gtttcctattatgtatgcaagtattagtgaccaaatttttggaaatctttcgtcctatga
FCV-KF      4801 gttccctatcatgtttgctagtgttagtgatcaaatctttggaaaccttactgcttatgg

FCV-F9      4921 tgttgttttcttgaagagaacaatcacaaggacacctcaggggataaggggtttacttga
FCV-Kalem   4921 tgttgttttcctaaaaagaaccatccaaaggacccctagtggcattcgaggtcttcttga
FCV-FK      4921 tgttgttttcttgaagagaacaatcacaaggacacctcaggggataaggggtttacttga
FCV-KF      4921 tgttgttttcctaaaaagaaccatccaaaggacccctagtggcattcgaggtcttcttga
```

FIG.6-13

CONTINUED ON FIG.6-15

CONTINUED FROM FIG.6-13

CONTINUED FROM FIG.6-12

```
FCV-F9      4321 gcctatacaggttggtatcaacatggatagccccagcgtcgaagcgctgttccaaaggat
FCV-Kalem   4321 acctgttcaagttgggattaacatggatagccccagtgttgaggcactttaccaacgaat
FCV-FK      4321 gcctatacaggttggtatcaacatggatagccccagcgtcgaagcgctgttccaaaggat
FCV-KF      4321 acctgttcaagttgggattaacatggatagccccagtgttgaggcactttaccaacgaat

FCV-F9      4441 tcgtgtcagtgcagcttcaattgacatccttcgttacttttccgatcgctctccaattgt
FCV-Kalem   4441 tcgggttagtgctgcctcaattgatattcttagatacttctctgatagatctccaattgt
FCV-FK      4441 tcgtgtcagtgcagcttcaattgacatccttcgttacttctctgatcgctctccaattgt
FCV-KF      4441 tcgggttagtgctgcctcaattgatattcttagatacttctctgatagatctccaattgt

FCV-F9      4561 aaaagtgtcctctggcttaccatctggaatgcctcttacctcagtaatcaattcccttaa
FCV-Kalem   4561 aaaggtttcgtctggtcttccatctggtatgcctctgacttctgtaattaactctttaaa
FCV-FK      4561 aaaagtgtcctctggcttaccatctggaatgcctcttacctcagtaatcaattcccttaa
FCV-KF      4561 aaaggtttcgtctggtcttccatctggtatgcctctgacttctgtaattaactctttaaa

FCV-F9      4681 cacttggaacctttctcaactttgatatcatgacttacggggatgatggtgtctacat
FCV-Kalem   4681 cacttggaatctgttctcctcatttgacatgatgacttacggtgatgatggtgttacat
FCV-FK      4681 cacttggaacctttctcaactttgatatcatgacttacggggatgatggtgtctacat
FCV-KF      4681 cacttggaatctgttctcctcatttgacatgatgacttacggtgatgatggtgttacat

FCV-F9      4801 cctgaaaccaactcgggttgacaagtccgttggagcaattgagcctattgatcctgactc
FCV-Kalem   4801 cttaaaacccacaagggtcgacaaatcagttggagctattgaaccaatcgatcctgaatc
FCV-FK      4801 cctgaaaccaactcgggttgacaagtccgttggagcaattgagcctattgatcctgactc
FCV-KF      4801 cttaaaacccacaagggtcgacaaatcagttggagctattgaaccaatcgatcctgaatc

FCV-F9      4921 tcgcagctctataataagacaattctattatattaaaggtgagaactccgatgactggaa
FCV-Kalem   4921 tcgcagctcaatcctcagacagttctattacattaaaggtgaaaattcggatgattggaa
FCV-FK      4921 tcgcagctctataataagacaattctattatattaaaggtgagaactccgatgactggaa
FCV-KF      4921 tcgcagctcaatcctcagacagttctattacattaaaggtgaaaattcggatgattggaa
```

FIG.6-14

CONTINUED ON FIG.6-16

CONTINUED FROM FIG.6-13

CONTINUED ON FIG.6-16

```
FCV-F9      5041 gagcccccaaaacatattgacccaacatctcgagggcaacagctttggaatgcctgtct
FCV-Kalem   5041 aactcctccaaaagtcatagatcccacctccagaggtcaacagctgtggaacgcttgtct
FCV-FK      5041 gagcccccaaaacatattgacccaacatctcgagggcaacagctttggaatgcctgtct
FCV-KF      5041 aactcctccaaaagtcatagatcccacctccagaggtcaacagctgtggaacgcttgtct

FCV-F9      5161 tgttgaatatgaagagctgcactttgaacccccaacatatgcttcggctttggatcatta
FCV-Kalem   5161 tgttgaatacgaaggattacacctcgacccccccaagcttccaatcggcattggaacatta
FCV-FK      5161 tgttgaatatgaagagctgcactttgaacccccaacatatgcttcggctttggatcatta
FCV-KF      5161 tgttgaatacgaaggattacacctcgacccccccaagcttccaatcggcattggaacatta

FCV-F9      5281 cgccctacactgtgatgtgttcgaagtttgagcatgtgctcaacctgcgctaacgtgctt
FCV-Kalem   5281 cgccctacactgtgatgtgttcgaagtttgagcatgtgctcaacctgcgctaacgtgctt
FCV-FK      5281 cgccctacactgtgatgtgttcgaagtttgagcatgtgctcaacctgcgctaacgtgctt
FCV-KF      5281 cgccctacactgtgatgtgttcgaagtttgagcatgtgctcaacctgcgctaacgtgctt

FCV-F9      5401 gttggctttgtagtaaccctttaatgtgttgctacccagaactccttccggaatttgga
FCV-Kalem   5401 gttggattctgtgataacccgcttatgtgttgctatcctgagttgcttccagaattcggc
FCV-FK      5401 gttggattctgtgataacccgcttatgtgttgctatcctgagttgcttccagaattcggc
FCV-KF      5401 gttggctttgtagtaaccctttaatgtgttgctacccagaactccttccggaatttgga

FCV-F9      5521 gatgaatgggcatccactttgacgctgttgacccagtcgttcccccaatgcactggggt
FCV-Kalem   5521 gatgaatggtcttctacctatgaagccattgaccctgtcgttccaccaatgcactgggac
FCV-FK      5521 gatgaatggtcttctacctatgaagccattgaccctgtcgttccaccaatgcactgggac
FCV-KF      5521 gatgaatgggcatccactttgacgctgttgacccagtcgttcccccaatgcactggggt

FCV-F9      5641 gttgctgcaggttgggaccccgatctgcctctaattcgactcgaggcggatgacgggtca
FCV-Kalem   5641 gttgccaagggatgggatccaaacttgcctttgttccgattggaggccgatgatggatcg
FCV-FK      5641 gttgccaagggatgggatccaaacttgcctttgttccgattggaggccgatgatggatcg
FCV-KF      5641 gttgctgcaggttgggaccccgatctgcctctaattcgactcgaggcggatgacgggtca
```

FIG.6-15

CONTINUED ON FIG.6-17

CONTINUED FROM FIG.6-15

CONTINUED FROM FIG.6-14

```
FCV-F9      5041 gtacgctagccaacatggcttggagttttcaacaaggtttacaggctggccgagagggc
FCV-Kalem   5041 ttatgctagccaacatggtgttgagttttacaataaggttctcaaattggcccagaaagc
FCV-FK      5041 gtacgctagccaacatggcttggagttttcaacaaggtttacaggctggccgagagggc
FCV-KF      5041 ttatgctagccaacatggtgttgagttttacaataaggttctcaaattggcccagaaagc

FCV-F9      5161 caacagccagttcaatggcgtggaggcgcggtctgaccagatcgactcgagtggcatgac
FCV-Kalem   5161 caataaccaatttagtggtgtggaggcgcggaatgaccagatcgattcgagtggcatgtc
FCV-FK      5161 caacagccagttcaatggcgtggaggcgcggtctgaccagatcgactcgagtggcatgac
FCV-KF      5161 caataaccaatttagtggtgtggaggcgcggaatgaccagatcgattcgagtggcatgac

FCV-F9      5281 aaatattatgattgggacccccatttcaaattggtaatcaaccccaacaacttcctctct
FCV-Kalem   5281 aaatactatgattgggatccccacttcaaattggtgatcgaccctaataaatttctttct
FCV-FK      5281 aaatactatgattgggatccccacttcaaattggtgatcgaccctaataaatttctttct
FCV-KF      5281 aaatattatgattgggacccccatttcaaattggtaatcaaccccaacaacttcctctct

FCV-F9      5401 actgtttgggattgcgatcggtcaccacttgaaatttacctagaatcaatacttggtgat
FCV-Kalem   5401 actgtgtgggattgtgatcaatctccactgcaaatttaccttgaatctattcttggtgat
FCV-FK      5401 actgtgtgggattgtgatcaatctccactgcaaatttaccttgaatctattcttggtgat
FCV-KF      5401 actgtttgggattgcgatcggtcaccacttgaaatttacctagaatcaatacttggtgat

FCV-F9      5521 gctgctggaaaaattttccagccacaccccggtgttctcatgcaccatctcattggtaag
FCV-Kalem   5521 aaaatggggaaaatcttccaacctcaccctggtatgctaatgcaccatatcatcggtgaa
FCV-FK      5521 aaaatggggaaaatcttccaacctcaccctggtatgctaatgcaccatatcatcggtgaa
FCV-KF      5521 gctgctggaaaaattttccagccacaccccggtgttctcatgcaccatctcattggtaag

FCV-F9      5641 atcacagcacccgagcaaggaacaatggttggcggcgtcatcgctgaacccagcgcccag
FCV-Kalem   5641 gtgacaacccctgaacaaggaacaatggttggcggagtcattgctgaacccagcgcccaa
FCV-FK      5641 gtgacaacccctgaacaaggaacaatggttggcggagtcattgctgaacccagcgcccaa
FCV-KF      5641 atcacagcacccgagcaaggaacaatggttggcggcgtcatcgctgaacccagcgcccag
```

FIG.6-16

CONTINUED ON FIG.6-18

CONTINUED FROM FIG.6-15

CONTINUED ON FIG.6-18

```
FCV-F9      5761 atgtcaacagctgctgatatggccaccgggaaaagcgttgattctgagtgggaggcattc
FCV-Kalem   5761 atgtcaactgctgctgacatggcctctgggaaaagtgttgactccgaatgggaggctttc
FCV-FK      5761 atgtcaactgctgctgacatggcctctgggaaaagtgttgactccgaatgggaggctttc
FCV-KF      5761 atgtcaacagctgctgatatggccaccgggaaaagcgttgattctgagtgggaggcattc

FCV-F9      5881 aaacaatccttaggccctttgctcaacccatatctagaacaccttgctaagctatatgtt
FCV-Kalem   5881 aaacaatcacttggacccctgctaaacccatatcttgaacacatatctaagctttatgtt
FCV-FK      5881 aaacaatcacttggacccctgctaaacccatatcttgaacacatatctaagctttatgtt
FCV-KF      5881 aaacaatccttaggccctttgctcaacccatatctagaacaccttgctaagctatatgtt

FCV-F9      6001 aagctcgcagctattgttgtacctcctggggttgatccagtgcagagtacttcgatgcta
FCV-Kalem   6001 aaactcgctgctattgttgtgccgcctggggtagacccagtgcaaagcacatcaatgcta
FCV-FK      6001 aaactcgctgctattgttgtgccgcctggggtagacccagtgcaaagcacatcaatgcta
FCV-KF      6001 aagctcgcagctattgttgtacctcctggggttgatccagtgcagagtacttcgatgcta

FCV-F9      6121 gatctaagaagcaccctgtaccaccttatgtctgacactgacactacatccttggtcatt
FCV-Kalem   6121 gatttgagaaacagcttgtaccatcttatgtcagatactgatactacctcccttgtaatt
FCV-FK      6121 gatttgagaaacagcttgtaccatcttatgtcagatactgatactacctcccttgtaatt
FCV-KF      6121 gatctaagaagcaccctgtaccaccttatgtctgacactgacactacatccttggtcatt

FCV-F9      6241 gtcactgtcgagacaaaacctggccctgacttcaagtttcacctccttaagccacccgga
FCV-Kalem   6241 gtcactgttgagactaaacctggaatcgatttcaagtttcaccttctgaaacccccctgga
FCV-FK      6241 gtcactgttgagactaaacctggaatcgatttcaagtttcaccttctgaaacccccctgga
FCV-KF      6241 gtcactgtcgagacaaaacctggccctgacttcaagtttcacctccttaagccacccgga

FCV-F9      6361 atcggtaaccgctactggtcagacataactgattttgtgattcggccgtttgtcttccaa
FCV-Kalem   6361 atagggaatcgtcactggactgacataaccgattttgtcattaggcctttttgtgttccaa
FCV-FK      6361 atagggaatcgtcactggactgacataaccgattttgtcattaggcctttttgtgttccaa
FCV-KF      6361 atcggtaaccgctactggtcagacataactgattttgtgattcggccgtttgtcttccaa
```

CONTINUED ON FIG.6-19

FIG.6-17

CONTINUED FROM FIG.6-17

CONTINUED FROM FIG.6-16

```
FCV-F9      5761 ttctcctttcacaccagcgtcaattggagtacatctgaaacccaaggaaagattctcttc
FCV-Kalem   5761 ttctcatttcacactagtgtaaattggagtacatctgaaacacaaggaaagattctattc
FCV-FK      5761 ttctcattncacactagtgtaaattggagtacatctgaaacacaaggaaagattctattc
FCV-KF      5761 ttctcctttcacaccagcgtcaattggagtacatctgaaacccaaggaaagattctcttc

FCV-F9      5881 gcgtggtctgggtcgattgaggttaggttctctatctctggctctggtgtctttggtggg
FCV-Kalem   5881 gcatggtctggatctatagaggttaggttttctatttctggttctggtgttttggggga
FCV-FK      5881 gcatggtctggatctatagaggttaggttttctatttctggttctggtgttttggggga
FCV-KF      5881 gcgtggtctgggtcgattgaggttaggttctctatctctggctctggtgtctttggtggg

FCV-F9      6001 caataccccatgtttgtttgatgctcgtcaggtggaaccagttatcttctgtcttcct
FCV-Kalem   6001 cagtatcctcatgttctatttgatgcccgtcaggtagaacctgttatcttttcaatacct
FCV-FK      6001 cagtatcctcatgttctatttgatgcccgtcaggtagaacctgttatcttttcaatacct
FCV-KF      6001 caataccccatgtcttgtttgatgctcgtcaggtggaaccagttatcttctctattcct

FCV-F9      6121 atggtgtacaatgatctcatcaatccctatgccaatgatgccaactcttctgggtgtatt
FCV-Kalem   6121 atggtgtacaatgatcttattaatccttatgcaaatgattctaactcttctggatgtatt
FCV-FK      6121 atggtgtacaatgatcttattaatccttatgcaaatgattctaactcttctggatgtatt
FCV-KF      6121 atggtgtacaatgatctcatcaatccctatgccaatgatgccaactcttctgggtgtatt

FCV-F9      6241 tctatgctaacccatggctctatcccttctgatttaattcccaaaacatcttcgctctgg
FCV-Kalem   6241 tctatgcttacccatggctctatcccttcagatttaataccaaaatcttcttctctttgg
FCV-FK      6241 tctatgcttacccatggctctatcccttcagatttaataccaaaatcttcttctctttgg
FCV-KF      6241 tctatgctaacccatggttctgtcccttctgatttaattcccaaaacatcttcgctctgg

FCV-F9      6361 gcaaatcgtcattttgactttaatcaagagaccgcaggtggagcacaccacggtttcgg
FCV-Kalem   6361 gcaaaccgtcattttgatttaatcaggaaacagctggttggagtacgccaagattccga
FCV-FK      6361 gcaaaccgtcattttgatttaatcaggaaacagctggttggagtacgccaagattccga
FCV-KF      6361 gcaaatcgtcattttgactttaatcaagagaccgcaggtggagcacaccacggtttcgg
```

CONTINUED ON FIG.6-20

FIG.6-18

CONTINUED FROM FIG.6-17

CONTINUED ON FIG.6-20

```
FCV-F9      6481 cctatatctgttaccattactgaacagaacggagcaaaattgggcattggggtggcaaca
FCV-Kalem   6481 ccactagccgtaacggttagccaaagtaaaggagcaaaattggggaatggtattgcgacc
FCV-FK      6481 ccactagccgtaacggttagccaaagtaaaggagcaaaattggggaatggtattgcgacc
FCV-KF      6481 cctatatctgttaccattactgaacagaacggagcaaaattgggcattggagtggcaaca

FCV-F9      6601 ataccagctggtgattacgcaatcaccaatggtactggcaatgacatcaccacggctaca
FCV-Kalem   6601 acacccacaggcgattatgcaattacatctagtgatggtaatgacattgaaacaaaactt
FCV-FK      6601 acacccacaggcgattatgcaattacatctagtgatggtaatgacattgaaacaaaactt
FCV-KF      6601 ataccagctggcgattacgcaatcaccaatggtactggcaatgacatcaccacggctaca

FCV-F9      6721 ggttcgctccagcgtgcctggggtgataagaaaatttccaacactgcctttatcaccact
FCV-Kalem   6721 gggtcgctccaaagagcctggggtgataagaagatttctaatactggtttcataactact
FCV-FK      6721 gggtcgctccaaagagcctggggtgataagaagatttctaatactggtttcataactact
FCV-KF      6721 ggttcgctccagcgtgcctggggtgataagaaaatttccaacactgcctttatcaccact

FCV-F9      6841 aagatcgtcgtgtttcaagacaaccatgttggaaagaaagcgcaaacctcagacgataca
FCV-Kalem   6832 aaaatcgtggtctatcaagacaatcatgtcaatagtgaagttcaaacctcagacatcaca
FCV-FK      6832 aaaatcgtggtctatcaagacaatcatgtcaatagtgaagttcaaacctcagacatcaca
FCV-KF      6841 aagatcgtcgtgtttcaagacaaccatgttggaaagaaagtgcaaacctcagacgataca

FCV-F9      6961 gttgtgcgcatcagcactctccctgaaactggtgctcgaggcggtaaccacccaattttc
FCV-Kalem   6952 gttgtacgcataagtgtgctgccagaaacaggtgcccgtgggggaaaccatccaatcttt
FCV-FK      6952 gttgtacgcataagtgtgctgccagaaacaggtgcccgtgggggaaaccatccaatcttt
FCV-KF      6961 gttgtgcgcatcagcactctccctgaaactggtgctcgaggcggtaaccacccaattttc

FCV-F9      7081 atcttgcacacttccagacagttatcgctaaatcattacctactcccacctgattctttt
FCV-Kalem   7072 atcttgcacacctctagacaactatcactgaataactacttactacctccagattctttt
FCV-FK      7072 atcttgcacacctctagacaactatcactgaataactacttactacctccagattctttt
FCV-KF      7081 atcttgcacacttccagacagttatcgctaaatcattacctactcccacctgattctttt
```

FIG.6-19

CONTINUED ON FIG.6-21

CONTINUED FROM FIG.6-19

CONTINUED FROM FIG.6-18

```
FCV-F9      6481 cattacatagtgcctggaatccctgatggctggcctgacaccacaattcctggggagttg
FCV-Kalem   6481 cactacatcgtgcctgggattcctgatggatggccagacactacaatcccaacaaaactg
FCV-FK      6481 cactacatcgtgcctgggattcctgatggatggccagacactacaatcccaacaaaactg
FCV-KF      6481 cattacatagtgcctggaatccctgatggctggcctgacaccacaattcctggggagttg

FCV-F9      6601 ggatatgacactgctgatataattaagaacaataccaactttaggggcatgtacatatgt
FCV-Kalem   6601 gaatacgaaaatgctgatgtgattaaaaacaacacaaacttcaggagcatgtacatttgt
FCV-FK      6601 gaatacgaaaatgctgatgtgattaaaaacaacacaaacttcaggagcatgtacatttgt
FCV-KF      6601 ggatatgacactgctgatataattaagaacaataccaactttaggggcatgtacatatgt

FCV-F9      6721 gccaccctagatggtgacaacaacaacaagatcaatccctgtaataccatagaccagtca
FCV-Kalem   6721 ---------ggtgttatctctgataattccataagcccaagcaataccattgatcaaagc
FCV-FK      6721 ---------ggtgttatctctgataattccataagcccaagcaataccattgatcaaagc
FCV-KF      6721 gccaccctagatggtgacaacaacaacaagatcaatccctgtaataccatagaccagtca

FCV-F9      6841 ttggccctgcttggttacactggcattggtgagcaggccatcggtctgatagggaccgg
FCV-Kalem   6832 cttgcaattcttggctacactggtattggtgaggaggcaattggcgccaatcgggactcg
FCV-FK      6832 cttgcaattcttggctacactggtattggtgaggaggcaattggcgccaatcgggactcg
FCV-KF      6841 ttggccctgcttggttacactggcattggtgagcaggccatcggtctgatagggaccgg

FCV-F9      6961 tacaagaactccattaaattgggatatgtaattaggtctattgatgtctttaattcacaa
FCV-Kalem   6952 tataagaattctatgaagcttggttacgtgatcagctccattgatgtgtttaattcccag
FCV-FK      6952 tataagaattctatgaagcttggttacgtgatcagctccattgatgtgtttaattcccag
FCV-KF      6961 tacaagaactccattaaattgggatatgtaattaggtctattgatgtctttaattcacaa

FCV-F9      7081 gccgtctatagaataattgactcaaatggctcgtggtttgatattggaattgatagtgat
FCV-Kalem   7072 gctgtctatcgaattattgattctaatgggtcttggtttgatataggcattgattctgat
FCV-FK      7072 gctgtctatcgaattattgattctaatgggtcttggtttgatataggcattgattctgat
FCV-KF      7081 gccgtctatagaataattgactcaaatggctcgtggtttgatattggaattgatagtgat
```

FIG.6-20

CONTINUED ON FIG.6-22

CONTINUED FROM FIG.6-19

CONTINUED ON FIG.6-22

```
FCV-F9      7201 gggttctcttttgttggtgtttctggctttggtaaattagaatttcccctttctgcctcc
FCV-Kalem   7192 ggattttcttttgttggtgtctcaagttttcctaagttagagtttccactttctgcctcc
FCV-FK      7192 ggattttcttttgttggtgtctcaagttttcctaagttagagtttccactttctgcctcc
FCV-KF      7201 gggttctcttttgttggtgtttctggctttggtaaattagaatttcccctttctgcctcc

FCV-F9      7321 aagttatgaattcaatattaggcctgattgatactgttactaacactattggtaaagctc
FCV-Kalem   7312 aaattatgaattcaatattaggcttaattgacactgttacaaatacaattggcaaagctc
FCV-FK      7312 aaattatgaattcaatattaggcttaattgacactgttacaaatacaattggcaaagctc
FCV-KF      7321 aagttatgaattcaatattaggcctgattgatactgttactaacactattggtaaagctc

FCV-F9      7441 ttggcttggaccgccaagccttaaacaaccaagttgagcagtttaacaaaattcttgagc
FCV-Kalem   7432 ttaaccttgatcgccaggcgttgaacaaccaagttgagcaatttaacaaaattcttgagc
FCV-FK      7432 ttaaccttgatcgccaggcgttgaacaaccaagttgagcaatttaacaaaattcttgagc
FCV-KF      7441 ttggcttggaccgccaagccttaaacaaccaagttgagcagtttaacaaaattcttgagc

FCV-F9      7561 acccttactcatacacaaaccaaaactttttatgacgatcaattaaatgcaattagactat
FCV-Kalem   7552 acccttactcatacacaaatcaaaattttttacgatgaccaattgaatgcaattagactat
FCV-FK      7552 acccttactcatacacaaatcaaaattttttacgatgaccaattgaatgcaattagactat
FCV-KF      7561 acccttactcatacacaaaccaaaactttttatgacgatcaattaaatgcaattagactat

FCV-F9      7678 cctaaccccaggg
FCV-Kalem   7672 cctaaccccaggg
FCV-FK      7672 cctaaccccaggg
FCV-KF      7678 cctaaccccaggg
```

FIG.6-21

CONTINUED FROM FIG.6-21

CONTINUED FROM FIG.6-20

```
FCV-F9      7201 tacatgggaatacaattggcaaagatccggcttgcctctaacattaggagtcccatgact
FCV-Kalem   7192 tatatgggaattcagttggcaaagattcgtcttgcctctaatattaggagttctatgact
FCV-FK      7192 tatatgggaattcagttggcaaagattcgtcttgcctctaatattaggagttctatgact
FCV-KF      7201 tacatgggaatacaattggcaaagatccggcttgcctctaacattaggagtcccatgact

FCV-F9      7321 agcagattgaattggacaaagctgcacttggtcaacagcgtgaattggctctccagcgca
FCV-Kalem   7312 aacaaattgaattagataaagctgcacttggtcaacaacgcgaactggctttgcaacgaa
FCV-FK      7312 aacaaattgaattagataaagctgcacttggtcaacaacgcgaactggctttgcaacgaa
FCV-KF      7321 aacagattgaattggacaaagctgcacttggtcaacagcgtgaattggctctccagcgca

FCV-F9      7441 aaagggtacaaggcccaatccaatccgttcgccttgcgcgcgcggctggatttagggttg
FCV-Kalem   7432 aaagggtacaaggccccatccagtctgtgcggctcgcacgtgctgctggatttagggttg
FCV-FK      7432 aaagggtacaaggccccatccagtctgtgcggctcgcacgtgctgctggatttagggttg
FCV-KF      7441 aaagggtacaaggcccaatccaatccgttcgccttgcacgcgcggctggatttagggttg

FCV-F9      7561 catataaaaatttgtttaaa-atttgatcata--tatccctttgggctgccgcacctgcg
FCV-Kalem   7552 cttataggaatttgtttaaataattggccacaagtatcccttcgggctgccgcatttgcg
FCV-FK      7552 cttataggaatttgtttaaataattggccacaagtatcccttcgggctgccgcatttgcg
FCV-KF      7561 catataaaaatttgtttaaa-atttgatcata--tatccctttgggctgccgcacctgcg
```

FIG.6-22

CONTINUED ON FIG.7-2

```
FCV Kalem         1 mcstcanvlkyydwdphfklvidpnkflsvgfcdnplmccypellpefgtvwdcdqsplqiyles
FCV-F9            1 mcstcanvlkyydwdphfklvinpnnflsvgfcsnplmccypellpefgtvwdcdrspleiyles
FCV-UTCVM-NH3     1 mcstcanvlkyydwdphfkliinpnkflsvgfcdnplmccypellpefgtvwncnqsplqiyles
FCV-12Q087-5      1 mcstcanvlkyydwdphfrltinpnkflsvgfcdnplmccypellpefgtvwdcnqspleiyles
FCV-12Q087-1      1 mcstcanvlkyydwdphfrltinpnkflsvgfcdnplmccypellpefgtvwdcdqspleiyles
FCV-1874          1 mcstcanvlkyynwdphfklvinpnkflpigfcdnplmccypellpefgtvwdcdqsplqiyles
FCV-2024          1 mcstcanvlkyydwdphirlvidpnrflsvsfcdkpllccypdllpefgtvwdcnqspleiyles
FCV-2280          1 mcstcanvlkyygwdphfrlvvnpnkflsvgfcdnplmccypdllpefgtlwdcdqsplqiyles
FCV-3786          1 mcstcanvlkyydwdphfrliinpnkflsvgfcdnplmccypellpefgtvwdcdqspleifles
FCV-5789          1 mcstcanvlkyydwdphfklvinpnkflpigfcdnpllccypellpefgtvwdcgqsplqiyles
FCV-20879         1 mcstcanvlkyydwdphiqlvinpnkflpvgfcdnplmccfpellpefgtvwdcdqsplqiyles
FCV-21223         1 mcstcanvlkyydwdphfrliinpnkflsvgfcdnplmccypellpefgtvwdcdqspleiyles
FCV-21749         1 mcstcanvlkyydwdphfklvinpnkflavgfcdnplmccypellpefgtvwdcnqsplqiyles
FCV-DD-2006-GE    1 mcstcanvlkyydwdphfrlvidpnkflsvgfcnnplmccypellpefgtvwdcdqaplqiyles
FCV-F4            1 mcstcanvlkyydwdphfrliinpnkflpigfcdnplmccypdllpefgtvwdcdqsplqiyles
FCV-F65           1 mcstcanvlkyynwdphiklsinpnkflsvgfcdnplmccypellpefgtmwdcdqsplqiyles
FCV-FB-NJ-13      1 mcstcanvlkyygwdphfrltinpndflsvgfcdnplmccypellpefgtvwdcndsplqiyles
FCV-GD            1 mcstcanvlkyygwdphfdlvinpndflsvgfcdnplmccypellpefgtvwdcndsplqiyles
FCV-HRB-SS        1 mcstcanvlkyynwdphfkmvvnpnkflsvgfcdkpllccypdllpefgtvwdcnqspleiyles
FCV-Urbana        1 mcstcanvlkyynwdphfklvinpnkflsigfcdnplmccypellpefgtvwdcdqsplqiyles
FCV-USDA          1 mcstcanvlkyydwdphirlvidpnrflsvsfcdkpllccypdllpefgtvwdcnqspleiyles
FCV-UTCVM-H1      1 mcstcanvlkyydwdphfrlnvnpneflsvgfcdkplmccypellpefgtvwdcsrapleiyles
FCV-UTCVM-NH2     1 mcstcanvlkyygwdphfklvinpnnflpvgfcsnplmccypellpefgtvwdcdrspleiyles
FCV-UTCVM-H2      1 mcstcanvlkyydwdphirlvinpnkflpigfcdnplmccypellpefgtvwdcdqsplqiyles
FCV-UTCVM-NH1     1 mcstcanvlkyydwdphfrlvidpnkflsvgfcdnplmccypellpefgtvwdcdqsplqiyles
```

CONTINUED ON FIG.7-3

FIG. 7-1

CONTINUED FROM FIG.7-1

| | | |
|---|---|---|
| FCV Kalem | 1 | ilgddewsstyeaidpvvppmhwdkmgkifqphpgmlmhhiigevakgwdpnlplfrlead-dgs |
| FCV-F9 | 1 | ilgddewastfdavdpvvppmhwgaagkifqphpgvlmhhligkvaagwdpdlplirlead-dgs |
| FCV-UTCVM-NH3 | 1 | ilgddewvstyeaidpvvppmhwneagklfqphpgilmhhiigevakawdpnlplfrlead-dgs |
| FCV-12Q087-5 | 1 | ilgddewastyeaidpvvppmhwdcagkifqphpgvlmhhlisevakgwdpnlpsfrlead-dgs |
| FCV-12Q087-1 | 1 | ilgddewastyeaidpvvppmhwdcagkifqphpgvlmhhlisevakgwdpnlpsfrlead-dgs |
| FCV-1874 | 1 | ilgddewsstyeaidpvvppmhwdkagkifqphpgvlmhyiigevakawdpnlplfrlead-dgs |
| FCV-2024 | 1 | ilgddewsstfeaidpvvppmhwdeagkifqphpgvlmhhlinqvakawdpnlplfrlead-dgs |
| FCV-2280 | 1 | ilgddewastyeaidpsvppmhwdamgkifqphpgvlmhhiigevakawdpnlplfrlead-dgs |
| FCV-3786 | 1 | ilgddewastyeaidpvvppmhwdsagkifqphpgvlmhhligevakawdpnlplfrlead-dgs |
| FCV-5789 | 1 | ilgddewsstyeaidpvvppmhwdeagkifqphpgvlmnyiigevakawdpnlplfrlead-dgs |
| FCV-20879 | 1 | ilgddewastfeavepsvppmhwdeagkifqphpgvlmhhligevakawdpnlplfrlead-dgs |
| FCV-21223 | 1 | ilgddewastyeaidpvvppmhwdsagkifqphpgvlmhhligevakawdpnlplfrlead-dgs |
| FCV-21749 | 1 | ilgddewsstyeaidpvvppmhwdeagkifqphpgvlmhhligevakawdpnlplfrlead-dgs |
| FCV-DD-2006-GE | 1 | ilgddewsstfeaidpvvppmhwngagkifqphpgilthhllsevakgwdpnlplfrlegdsdss |
| FCV-F4 | 1 | ilgddewastheaidpsvppmhwdsagkifqphpgvlmhhligevakawdpnlplfrlead-dgs |
| FCV-F65 | 1 | ilgddewastyeaidpvvppmhwdemgkifqphpgvlmhhiigevakgwdpnlplfrlead-dgs |
| FCV-FB-NJ-13 | 1 | ilgddewsstyeaidpvvppmhwdqagkifqphpgvlmhhllgkvakgwdpnlpsfrlesd-dgs |
| FCV-GD | 1 | ilgddewsstyeaidpvvppmhwkqagkifqphpghlmhhligkvskgwdpnlpnfrlead-dgs |
| FCV-HRB-SS | 1 | ilgddewsstfeaidpvvppmhwddagkifqphpgvlmhhlisevakgwdpnlplfrlead-dgs |
| FCV-Urbana | 1 | ilgddewsstyeaidpvvppmhwneagkifqphpgvlmhhiigevakawdpnlplfrlead-dgs |
| FCV-USDA | 1 | ilgddewsstfeaidpvvppmhwdeagkifqphpgvlmhhlinqvakawdpnlplfrlead-dgs |
| FCV-UTCVM-H1 | 1 | ilgddewsstheaidpvvppmhwdeagkifqphpgvlmhhlinkvarawdpnlplfrlead-dgs |
| FCV-UTCVM-NH2 | 1 | ilgddewastfdavdpvvppmhwsaagkifqphpgvlmhhligkvaagwdpdlplirlead-dgs |
| FCV-UTCVM-H2 | 1 | ilgddewastydaidpvvppmhwddagkifqphpgvlmhflinevakgwdpslpsfrlead-dgs |
| FCV-UTCVM-NH1 | 1 | ilgddewastyeaidpsvppmhwdsagkifqphpgvlmhyiigevakawdpnlpnfrlead-dgs |

CONTINUED ON FIG.7-4

FIG.7-2

CONTINUED FROM FIG.7-1

CONTINUED ON FIG.7-4

| | | |
|---|---|---|
| FCV Kalem | 129 | vttpeqgtmvggviaepsaqmstaadmasgksvdsew-eaffsfhtsvnwstsetqgkilfkqsl |
| FCV-F9 | 129 | itapeqgtmvggviaepsaqmstaadmatgksvdsew-eaffsfhtsvnwstsetqgkilfkqsl |
| FCV-UTCVM-NH3 | 129 | ittpeqgtpvggviaepsaqmsaaadmatgksvdsew-eaffsfhtsvnwstsetqgkilfkqsl |
| FCV-12Q087-5 | 129 | ittpeqgtpvggviaepsaqmstaadmasgksvdsewgkaffsfhtsvnwstsetqgkilfkqsl |
| FCV-12Q087-1 | 129 | ittpeqgtpvggviaepsaqmstaadmasgksvdsewgkaffsfhtsvnwstsetqgkilfkqsl |
| FCV-1874 | 129 | ittpeqgtvvggviaepssqmstaadmasgksvdsew-eaffsfhtsvnwstsetqgkilfkqsl |
| FCV-2024 | 129 | itspeqgtmvggviaepsaqmstaadmatgksvdsew-eaffsfhtsvnwstsetqgkilfkqsl |
| FCV-2280 | 129 | itapeqgtvvggviaepsaqmstaadmatgksvdsew-eaffsfhtsvnwsttetqgkilfkqsl |
| FCV-3786 | 129 | ittpeqgtsvggviaepsaqmstaadmatgktvdsew-eaffsfhtsvnwstsetqgkilfkqsl |
| FCV-5789 | 129 | itapeqgtvvggviaepssqmstaadmasgksvdsew-eaffsfhtsvnwstsetqgkilfkqsl |
| FCV-20879 | 129 | ittpeqgtmvggviaepsaqmstaadmatgksvdsew-eaffsfhtsvnwstsetqgkilfkqsl |
| FCV-21223 | 129 | ittpeqgtsvggviaepsaqmstaadmatgktvdsew-eaffsfhtsvnwstsetqgkilfkqsl |
| FCV-21749 | 129 | ittpeqgtsvggviaepsaqmaaaadmatgksvdsew-eaffsfhtsvnwsttetqgkilfkqsl |
| FCV-DD-2006-GE | 130 | vttpeqgtmvggviaepsaqmstaadmasgksvdsew-eaffsfhtsvnwstsetqgkilfkqsl |
| FCV-F4 | 129 | ittpeqgtavggviaepsaqmstaadmasgksvdsew-eaffsfhtsvnwstsetqgkilfkqsl |
| FCV-F65 | 129 | ittpeqgtmvggviaepsaqmstaadmatgksvdsew-eaffsfhtsvnwstsetqpkilfkqsl |
| FCV-FB-NJ-13 | 129 | ittpeqgtlvggviaepstqmataadmatgktvdsew-eaffsfhtsvnwstsetqgkilfkqnl |
| FCV-GD | 129 | itapeqgtlvggviaepsaqmstaadmatgktvdsew-eaffsfhtsvnwstsetqgkilfkqsl |
| FCV-HRB-SS | 129 | itapeqgtvvggviaepspqmavaadtatgksvdsew-eaffsfhtsvnwstsetqgkilfkqsl |
| FCV-Urbana | 129 | itapeqgtvvggviaepssqmstaadmasgksvdsew-eaffsfhtsvnwstsetqgkilfkqsl |
| FCV-USDA | 129 | itspeqgtmvggviaepsaqmstaadmatgksvdsew-eaffsfhtsvnwstsetqgkilfkqsl |
| FCV-UTCVM-H1 | 129 | ittpeqgtlvggviaepssqmsaaadmatgksvdsew-eaffsfhtsvnwstsetqgkilfkqsl |
| FCV-UTCVM-NH2 | 129 | itapeqgtmvggviaepsaqmstaadmatgksvdsew-eaffsfhtsvnwstsetqgkilfkqsl |
| FCV-UTCVM-H2 | 129 | ittpeqgtavggviaqpsaqmsaaadmasgksvdsew-eeffsfhtsvnwsttetqgkilfkqsl |
| FCV-UTCVM-NH1 | 129 | ittpeqgtmvggviaepsaqmataadtatgksvdsew-eaffsfhtsvnwstsetqgkilfkqsl |

CONTINUED ON FIG.7-5

FIG.7-3

CONTINUED FROM FIG.7-3

CONTINUED FROM FIG.7-2

| | | |
|---|---|---|
| FCV Kalem | 129 | gpllnpylehisklyvawsgsievrfsisgsgvfggklaaivvppgvdpvqstsmlqyphvlfda |
| FCV-F9 | 129 | gpllnpylehlaklyvawsgsievrfsisgsgvfggklaaivvppgvdpvqstsmlqyphvlfda |
| FCV-UTCVM-NH3 | 129 | gpllnpylshlaklyvawsgsievrfsisgsgvfggklaaiivppgiepvqstsmlqyphvlfda |
| FCV-12Q087-5 | 129 | gpllnpylehlaklyvawsgsvevrfsisgsgvfggklaaivvppgvdpvqstsmlqyphvlfda |
| FCV-12Q087-1 | 129 | gpllnpylehlaklyvawsgsvevrfsisgsgvfggklaaivvppgvdpvqstsmlqyphvlfda |
| FCV-1874 | 129 | gpllnpylehlsklyvawsgsvevrfsisgsgvfggklaaivvppgvdpiqstsmlqyphvlfda |
| FCV-2024 | 129 | gpllnpylehlaklyvawsgsvdvrfsisgsgvfggklaaivvppgvnpvqstsmlqyphvlfda |
| FCV-2280 | 129 | gpllnpylehlaklyvawsgsidvrfsisgsgvyggklaaivvppgvdpvqstsmlqyphvlfda |
| FCV-3786 | 129 | gpllnpylthlaklyvawsgsvevrfsisgsgvfggklaaivvppgvdpvqstsmlqyphvlfda |
| FCV-5789 | 129 | gpllnpylehlsklyvawsgsvevrfsisgsgvfggklaaivvppgvdpiqstsmlqyphvlfda |
| FCV-20879 | 129 | gpllnpylthlaklyvawsgsievrfsisgsgvfggklaaivvppgidpvqstsmlqyphvlfda |
| FCV-21223 | 129 | gpllnpylthlaklyvawsgsvevrfsisgsgvfggklaaivvp?gvdpvqstsmlqyphvlfda |
| FCV-21749 | 129 | gpllnpylehlaslyvawsgsievrfsisgsgvfggklaaivvppginpvqstsmlqyphvlfda |
| FCV-DD-2006-GE | 130 | gpllnpylehlaklyvawsgsievrfsisgsgvfggklaaivvppgvnpvqstsmlqyphvlfda |
| FCV-F4 | 129 | gpllnpylehlsklyvawsgsievrfsisgsgvfggklaaivvppgvdpvqstsmlqyphvlfda |
| FCV-F65 | 129 | gpllnpylqhlaklyvawsgsievrfsisgsgvfggklaaivvppgvdpvqstsmlqyphvlfda |
| FCV-FB-NJ-13 | 129 | gpllnpylehiaqlyvawsgsvdvrfsisgsgvfggklaaivvppgvqpvqstsmlqyphvlfda |
| FCV-GD | 129 | gpllnpylghlaqlyvawsgsvdvrfsisgsgvfggklaaivvppgvrpvqstsmlqyphvlfda |
| FCV-HRB-SS | 129 | gpllnpylehlsklyvawsgsvevrfsisgsgvfggklaaivvppgvdpvqstsmlqyphvlfda |
| FCV-Urbana | 129 | gpllnpylehlsklyvawsgsvevrfsisgsgvfggklaaivvppgvdpiqstsmlqyphvlfda |
| FCV-USDA | 129 | gpllnpylehlaklyvawsgsvdvrfsisgsgvfggklaaivvppgvnpvqstsmlqyphvlfda |
| FCV-UTCVM-H1 | 129 | gpllnpylehlsklyvawsgsvevrfsisgsgvfggklaaivvppgvdpvqstsmlqyphvlfda |
| FCV-UTCVM-NH2 | 129 | gpllnpylehlaklyvawsgsievrfsisgsgvfggklaaivvppgvdpvqstsmlqyphvlfda |
| FCV-UTCVM-H2 | 129 | gpllnpylehlsklyvawsgsidvrfsisgsgvfggklaaivvppgvdpvqstsmlqyphvlfda |
| FCV-UTCVM-NH1 | 129 | gpllnpylthlaklyvawsgsievrfsisgsgvfggklaaivvppgidpvqstsmlqyphvlfda |

CONTINUED ON FIG.7-6

FIG.7-4

CONTINUED FROM FIG.7-3

CONTINUED ON FIG.7-6

```
FCV Kalem        258 rqvepvifsipdlrnslyhlmsdtdttslvimvyndlinpyandsnssgcivtvetkpgldfkfh
FCV-F9           258 rqvepvifclpdlrstlyhlmsdtdttslvimvyndlinpyandanssgcivtvetkpgpdfkfh
FCV-UTCVM-NH3    258 rqvepviftipdlrsnlyhlmsdtdttslvimiyndlinpyandsnssgcivtvetkpgadfkfh
FCV-12Q087-5     259 rqvepviftipdlrnslyhlmsdtdttslvimvyndlinpyasdsnssgcivtvetkpgpdfkfh
FCV-12Q087-1     259 rqvepviftipdlrnslyhlmsdtdttslvimvyndlinpyasdsnssgcivtvetkpgpdfkfh
FCV-1874         258 rqvepviftipdlrstlyhlmsdtdttslvvmvyndlinpyandsnssgcivtvetkpgsdfkfh
FCV-2024         258 rqvepvifsipdlrstlyhlmsdtdttslvimvyndlinpyasdsnssgcivtvetkpgpdfkfh
FCV-2280         258 rqvepvifsipdlrstlyhlisdtdttslvimvyndlinpyasdtnssgcivtvetkpgpdfkfh
FCV-3786         258 rqvepviftipdlrstlyhlmsdtdttslvimvyndlinpyandtnssgcivtvetkpgpdfkfh
FCV-5789         258 rqvepviftipdlrsnlyhlmsdtdttslvimvyndlinpyandsnssgcivtvetkpgpdfkfh
FCV-20879        258 rqvdpviftipdlrstlyhlmsdtdttslvimvyndlinpyasdsnssgcivtvetkpgpdfkfh
FCV-21223        258 rqvepviftipdlrstlyhlmsdtdttslvimvyndlinpyandtnssgcivtvetkpgpdfkfh
FCV-21749        258 rqvepvifsipdlrnslyhlmsdtdttslvimvyndlinpyandtnssgcivtvetkpgpdfkfh
FCV-DD-2006-GE   259 rqvepvifsipdlrstlyhlmsdtdttslvimvyndlinpyandtnssgcivtvetkpgpdfrfh
FCV-F4           258 rqvepviftipdlrstlyhvmsdtdttslvimvyndlinpyandsnssgcivtvetkpgpdfkfh
FCV-F65          258 rqvdpviftipdlrstlyhlmsdtdttplvimvyndlinpyandsnssgcivtvetkpgpdfkfh
FCV-FB-NJ-13     258 rqvepvifsipdlrsnlyhlmsdtdttslvimvyndlinpyandsnssgciitvetkpgpdfkfh
FCV-GD           258 rqvepvifsipdlrsslyhlmsdtdttslvimvyndlinpyagdsnssgciitvetkpgadfkfh
FCV-HRB-SS       258 rqvepviftlpdlrnslyhlmsdtdttslvimvyndlinpyandsnssgcvvtvetkpgadfkfh
FCV-Urbana       258 rqvepviftipdlrstlyhlmsdtdttslvimvyndlinpyandsnssgcivtvetkpgsdfkfh
FCV-USDA         258 rqvepvifsipdlrstlyhlmsdtdttslvimvyndlinpyasdsnssgcivtvetkpgpdfkfh
FCV-UTCVM-H1     258 rqvdpviftipdlrsnlyhlmsdtdttslvimvyndlinpyandsnssgcivtvetkpgpdfkfh
FCV-UTCVM-NH2    258 rqvepvifsipdlrstlyhlmsdtdttslvimvyndlinpyandanssgcivtvetkpgpdfkfh
FCV-UTCVM-H2     258 rqvepvifslpdlrnslyhlisdtdttslvimvyndlinpyaneanssgcivtvetkpgpdfkfh
FCV-UTCVM-NH1    258 rqvepviftipdlrstlyhlmsdtdttslvimvyndlinpyandsnssgciltvetkpgpdfkfh
```

CONTINUED ON FIG.7-7

FIG. 7-5

CONTINUED FROM FIG.7-5

CONTINUED FROM FIG.7-4

| | | |
|---|---|---|
| FCV Kalem | 258 | llkppgsmlthgsipsdlipksssIwignrhwtditdfvirpfvfqanrhfdfnqetagwstprf |
| FCV-F9 | 258 | llkppgsmlthgsipsdlipktsslwignrywsditdfvirpfvfqanrhfdfnqetagwstprf |
| FCV-UTCVM-NH3 | 258 | llkppgsmlthgsipsdlipksssIwignrhwtditefvvrpfvfqanrhfdfnqetagwstprf |
| FCV-12Q087-5 | 259 | llkppgsmlthgsvpsdlipksssIwignrywsditdfvirpfvfqanrhfdfnqetagwstprf |
| FCV-12Q087-1 | 259 | llkppgsmlthgsvpsdlipksssIwigiclwrgitdfvirpfvfqvnrhfdfnqetagwstprf |
| FCV-1874 | 258 | llkppgsvlthgsvpsdliprtsslwignrfwtditdfvirpfvfqanrhfdfnqetagwstprf |
| FCV-2024 | 258 | llkppgsmlthgsvpsdlipksssIwignrhwtditdfvirpfvfqanrhfdfnqetagwstprf |
| FCV-2280 | 258 | llkppgsmlthgsipadlipksssIwignrywsditefvvrpfvfqanrhfdfnqetagwstprf |
| FCV-3786 | 258 | llkppgsmlthgsvpsdlipksssIwignrywsditdfvirpfvfqanrhfdfnqetagwstprf |
| FCV-5789 | 258 | llkppgsmlthgsvpsdliprtsslwvgnrfwgditdfvirpfvfqanrhfdfnqetagwstpqf |
| FCV-20879 | 258 | llkppgsmlthgsvpsdlipksssIwignrhwtditdfvirpfvfqanrhfdfnqetagwstprf |
| FCV-21223 | 258 | llkppgsmlthgsvpsdlipksssIwignrywsditdfvirpfvfqanrhfdfnqetagwstprf |
| FCV-21749 | 258 | llkppgsmlthgsipsdlipksssIwignrywsditdfiirpfvfqanrhfdfnqetagwstprf |
| FCV-DD-2006-GE | 259 | llkppgsmlthgsvpsdlipksssIwignrhwtditdfvirpfvfqanrhfdfnqetagwstprf |
| FCV-F4 | 258 | llkppgsvlthgsipsdlipksssIwignrywtditdfvirpfvfqanrhfdfnqetagwstprf |
| FCV-F65 | 258 | llkppgsmlthgsvpsdlipksssIwignrhwtditdfvirpfvfqanrhfdfnqetagwstpry |
| FCV-FB-NJ-13 | 258 | llkppgsmlvhgsipsnlipksssIwignrhwsditdfvirpsvfqanrhfdfkqetagwstprf |
| FCV-GD | 258 | llkppgsvlthgsvpsdlipktsslwignrhwaditdfvirpsvfqanrhfdfkqetagwstprf |
| FCV-HRB-SS | 258 | llkppgsmlthgsvpsdliprsssIwignrywtditdfvirpfvfqanrhfdfnqetagwstprf |
| FCV-Urbana | 258 | llkppgsmlthgsvpsdlipktsslwignrfwsditdfvirpfvfqanrhfdfnqetagwstprf |
| FCV-USDA | 258 | llkppgsmlthgsvpsdlipksssIwignrhwtditdfvirpfvfqanrhfdfnqetagwstprf |
| FCV-UTCVM-H1 | 258 | llkppgsmlthgsvpsdlipksssIwignrhwtditdfvirpfvfqanrhfdfnqetagwstprf |
| FCV-UTCVM-NH2 | 258 | llkppgsmlthgsvpsdlipktsslwignrywsditdfvirpfvfqanrhfdfnqetagwstprf |
| FCV-UTCVM-H2 | 258 | llkppgsmlthgsipsdliprsssIwignrhwtditdfvirpfvfqanrhfdfnqetagwstprf |
| FCV-UTCVM-NH1 | 258 | llkppgsmlthgsvpsdlipksssIwignrywsdindfvirpfvfqanrhfdfnqetagwstprf |

CONTINUED ON FIG.7-8

FIG. 7-6

CONTINUED FROM FIG.7-5

CONTINUED ON FIG.7-8

| | | |
|---|---|---|
| FCV Kalem | 388 | rplavtvsqskgaklgngiatdyivpgipdgwpdttiptkltptgdyaitssdgndietkleyen |
| FCV-F9 | 388 | rpisvtiteqngaklgigvatdyivpgipdgwpdttipgelipagdyaitngtgndittatgydt |
| FCV-UTCVM-NH3 | 388 | rpitvtvsekggsklgigvatdsivpgipdgwpdtsisdtlipsgdyaitsgngndiitgadyds |
| FCV-12Q087-5 | 389 | rpltitisveggaklgtgvatdyivpgipdgwpdttipekltpagdyaitdgngsdivtaakydt |
| FCV-12Q087-1 | 389 | rpltitisvkeganselgvatdyivpgipdgwpdttipekltpagdyaitdssgsdittaakyda |
| FCV-1874 | 388 | rpitvtisekdgaklgigvatdfivpgipdgwpdttigerlvpvgdyaitnsagidittasqydt |
| FCV-2024 | 388 | rpititisekdgsklgigvamdsivpgipdgwpdttipeklvpagnyaiangtgndittakdyds |
| FCV-2280 | 388 | rpitvtvsesggsklgigvatdyivpgipdgwpdttipekltpagnyaittsnnsdiatateydh |
| FCV-3786 | 388 | rpititisvkesaklgtgvatdyivpgipdgwpdttipeeltpagdyaitnssgndittaagfda |
| FCV-5789 | 388 | rpitvtisvkngeklgigiatdfivpgipdgwpdttigeelvpagdyaittssgndittaqqyda |
| FCV-20879 | 388 | rpititisvnnaaklgtgvatdyivpgipdgwpdttipseltpagdyaitnssgndittavgydt |
| FCV-21223 | 388 | rpititisvkelaklgtgvatdyivpgipdgwpdttipeeltpagdyaitnssgndittaadfda |
| FCV-21749 | 388 | rpitvtisqkegeklgigvatdyivpgipdgwpdttipgkltpvgnyaitdesgsdivtaaefds |
| FCV-DD-2006-GE | 389 | rpltvtisqkdgdklgtgvatdyivpgipdgwpdttipgelipagdyaittgngtdittaqvfds |
| FCV-F4 | 388 | rpititisekngsklgigvatdyiipgipdgwpdttiadklipagdysittgegndiktaqaydt |
| FCV-F65 | 388 | rpitvsisqqegaklgigvaidyivpgipdgwprstipsklvpaggyaitakngndittaaqyda |
| FCV-FB-NJ-13 | 388 | rpmtitisqkqsaklgiavalesivpgipdgwpdttidsnlipagdyaitnqadndittameyda |
| FCV-GD | 388 | rpmtvtisqsggaklgigiahetivpgipdgwpdttipgelvpageyaivnqtsndiatavdydt |
| FCV-HRB-SS | 388 | rpititisekngeklgigvatdyivpgipdgwpdttiaekltpagdyaittgdgndiitanaydt |
| FCV-Urbana | 388 | rpitvtisekngaklgvgvatdfivpgipdgwpdttigeklvpagdyaitngsgndittanqyda |
| FCV-USDA | 388 | rpititisekdgsklgigvamdsivpgipdgwpdttipeklvpagdyaiangtgndittakdyds |
| FCV-UTCVM-H1 | 388 | rplsvtisqsggaklgigiatdyivpgipdgwpdttipgeltpagdyaivnqnnsdiatkqayes |
| FCV-UTCVM-NH2 | 388 | rpisvtisqqdgaklgigvatdyivpgipdgwpdttipgelipagdyaitnnigdditTatgydt |
| FCV-UTCVM-H2 | 388 | rpitinisqkegarlgtaiavdtilpgipdgwpdttiptvltpagkyaitsgnnsdiltrndyen |
| FCV-UTCVM-NH1 | 388 | rpitvtisvkesaklgigvatdyivpgipdgwpdttiptdltpagdyaitdstgndittpsgyds |

CONTINUED ON FIG.7-9

FIG.7-7

CONTINUED FROM FIG.7-7

CONTINUED FROM FIG.7-6

| | | |
|---|---|---|
| FCV Kalem | 388 | adviknntnfrsmyicgslqrawgdkkisntgfittgvi---s---dnsispsntidqskivvyq |
| FCV-F9 | 388 | adiiknntnfrgmyicgslqrawgdkkisntafittatldgdn---nnkinpcntidqskivvfq |
| FCV-UTCVM-NH3 | 388 | adviknntnfrsmyicgslqrawgdkkvsetafittavr---n---ensispsnvidatklivyq |
| FCV-12Q087-5 | 389 | adviknntnfkgmyicgslqrawgdkkisntafittgtv---e---nnsiepsntidatklavfq |
| FCV-12Q087-1 | 389 | advienntnfkgmyicgslqrawgdkkisntafittgtv---e---dnfiepsntidatklavfq |
| FCV-1874 | 388 | agviknntnfrgmyicgslqrawgdkkisntafittatv---n---rndlipsnvidqtkiaifq |
| FCV-2024 | 388 | atviqnntnfkgmyicgslqrawgdkkisntafittatr---s---dntitpsnvidptkiavyq |
| FCV-2280 | 388 | adeiknntnfksmyicgslqrawgdkkisntafittavk---e---gnsitpsntidmtklvvyq |
| FCV-3786 | 388 | adviknntnfrgmyicgslqrawgdkkisntafittgtv---e---ggkirpsnvidqtkiavfq |
| FCV-5789 | 388 | adiinnntnfksmyicgslqrawgdkkisntafittatv---s---gnklipsnvidqtkiaifq |
| FCV-20879 | 388 | adeiknntnfrgmyicgslqrawgdkkisntafittgiv---t---gnklqpsntidqtkiavfq |
| FCV-21223 | 388 | admiknntnfrgmyicgslqrawgdkkisntafittgtv---e---ggkirpsnvidqtkiavfq |
| FCV-21749 | 388 | atgiknntefrgmyicgslqrawgdkkisntafittakv---n---nnmlepsnvidqtkiaifq |
| FCV-DD-2006-GE | 389 | adviqnntnfrgmyicgslqrawgdkkisntafittaiv---k---ggklrpsnvidqtkiaifq |
| FCV-F4 | 388 | aavvknttnfrgmyicgslqrawgdkkisntafittair---d---gneikpsntidmtklavyq |
| FCV-F65 | 388 | ageivnntnfksmyicgalqrawgdkkvsntafvttatv---t---gntlkpsntidntkiaiyq |
| FCV-FB-NJ-13 | 388 | ateiknntnfrsmyicgalqrawgdkkvsntafittadl---d---gntikpnnvinqsriivyq |
| FCV-GD | 388 | ataitnntnfksmyicgalqrawgdkkisntafittadl---n---gnkikpnnvinqqrivifq |
| FCV-HRB-SS | 388 | advvknntnfrgmyicgslqrawgdkkisntafittgtv---s---dnkikpsnvidptklavfq |
| FCV-Urbana | 388 | adiirnntnfkgmyicgslqrawgdkkisntafittatv---e---gndlipsnvidqtkiaifq |
| FCV-USDA | 388 | atviqnntnfkgmyicgslqrawgdkkisntafittatr---s---dntitpsnvidptkiavyq |
| FCV-UTCVM-H1 | 388 | atsienntnfksmyicgslhrawgdkkisntafittatv---d---gnnlipsntigqdkiavfq |
| FCV-UTCVM-NH2 | 388 | adiiknntnfkgmyicgslqrawgdkkisntafittatl---sgnnnnkinpcntidqskivvfq |
| FCV-UTCVM-H2 | 388 | adviknntnfrsmyicgslqrawgdkdisntafittgtv---n---gnniepsntidptklavfq |
| FCV-UTCVM-NH1 | 388 | aisivnntnfrgmyicgslqrawgdkkvsntafittgiv---t---gnklepsntidqtkiaifq |

CONTINUED ON FIG.7-10

FIG.7-8

CONTINUED FROM FIG.7-7

CONTINUED ON FIG.7-10

| | | |
|---|---|---|
| FCV Kalem | 512 | dnhvnsevqtsditlailgytgigeeaiganrdsvvrisvlpetgarggnhpifyknsmklgyvi |
| FCV-F9 | 515 | dnhvgkkaqtsddtlallgytgigeqaigsdrdrvvristlpetgarggnhpifyknsiklgyvi |
| FCV-UTCVM-NH3 | 512 | dahvetdvqtsdvtlailgytgigeeaigldrdkvvrisilpetgtrggnhpifyknsiklgyvi |
| FCV-12Q087-5 | 513 | dthvghevqtsddtlallgytgigeqaigsdrdrvvrisvlpetgarggnhpifyknsiklgyvi |
| FCV-12Q087-1 | 513 | dthvgrevqtsddtlallgytgigeqaigsdrdrvvrisvlpetgarggnhpifyknsiklgyvv |
| FCV-1874 | 512 | dnhvgvdvqtsddtlallgytgigeeaigadrervvristlpetgarggnhpifyknsiklgyvv |
| FCV-2024 | 512 | dthvgaevqtsddtlailgytgigeeaigadrdrvvrisvlpetgarggnhpifyknsiklgyvi |
| FCV-2280 | 512 | dahvgndvqtsdvtlallgytgigeqaigsdrdrvvrisvlpetgarggnhpifykntiklgyvi |
| FCV-3786 | 512 | dthanrevqtsddtlallgytgigeeaigadrdrvvrisvlpetgarggnhpifyknsiklgyvi |
| FCV-5789 | 512 | dthanqgvqtsddtlailgytgigeeaiganrervvristlpeagarggnhpifykntmklgyvi |
| FCV-20879 | 512 | dthankdpqtsddtlallgytgigeeaigadrdrvvrisvlpeagarggnhpifyknsiklgyvi |
| FCV-21223 | 512 | dthvnqevqtsddtlallgytgigeeaigadrdrvvrisvlpetgarggnhpifyknsiklgyvi |
| FCV-21749 | 512 | dnhvgrdvqtsddtlallgytgigeqaigsdrdrvvrisilpeagarggnhpifyknsiklgyvl |
| FCV-DD-2006-GE | 513 | dnhvqagiqtsddtlavlgytgigeqaigadrdrvvrisvlpetgarggnhpifyknsiklgyvi |
| FCV-F4 | 512 | dthvgqevqtsddtlallgytgigeeaigsnrdrvvrisvlpeagarggnhpifyknsiklgyvi |
| FCV-F65 | 512 | dnhvnsdvqtsdvtlsllgytgigeeavgadrdklvrisvlpetgarggnhpifyknsiklgyvi |
| FCV-FB-NJ-13 | 512 | dnhvnlqvqtsevtlamlgytgigeeviganrdrvvrinvlpevsarggnhpiyyknslklgyvi |
| FCV-GD | 512 | dnhvgseaqtsdvtlamlgytgigeevigadrdrvvrinvlpevsarggnhpifykntlklgyvi |
| FCV-HRB-SS | 512 | dnhvgadaqtsddtlallgytgigehaigadrervvristlpetgarggnhpifyknsiklgyvi |
| FCV-Urbana | 512 | dnhvqdevqtsddtlallgytgigeeaiganrervvristlpetgarggnhpifyknsiklgyvi |
| FCV-USDA | 512 | dthvgaevqtsddtlailgytgigeeaigadrdrvvrisvlpetgarggnhpifyknsiklgyvi |
| FCV-UTCVM-H1 | 512 | dnhvnaevqtsdvtlatlgytgigeeaigairdrvvrisvlpetgarggnhpifyknamklgyvi |
| FCV-UTCVM-NH2 | 515 | dnhvgkevqtsddtlallgytgigeqaigsdrdrvvristlpetgarggnhpifyknsiklgyvi |
| FCV-UTCVM-H2 | 512 | dnhvksevqtsdvtlsvlgytgigeeavgadrdkvvrisvlpetgarggnhpifyknsmklgyvi |
| FCV-UTCVM-NH1 | 512 | dthanrdtqisddtlallgytgigeeaigadrdrvvrisvlpetgarggnhpifyknsiklgyvi |

CONTINUED ON FIG.7-11

FIG.7-9

CONTINUED FROM FIG.7-9

CONTINUED FROM FIG.7-8

| | | |
|---|---|---|
| FCV Kalem | 512 | ssidvfnsqilhtsrqlslnnyllppdsfavyriidsngswfdigidsdgfsfvgvssfpklefp |
| FCV-F9 | 515 | rsidvfnsqilhtsrqlslnhyllppdsfavyriidsngswfdigidsdgfsfvgvsgfgklefp |
| FCV-UTCVM-NH3 | 512 | rsidvmnsqilhtsrqlslnnyslppdsfavyriidsagswfdigidsdgfsfvgisnvgklifp |
| FCV-12Q087-5 | 513 | rsidvfnsqilhtsrqlslnhyllppdsfavyriidsngswfdigidsdgfsfvgvssitklefp |
| FCV-12Q087-1 | 513 | rsidvfnsqilhtsrqlslnhyllppdsfavyriidsngswfdigidsdgfsfvgvssitklefp |
| FCV-1874 | 512 | rsidvfnsqilhtsrqlslnnyllppdsfavyriidsngswfdigidtdgfsfvgvsnigklefp |
| FCV-2024 | 512 | rsidvfnsqilhtsrqlslnnyllppdsfavyritdsngswfdigidsdgfsfvgasnvgklefp |
| FCV-2280 | 512 | rsidvfnsqilhtsrqlslnhyllppdsfavyriidsngswfdigidsdgfsfvgvsslptlefp |
| FCV-3786 | 512 | rsidvfnsqilhtsrqlslnhyllspdslavyritdsngswfdigidsdgfsfvgvsnigklefp |
| FCV-5789 | 512 | rsidvfnsqilhtsrqlslnnyllppdsfavyritdsngswfdigidtdgfsfvgvssignlefp |
| FCV-20879 | 512 | rsidvfnsqilhtsrqlslnhyllspdsfavyriidsngswfdigidsegfsfvgvssigklefp |
| FCV-21223 | 512 | rsidvfnsqilhtsrqlslnhyllspdslavyritdsngswfdigidsdgfsfvgvsnigklefp |
| FCV-21749 | 512 | rsidvfnsqilhtsrqlslnhyllspdsfavyriidsngswfdigidsdgfsfvgvsaigkleyp |
| FCV-DD-2006-GE | 513 | rsidvfnsqilhtsrqlslnhyllppdsfavyriidsngswfdigidsdgfsfvgvsnigklefp |
| FCV-F4 | 512 | rsidvfnsqilhtsrqlslnhyllppdsfavyriidsngswfdigidsegfsfvgvsdigklefp |
| FCV-F65 | 512 | rsidvfnsqilhtsrqlslnnyllppdsfavyriidangswfdigidsdgfsfvgvsnigklefp |
| FCV-FB-NJ-13 | 512 | rsidvfnsqilhtsrqlalnnylldpdcfavyritdsngswfdigidysgfsfvgvsnigalefp |
| FCV-GD | 512 | rsidvfnsqilhtsrqlalnnylldpdsfavyritdsngswfdigidysgfsfvgvsnigelefp |
| FCV-HRB-SS | 512 | rsidvfnsqilhtsrqlslnhyllppdsfavyriidsngswfdigidsdgfsfvgvtnigklefp |
| FCV-Urbana | 512 | rsidvfnsqilhtsrqlslnhyllppdsfavyriidsngswfdvgidfdgfsfvgvsdvgklefp |
| FCV-USDA | 512 | rsidvfnsqilhtsrqlslnnyllppdsfavyritdsngswfdigidsdgfsfvgasnvgklefp |
| FCV-UTCVM-H1 | 512 | gdidvfnsqilhtsrqlslnnyllppdsfavyriidsngswfdvgidsdgfsfvgvssipklefp |
| FCV-UTCVM-NH2 | 515 | rsidvfnsqilhtsrqlslnhyllppdsfavyriidsngswfdigidsdgfsfvgvsgfgklefp |
| FCV-UTCVM-H2 | 512 | ssidvfnsqilhtsrqlslnhyllppdsfavyritdsngswfdigidndgfsfvgvshigklefp |
| FCV-UTCVM-NH1 | 512 | rsidvfnsqilhtsrqlslnhyllspdsfavyritdsngswfdigidsdgfsfvgvnnigklefp |

FIG.7-10

CONTINUED FROM FIG.7-9

| | | |
|---|---|---|
| FCV Kalem | 642 | lsasymgiqlakirlasnirssmtkl* |
| FCV-F9 | 645 | lsasymgiqlakirlasnirspmtkl* |
| FCV-UTCVM-NH3 | 642 | lsasymgiqlakirlasnirsamtkl* |
| FCV-12Q087-5 | 643 | ltasymgiqlakirlasnirgqmtki* |
| FCV-12Q087-1 | 643 | ltasymgiqlakirlasnirsqmtki* |
| FCV-1874 | 642 | ltasymgiqlakirlasnirstmikl* |
| FCV-2024 | 642 | ltasymgiqlakirlasnirssmtkl* |
| FCV-2280 | 642 | lsasymgiqlakirlasnirssmtkl* |
| FCV-3786 | 642 | ltasymgiqlakvrlasnirssmtkl* |
| FCV-5789 | 642 | lsasymgiqlakirlasnirstmtkl* |
| FCV-20879 | 642 | ltasymgiqlakirlasnirstltkl* |
| FCV-21223 | 642 | ltasymgiqlakvrlasnirssmtkl* |
| FCV-21749 | 642 | ltasymgiqlakvrlasnirssmtkl* |
| FCV-DD-2006-GE | 643 | lsasymgiqlakirlasnirssmtkl* |
| FCV-F4 | 642 | lsasymgiqlakirlasnirsrmtkl* |
| FCV-F65 | 642 | lsasymgiqlakirlasnirstmtkl* |
| FCV-FB-NJ-13 | 642 | ltasytgiqlakirlasnirssmtkl* |
| FCV-GD | 642 | ltasymgvqlakirlasnirssmtkl* |
| FCV-HRB-SS | 642 | lsasymgiqlakirlasnirssmikl* |
| FCV-Urbana | 642 | ltasymgiqlakirlasnirstmtkl* |
| FCV-USDA | 642 | ltasymgiqlakirlasnirssmtkl* |
| FCV-UTCVM-H1 | 642 | lsasymgiqlakirlasnirstmtkl* |
| FCV-UTCVM-NH2 | 645 | lsasymgiqlakirlasnirspmtkl* |
| FCV-UTCVM-H2 | 642 | lsasymgiqlakirlasnirssmikl* |
| FCV-UTCVM-NH1 | 642 | ltasymgiqlakirlasnirstmtkl* |

FIG.7-11

SEQUENCE LISTING

<160> NUMBER OF SEQ ID NOS: 66

<210> SEQ ID NO 1
<211> LENGTH: 50
<212> TYPE: DNA
<213> ORGANISM: Feline calicivirus

<400> SEQUENCE: 1
catggtacct aatacgactc actatagggt aaaagaaatt tgagacaatg 50

<210> SEQ ID NO 2
<211> LENGTH: 49
<212> TYPE: DNA
<213> ORGANISM: Feline calicivirus

<400> SEQUENCE: 2
tcgaccaccg gtgattaatt tttttttttt tttttttttt ttccctggg 49

<210> SEQ ID NO 3
<211> LENGTH: 67
<212> TYPE: DNA
<213> ORGANISM: Feline calicivirus

<400> SEQUENCE: 3
tacctaatac gactcactat agggtaaaag aaatttgaga caatgtctca aactctgagc 60
ttcgtgc 67

<210> SEQ ID NO 4
<211> LENGTH: 48
<212> TYPE: DNA
<213> ORGANISM: Feline calicivirus

<400> SEQUENCE: 4
tttttttttt tttttttttt ttttccctgg ggttaggcgc aggtgcgg 48

<210> SEQ ID NO 5
<211> LENGTH: 44
<212> TYPE: DNA
<213> ORGANISM: Feline calicivirus

<400> SEQUENCE: 5
gtaaaagaaa tttgagacaa tgtctcaaac tctgagcttc gtgc 44

<210> SEQ ID NO 6
<211> LENGTH: 53
<212> TYPE: DNA
<213> ORGANISM: Feline calicivirus

<400> SEQUENCE: 6
atagtattta agcacgttag cgcaggttga gcacatgctc aaacttcgaa cac 53

<210> SEQ ID NO 7
<211> LENGTH: 52
<212> TYPE: DNA
<213> ORGANISM: Feline calicivirus

<400> SEQUENCE: 7
gagtggcatg accgccctac actgtgatgt gttcgaagtt tgagcatgtg ct 52

-continued

<210> SEQ ID NO 8
<211> LENGTH: 36
<212> TYPE: DNA
<213> ORGANISM: Feline calicivirus

<400> SEQUENCE: 8
tttttttttt ttccctgggg ttaggcgcag gtgcgg 36

<210> SEQ ID NO 9
<211> LENGTH: 36
<212> TYPE: DNA
<213> ORGANISM: Feline calicivirus

<400> SEQUENCE: 9
cttggtaccg agctgtaaaa gaaatttgag acaatg 36

<210> SEQ ID NO 10
<211> LENGTH: 18
<212> TYPE: DNA
<213> ORGANISM: Feline calicivirus

<400> SEQUENCE: 10
tgagctgttc tttgcaca 18

<210> SEQ ID NO 11
<211> LENGTH: 21
<212> TYPE: DNA
<213> ORGANISM: Feline calicivirus

<400> SEQUENCE: 11
ctccttgaaa gagttggtgt g 21

<210> SEQ ID NO 12
<211> LENGTH: 20
<212> TYPE: DNA
<213> ORGANISM: Feline calicivirus

<400> SEQUENCE: 12
ctatggtgca ttcggtgatg 20

<210> SEQ ID NO 13
<211> LENGTH: 20
<212> TYPE: DNA
<213> ORGANISM: Feline calicivirus

<400> SEQUENCE: 13
gcgacaactc ttgtatcagg 20

<210> SEQ ID NO 14
<211> LENGTH: 20
<212> TYPE: DNA
<213> ORGANISM: Feline calicivirus

<400> SEQUENCE: 14
gacatgcttg agaacaaggg 20

<210> SEQ ID NO 15
<211> LENGTH: 16
<212> TYPE: DNA
<213> ORGANISM: Feline calicivirus

<400> SEQUENCE: 15
gaactacccg ccaatc 16

-continued

<210> SEQ ID NO 16
<211> LENGTH: 15
<212> TYPE: DNA
<213> ORGANISM: Feline calicivirus

<400> SEQUENCE: 16
gagcccaggc caaat 15

<210> SEQ ID NO 17
<211> LENGTH: 31
<212> TYPE: DNA
<213> ORGANISM: Feline calicivirus

<400> SEQUENCE: 17
gatcggtcga cgagctcttc tctctcttag g 31

<210> SEQ ID NO 18
<211> LENGTH: 20
<212> TYPE: DNA
<213> ORGANISM: Feline calicivirus

<400> SEQUENCE: 18
gtatgacgta acaaagcctg 20

<210> SEQ ID NO 19
<211> LENGTH: 20
<212> TYPE: DNA
<213> ORGANISM: Feline calicivirus

<400> SEQUENCE: 19
ggaaattggc aacccaaggc 20

<210> SEQ ID NO 20
<211> LENGTH: 20
<212> TYPE: DNA
<213> ORGANISM: Feline calicivirus

<400> SEQUENCE: 20
gctgtaaaag tgtcctctgg 20

<210> SEQ ID NO 21
<211> LENGTH: 19
<212> TYPE: DNA
<213> ORGANISM: Feline calicivirus

<400> SEQUENCE: 21
cactgtgatg tgttcgaag 19

<210> SEQ ID NO 22
<211> LENGTH: 18
<212> TYPE: DNA
<213> ORGANISM: Feline calicivirus

<400> SEQUENCE: 22
tatttaagca cgttagcg 18

<210> SEQ ID NO 23
<211> LENGTH: 20
<212> TYPE: DNA
<213> ORGANISM: Feline calicivirus

<400> SEQUENCE: 23
catcttatgt cagatactga 20

<210> SEQ ID NO 24
<211> LENGTH: 20
<212> TYPE: DNA
<213> ORGANISM: Feline calicivirus

<400> SEQUENCE: 24
ttttcttttg ttggtgtctc 20

<210> SEQ ID NO 25
<211> LENGTH: 34
<212> TYPE: DNA
<213> ORGANISM: Feline calicivirus

<400> SEQUENCE: 25
cgagcggccg ccactgtgcc ctggggttag gcgc 34

<210> SEQ ID NO 26
<211> LENGTH: 18
<212> TYPE: DNA
<213> ORGANISM: Feline calicivirus

<400> SEQUENCE: 26
gggagatgag aagcttcg 18

<210> SEQ ID NO 27
<211> LENGTH: 19
<212> TYPE: DNA
<213> ORGANISM: Feline calicivirus

<400> SEQUENCE: 27
gcccaaacta tgaaacaag 19

<210> SEQ ID NO 28
<211> LENGTH: 20
<212> TYPE: DNA
<213> ORGANISM: Feline calicivirus

<400> SEQUENCE: 28
aacgccattg gatctgtaac 20

<210> SEQ ID NO 29
<211> LENGTH: 20
<212> TYPE: DNA
<213> ORGANISM: Feline calicivirus

<400> SEQUENCE: 29
attgaaccaa tcgatcctga 20

<210> SEQ ID NO 30
<211> LENGTH: 20
<212> TYPE: DNA
<213> ORGANISM: Feline calicivirus

<400> SEQUENCE: 30
tcaggatcga ttggttcaat 20

<210> SEQ ID NO 31
<211> LENGTH: 32
<212> TYPE: DNA
<213> ORGANISM: Feline calicivirus

<400> SEQUENCE: 31

-continued ttccaggtac ctccggaagg agttctgggt ag 32

<210> SEQ ID NO 32
<211> LENGTH: 53
<212> TYPE: DNA
<213> ORGANISM: Feline calicivirus

<400> SEQUENCE: 32
agagctctct ggctaacgta aaagaaattt gagacaatgt ctcaaactct gag 53

<210> SEQ ID NO 33
<211> LENGTH: 34
<212> TYPE: DNA
<213> ORGANISM: Feline calicivirus

<400> SEQUENCE: 33
ggcaactaga aggcacagcc ctggggttag gcgc 34

<210> SEQ ID NO 34
<211> LENGTH: 668
<212> TYPE: PRT
<213> ORGANISM: Feline calicivirus

<400> SEQUENCE: 34

Met Cys Ser Thr Cys Ala Asn Val Leu Lys Tyr Tyr Asp Trp Asp Pro
1 5 10 15

His Phe Lys Leu Val Ile Asp Pro Asn Lys Phe Leu Ser Val Gly Phe
20 25 30

Cys Asp Asn Pro Leu Met Cys Cys Tyr Pro Glu Leu Leu Pro Glu Phe
35 40 45

Gly Thr Val Trp Asp Cys Asp Gln Ser Pro Leu Gln Ile Tyr Leu Glu
50 55 60

Ser Ile Leu Gly Asp Asp Glu Trp Ser Ser Thr Tyr Glu Ala Ile Asp
65 70 75 80

Pro Val Val Pro Pro Met His Trp Asp Lys Met Gly Lys Ile Phe Gln
85 90 95

Pro His Pro Gly Met Leu Met His His Ile Ile Gly Glu Val Ala Lys
100 105 110

Gly Trp Asp Pro Asn Leu Pro Leu Phe Arg Leu Glu Ala Asp Asp Gly
115 120 125

Ser Val Thr Thr Pro Glu Gln Gly Thr Met Val Gly Gly Val Ile Ala
130 135 140

Glu Pro Ser Ala Gln Met Ser Thr Ala Ala Asp Met Ala Ser Gly Lys
145 150 155 160

Ser Val Asp Ser Glu Trp Glu Ala Phe Phe Ser Phe His Thr Ser Val
165 170 175

Asn Trp Ser Thr Ser Glu Thr Gln Gly Lys Ile Leu Phe Lys Gln Ser
180 185 190

Leu Gly Pro Leu Leu Asn Pro Tyr Leu Glu His Ile Ser Lys Leu Tyr
195 200 205

Val Ala Trp Ser Gly Ser Ile Glu Val Arg Phe Ser Ile Ser Gly Ser
210 215 220

Gly Val Phe Gly Gly Lys Leu Ala Ala Ile Val Val Pro Pro Gly Val
225 230 235 240

Asp Pro Val Gln Ser Thr Ser Met Leu Gln Tyr Pro His Val Leu Phe
245 250 255

-continued

```
Asp Ala Arg Gln Val Glu Pro Val Ile Phe Ser Ile Pro Asp Leu Arg
            260                 265                 270

Asn Ser Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Ile Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Leu Ala Val Thr Val Ser Gln Ser Lys Gly
385                 390                 395                 400

Ala Lys Leu Gly Asn Gly Ile Ala Thr Asp Tyr Ile Val Pro Gly Ile
                405                 410                 415

Pro Asp Gly Trp Pro Asp Thr Thr Ile Pro Thr Lys Leu Thr Pro Thr
            420                 425                 430

Gly Asp Tyr Ala Ile Thr Ser Ser Asp Gly Asn Asp Ile Glu Thr Lys
        435                 440                 445

Leu Glu Tyr Glu Asn Ala Asp Val Ile Lys Asn Asn Thr Asn Phe Arg
    450                 455                 460

Ser Met Tyr Ile Cys Gly Ser Leu Gln Arg Ala Trp Gly Asp Lys Lys
465                 470                 475                 480

Ile Ser Asn Thr Gly Phe Ile Thr Thr Gly Val Ile Ser Asp Asn Ser
                485                 490                 495

Ile Ser Pro Ser Asn Thr Ile Asp Gln Ser Lys Ile Val Val Tyr Gln
            500                 505                 510

Asp Asn His Val Asn Ser Glu Val Gln Thr Ser Asp Ile Thr Leu Ala
        515                 520                 525

Ile Leu Gly Tyr Thr Gly Ile Gly Glu Glu Ala Ile Gly Ala Asn Arg
    530                 535                 540

Asp Ser Val Val Arg Ile Ser Val Leu Pro Glu Thr Gly Ala Arg Gly
545                 550                 555                 560

Gly Asn His Pro Ile Phe Tyr Lys Asn Ser Met Lys Leu Gly Tyr Val
                565                 570                 575

Ile Ser Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Asp Gly Phe Ser Phe Val Gly Val Ser Ser Phe Pro Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Ser Met Thr Lys Leu
            660                 665
```

-continued

<210> SEQ ID NO 35
<211> LENGTH: 671
<212> TYPE: PRT
<213> ORGANISM: Feline calicivirus

<400> SEQUENCE: 35

```
Met Cys Ser Thr Cys Ala Asn Val Leu Lys Tyr Tyr Asp Trp Asp Pro
1               5                   10                  15

His Phe Lys Leu Val Ile Asn Pro Asn Asn Phe Leu Ser Val Gly Phe
            20                  25                  30

Cys Ser Asn Pro Leu Met Cys Cys Tyr Pro Glu Leu Leu Pro Glu Phe
        35                  40                  45

Gly Thr Val Trp Asp Cys Asp Arg Ser Pro Leu Glu Ile Tyr Leu Glu
    50                  55                  60

Ser Ile Leu Gly Asp Asp Glu Trp Ala Ser Thr Phe Asp Ala Val Asp
65                  70                  75                  80

Pro Val Val Pro Pro Met His Trp Gly Ala Ala Gly Lys Ile Phe Gln
                85                  90                  95

Pro His Pro Gly Val Leu Met His His Leu Ile Gly Lys Val Ala Ala
            100                 105                 110

Gly Trp Asp Pro Asp Leu Pro Leu Ile Arg Leu Glu Ala Asp Asp Gly
        115                 120                 125

Ser Ile Thr Ala Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Cys Leu Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ala Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Thr Ser Ser Leu Trp Ile Gly Asn
            340                 345                 350

Arg Tyr Trp Ser Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380
```

-continued

Thr Pro Arg Phe Arg Pro Ile Ser Val Thr Ile Thr Glu Gln Asn Gly
385 390 395 400

Ala Lys Leu Gly Ile Gly Val Ala Thr Asp Tyr Ile Val Pro Gly Ile
405 410 415

Pro Asp Gly Trp Pro Asp Thr Thr Ile Pro Gly Glu Leu Ile Pro Ala
420 425 430

Gly Asp Tyr Ala Ile Thr Asn Gly Thr Gly Asn Asp Ile Thr Thr Ala
435 440 445

Thr Gly Tyr Asp Thr Ala Asp Ile Ile Lys Asn Asn Thr Asn Phe Arg
450 455 460

Gly Met Tyr Ile Cys Gly Ser Leu Gln Arg Ala Trp Gly Asp Lys Lys
465 470 475 480

Ile Ser Asn Thr Ala Phe Ile Thr Thr Ala Thr Leu Asp Gly Asp Asn
485 490 495

Asn Asn Lys Ile Asn Pro Cys Asn Thr Ile Asp Gln Ser Lys Ile Val
500 505 510

Val Phe Gln Asp Asn His Val Gly Lys Lys Ala Gln Thr Ser Asp Asp
515 520 525

Thr Leu Ala Leu Leu Gly Tyr Thr Gly Ile Gly Glu Gln Ala Ile Gly
530 535 540

Ser Asp Arg Asp Arg Val Val Arg Ile Ser Thr Leu Pro Glu Thr Gly
545 550 555 560

Ala Arg Gly Gly Asn His Pro Ile Phe Tyr Lys Asn Ser Ile Lys Leu
565 570 575

Gly Tyr Val Ile Arg Ser Ile Asp Val Phe Asn Ser Gln Ile Leu His
580 585 590

Thr Ser Arg Gln Leu Ser Leu Asn His Tyr Leu Leu Pro Pro Asp Ser
595 600 605

Phe Ala Val Tyr Arg Ile Ile Asp Ser Asn Gly Ser Trp Phe Asp Ile
610 615 620

Gly Ile Asp Ser Asp Gly Phe Ser Phe Val Gly Val Ser Gly Phe Gly
625 630 635 640

Lys Leu Glu Phe Pro Leu Ser Ala Ser Tyr Met Gly Ile Gln Leu Ala
645 650 655

Lys Ile Arg Leu Ala Ser Asn Ile Arg Ser Pro Met Thr Lys Leu
660 665 670

<210> SEQ ID NO 36
<211> LENGTH: 668
<212> TYPE: PRT
<213> ORGANISM: Feline calicivirus

<400> SEQUENCE: 36

Met Cys Ser Thr Cys Ala Asn Val Leu Lys Tyr Tyr Asp Trp Asp Pro
1 5 10 15

His Phe Lys Leu Ile Ile Asn Pro Asn Lys Phe Leu Ser Val Gly Phe
20 25 30

Cys Asp Asn Pro Leu Met Cys Cys Tyr Pro Glu Leu Leu Pro Glu Phe
35 40 45

Gly Thr Val Trp Asn Cys Asn Gln Ser Pro Leu Gln Ile Tyr Leu Glu
50 55 60

Ser Ile Leu Gly Asp Asp Glu Trp Val Ser Thr Tyr Glu Ala Ile Asp
65 70 75 80

Pro Val Val Pro Pro Met His Trp Asn Glu Ala Gly Lys Leu Phe Gln
85 90 95

-continued

```
Pro His Pro Gly Ile Leu Met His His Ile Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Pro Val Gly Gly Val Ile Ala
    130                 135                 140

Glu Pro Ser Ala Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Ser His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Ile Val Pro Pro Gly Ile
225                 230                 235                 240

Glu Pro Val Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Asn Leu Tyr His Leu Met Ser Asp Thr Asp Thr Thr Ser Leu Val
        275                 280                 285

Ile Met Ile Tyr Asn Asp Leu Ile Asn Pro Tyr Ala Asn Asp Ser Asn
    290                 295                 300

Ser Ser Gly Cys Ile Val Thr Val Glu Thr Lys Pro Gly Ala Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Ser Ser Ser Leu Trp Ile Gly Asn
            340                 345                 350

Arg His Trp Thr Asp Ile Thr Glu Phe Val Val Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Val Thr Val Ser Glu Lys Gly Gly
385                 390                 395                 400

Ser Lys Leu Gly Ile Gly Val Ala Thr Asp Ser Ile Val Pro Gly Ile
                405                 410                 415

Pro Asp Gly Trp Pro Asp Thr Ser Ile Ser Asp Thr Leu Ile Pro Ser
            420                 425                 430

Gly Asp Tyr Ala Ile Thr Ser Gly Asn Gly Asn Asp Ile Ile Thr Gly
        435                 440                 445

Ala Asp Tyr Asp Ser Ala Asp Val Ile Lys Asn Asn Thr Asn Phe Arg
    450                 455                 460

Ser Met Tyr Ile Cys Gly Ser Leu Gln Arg Ala Trp Gly Asp Lys Lys
465                 470                 475                 480

Val Ser Glu Thr Ala Phe Ile Thr Thr Ala Val Arg Asn Glu Asn Ser
                485                 490                 495

Ile Ser Pro Ser Asn Val Ile Asp Ala Thr Lys Leu Ile Val Tyr Gln
            500                 505                 510
```

```
Asp Ala His Val Glu Thr Asp Val Gln Thr Ser Asp Val Thr Leu Ala
        515                 520                 525

Ile Leu Gly Tyr Thr Gly Ile Gly Glu Glu Ala Ile Gly Leu Asp Arg
    530                 535                 540

Asp Lys Val Val Arg Ile Ser Ile Leu Pro Glu Thr Gly Thr Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Met Asn Ser Gln Ile Leu His Thr Ser Arg
            580                 585                 590

Gln Leu Ser Leu Asn Asn Tyr Ser Leu Pro Pro Asp Ser Phe Ala Val
        595                 600                 605

Tyr Arg Ile Ile Asp Ser Ala Gly Ser Trp Phe Asp Ile Gly Ile Asp
    610                 615                 620

Ser Asp Gly Phe Ser Phe Val Gly Ile Ser Asn Val Gly Lys Leu Ile
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Ala Met Thr Lys Leu
            660                 665


<210> SEQ ID NO 37
<211> LENGTH: 669
<212> TYPE: PRT
<213> ORGANISM: Feline calicivirus

<400> SEQUENCE: 37

Met Cys Ser Thr Cys Ala Asn Val Leu Lys Tyr Tyr Asp Trp Asp Pro
1               5                   10                  15

His Phe Arg Leu Thr Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asn Gln Ser Pro Leu Glu Ile Tyr Leu Glu
    50                  55                  60

Ser Ile Leu Gly Asp Asp Glu Trp Ala Ser Thr Tyr Glu Ala Ile Asp
65                  70                  75                  80

Pro Val Val Pro Pro Met His Trp Asp Cys Ala Gly Lys Ile Phe Gln
                85                  90                  95

Pro His Pro Gly Val Leu Met His His Leu Ile Ser Glu Val Ala Lys
            100                 105                 110

Gly Trp Asp Pro Asn Leu Pro Ser Phe Arg Leu Glu Ala Asp Asp Gly
        115                 120                 125

Ser Ile Thr Thr Pro Glu Gln Gly Thr Pro Val Gly Gly Val Ile Ala
    130                 135                 140

Glu Pro Ser Ala Gln Met Ser Thr Ala Ala Asp Met Ala Ser Gly Lys
145                 150                 155                 160

Ser Val Asp Ser Glu Trp Gly Lys Ala Phe Phe Ser Phe His Thr Ser
                165                 170                 175

Val Asn Trp Ser Thr Ser Glu Thr Gln Gly Lys Ile Leu Phe Lys Gln
            180                 185                 190

Ser Leu Gly Pro Leu Leu Asn Pro Tyr Leu Glu His Leu Ala Lys Leu
        195                 200                 205

Tyr Val Ala Trp Ser Gly Ser Val Glu Val Arg Phe Ser Ile Ser Gly
    210                 215                 220
```

-continued

```
Ser Gly Val Phe Gly Gly Lys Leu Ala Ala Ile Val Val Pro Pro Gly
225                 230                 235                 240

Val Asp Pro Val Gln Ser Thr Ser Met Leu Gln Tyr Pro His Val Leu
                245                 250                 255

Phe Asp Ala Arg Gln Val Glu Pro Val Ile Phe Thr Ile Pro Asp Leu
            260                 265                 270

Arg Asn Ser Leu Tyr His Leu Met Ser Asp Thr Asp Thr Thr Ser Leu
        275                 280                 285

Val Ile Met Val Tyr Asn Asp Leu Ile Asn Pro Tyr Ala Ser Asp Ser
    290                 295                 300

Asn Ser Ser Gly Cys Ile Val Thr Val Glu Thr Lys Pro Gly Pro Asp
305                 310                 315                 320

Phe Lys Phe His Leu Leu Lys Pro Pro Gly Ser Met Leu Thr His Gly
                325                 330                 335

Ser Val Pro Ser Asp Leu Ile Pro Lys Ser Ser Ser Leu Trp Ile Gly
            340                 345                 350

Asn Arg Tyr Trp Ser Asp Ile Thr Asp Phe Val Ile Arg Pro Phe Val
        355                 360                 365

Phe Gln Ala Asn Arg His Phe Asp Phe Asn Gln Glu Thr Ala Gly Trp
    370                 375                 380

Ser Thr Pro Arg Phe Arg Pro Leu Thr Ile Thr Ile Ser Val Glu Gly
385                 390                 395                 400

Gly Ala Lys Leu Gly Thr Gly Val Ala Thr Asp Tyr Ile Val Pro Gly
                405                 410                 415

Ile Pro Asp Gly Trp Pro Asp Thr Thr Ile Pro Glu Lys Leu Thr Pro
            420                 425                 430

Ala Gly Asp Tyr Ala Ile Thr Asp Gly Asn Gly Ser Asp Ile Val Thr
        435                 440                 445

Ala Ala Lys Tyr Asp Thr Ala Asp Val Ile Lys Asn Asn Thr Asn Phe
    450                 455                 460

Lys Gly Met Tyr Ile Cys Gly Ser Leu Gln Arg Ala Trp Gly Asp Lys
465                 470                 475                 480

Lys Ile Ser Asn Thr Ala Phe Ile Thr Thr Gly Thr Val Glu Asn Asn
                485                 490                 495

Ser Ile Glu Pro Ser Asn Thr Ile Asp Ala Thr Lys Leu Ala Val Phe
            500                 505                 510

Gln Asp Thr His Val Gly His Glu Val Gln Thr Ser Asp Asp Thr Leu
        515                 520                 525

Ala Leu Leu Gly Tyr Thr Gly Ile Gly Glu Gln Ala Ile Gly Ser Asp
    530                 535                 540

Arg Asp Arg Val Val Arg Ile Ser Val Leu Pro Glu Thr Gly Ala Arg
545                 550                 555                 560

Gly Gly Asn His Pro Ile Phe Tyr Lys Asn Ser Ile Lys Leu Gly Tyr
                565                 570                 575

Val Ile Arg Ser Ile Asp Val Phe Asn Ser Gln Ile Leu His Thr Ser
            580                 585                 590

Arg Gln Leu Ser Leu Asn His Tyr Leu Leu Pro Pro Asp Ser Phe Ala
        595                 600                 605

Val Tyr Arg Ile Ile Asp Ser Asn Gly Ser Trp Phe Asp Ile Gly Ile
    610                 615                 620

Asp Ser Asp Gly Phe Ser Phe Val Gly Val Ser Ser Ile Thr Lys Leu
625                 630                 635                 640
```

```
Glu Phe Pro Leu Thr Ala Ser Tyr Met Gly Ile Gln Leu Ala Lys Ile
                645                 650                 655

Arg Leu Ala Ser Asn Ile Arg Gly Gln Met Thr Lys Ile
            660                 665


<210> SEQ ID NO 38
<211> LENGTH: 669
<212> TYPE: PRT
<213> ORGANISM: Feline calicivirus

<400> SEQUENCE: 38

Met Cys Ser Thr Cys Ala Asn Val Leu Lys Tyr Tyr Asp Trp Asp Pro
1               5                   10                  15

His Phe Arg Leu Thr Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Glu Ile Tyr Leu Glu
    50                  55                  60

Ser Ile Leu Gly Asp Asp Glu Trp Ala Ser Thr Tyr Glu Ala Ile Asp
65                  70                  75                  80

Pro Val Val Pro Pro Met His Trp Asp Cys Ala Gly Lys Ile Phe Gln
                85                  90                  95

Pro His Pro Gly Val Leu Met His His Leu Ile Ser Glu Val Ala Lys
            100                 105                 110

Gly Trp Asp Pro Asn Leu Pro Ser Phe Arg Leu Glu Ala Asp Asp Gly
        115                 120                 125

Ser Ile Thr Thr Pro Glu Gln Gly Thr Pro Val Gly Gly Val Ile Ala
    130                 135                 140

Glu Pro Ser Ala Gln Met Ser Thr Ala Ala Asp Met Ala Ser Gly Lys
145                 150                 155                 160

Ser Val Asp Ser Glu Trp Gly Lys Ala Phe Phe Ser Phe His Thr Ser
                165                 170                 175

Val Asn Trp Ser Thr Ser Glu Thr Gln Gly Lys Ile Leu Phe Lys Gln
            180                 185                 190

Ser Leu Gly Pro Leu Leu Asn Pro Tyr Leu Glu His Leu Ala Lys Leu
        195                 200                 205

Tyr Val Ala Trp Ser Gly Ser Val Glu Val Arg Phe Ser Ile Ser Gly
    210                 215                 220

Ser Gly Val Phe Gly Gly Lys Leu Ala Ala Ile Val Val Pro Pro Gly
225                 230                 235                 240

Val Asp Pro Val Gln Ser Thr Ser Met Leu Gln Tyr Pro His Val Leu
                245                 250                 255

Phe Asp Ala Arg Gln Val Glu Pro Val Ile Phe Thr Ile Pro Asp Leu
            260                 265                 270

Arg Asn Ser Leu Tyr His Leu Met Ser Asp Thr Asp Thr Thr Ser Leu
        275                 280                 285

Val Ile Met Val Tyr Asn Asp Leu Ile Asn Pro Tyr Ala Ser Asp Ser
    290                 295                 300

Asn Ser Ser Gly Cys Ile Val Thr Val Glu Thr Lys Pro Gly Pro Asp
305                 310                 315                 320

Phe Lys Phe His Leu Leu Lys Pro Pro Gly Ser Met Leu Thr His Gly
                325                 330                 335

Ser Val Pro Ser Asp Leu Ile Pro Lys Ser Ser Ser Leu Trp Ile Gly
            340                 345                 350
```

-continued

```
Ile Cys Leu Trp Arg Gly Ile Thr Asp Phe Val Ile Arg Pro Phe Val
        355                 360                 365

Phe Gln Val Asn Arg His Phe Asp Phe Asn Gln Glu Thr Ala Gly Trp
    370                 375                 380

Ser Thr Pro Arg Phe Arg Pro Leu Thr Ile Thr Ile Ser Val Lys Glu
385                 390                 395                 400

Gly Ala Asn Ser Glu Leu Gly Val Ala Thr Asp Tyr Ile Val Pro Gly
                405                 410                 415

Ile Pro Asp Gly Trp Pro Asp Thr Thr Ile Pro Glu Lys Leu Thr Pro
            420                 425                 430

Ala Gly Asp Tyr Ala Ile Thr Asp Ser Ser Gly Ser Asp Ile Thr Thr
        435                 440                 445

Ala Ala Lys Tyr Asp Ala Ala Asp Val Ile Glu Asn Asn Thr Asn Phe
    450                 455                 460

Lys Gly Met Tyr Ile Cys Gly Ser Leu Gln Arg Ala Trp Gly Asp Lys
465                 470                 475                 480

Lys Ile Ser Asn Thr Ala Phe Ile Thr Thr Gly Thr Val Glu Asp Asn
                485                 490                 495

Phe Ile Glu Pro Ser Asn Thr Ile Asp Ala Thr Lys Leu Ala Val Phe
            500                 505                 510

Gln Asp Thr His Val Gly Arg Glu Val Gln Thr Ser Asp Asp Thr Leu
        515                 520                 525

Ala Leu Leu Gly Tyr Thr Gly Ile Gly Glu Gln Ala Ile Gly Ser Asp
    530                 535                 540

Arg Asp Arg Val Val Arg Ile Ser Val Leu Pro Glu Thr Gly Ala Arg
545                 550                 555                 560

Gly Gly Asn His Pro Ile Phe Tyr Lys Asn Ser Ile Lys Leu Gly Tyr
                565                 570                 575

Val Val Arg Ser Ile Asp Val Phe Asn Ser Gln Ile Leu His Thr Ser
            580                 585                 590

Arg Gln Leu Ser Leu Asn His Tyr Leu Leu Pro Pro Asp Ser Phe Ala
        595                 600                 605

Val Tyr Arg Ile Ile Asp Ser Asn Gly Ser Trp Phe Asp Ile Gly Ile
    610                 615                 620

Asp Ser Asp Gly Phe Ser Phe Val Gly Val Ser Ser Ile Thr Lys Leu
625                 630                 635                 640

Glu Phe Pro Leu Thr Ala Ser Tyr Met Gly Ile Gln Leu Ala Lys Ile
                645                 650                 655

Arg Leu Ala Ser Asn Ile Arg Ser Gln Met Thr Lys Ile
            660                 665


<210> SEQ ID NO 39
<211> LENGTH: 668
<212> TYPE: PRT
<213> ORGANISM: Feline calicivirus

<400> SEQUENCE: 39

Met Cys Ser Thr Cys Ala Asn Val Leu Lys Tyr Tyr Asn Trp Asp Pro
1               5                   10                  15

His Phe Lys Leu Val Ile Asn Pro Asn Lys Phe Leu Pro Ile Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
```

```
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Asp Lys Ala Gly Lys Ile Phe Gln
                85                  90                  95

Pro His Pro Gly Val Leu Met His Tyr Ile Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Val Val Gly Gly Val Ile Ala
    130                 135                 140

Glu Pro Ser Ser Gln Met Ser Thr Ala Ala Asp Met Ala Ser Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Ile Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Thr Leu Tyr His Leu Met Ser Asp Thr Asp Thr Thr Ser Leu Val
        275                 280                 285

Val Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Ser Asp Phe
305                 310                 315                 320

Lys Phe His Leu Leu Lys Pro Pro Gly Ser Val Leu Thr His Gly Ser
                325                 330                 335

Val Pro Ser Asp Leu Ile Pro Arg Thr Ser Ser Leu Trp Ile Gly Asn
            340                 345                 350

Arg Phe Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Val Thr Ile Ser Glu Lys Asp Gly
385                 390                 395                 400

Ala Lys Leu Gly Ile Gly Val Ala Thr Asp Phe Ile Val Pro Gly Ile
                405                 410                 415

Pro Asp Gly Trp Pro Asp Thr Thr Ile Gly Glu Arg Leu Val Pro Val
            420                 425                 430

Gly Asp Tyr Ala Ile Thr Asn Ser Ala Gly Ile Asp Ile Thr Thr Ala
        435                 440                 445

Ser Gln Tyr Asp Thr Ala Gly Val Ile Lys Asn Asn Thr Asn Phe Arg
    450                 455                 460

Gly Met Tyr Ile Cys Gly Ser Leu Gln Arg Ala Trp Gly Asp Lys Lys
465                 470                 475                 480
```

```
Ile Ser Asn Thr Ala Phe Ile Thr Thr Ala Thr Val Asn Arg Asn Asp
                485                 490                 495

Leu Ile Pro Ser Asn Val Ile Asp Gln Thr Lys Ile Ala Ile Phe Gln
            500                 505                 510

Asp Asn His Val Gly Val Asp Val Gln Thr Ser Asp Asp Thr Leu Ala
        515                 520                 525

Leu Leu Gly Tyr Thr Gly Ile Gly Glu Glu Ala Ile Gly Ala Asp Arg
    530                 535                 540

Glu Arg Val Val Arg Ile Ser Thr Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Val Arg Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Ile Asp Ser Asn Gly Ser Trp Phe Asp Ile Gly Ile Asp
    610                 615                 620

Thr Asp Gly Phe Ser Phe Val Gly Val Ser Asn Ile Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Thr Met Ile Lys Leu
            660                 665


<210> SEQ ID NO 40
<211> LENGTH: 668
<212> TYPE: PRT
<213> ORGANISM: Feline calicivirus

<400> SEQUENCE: 40

Met Cys Ser Thr Cys Ala Asn Val Leu Lys Tyr Tyr Asp Trp Asp Pro
1               5                   10                  15

His Ile Arg Leu Val Ile Asp Pro Asn Arg Phe Leu Ser Val Ser Phe
            20                  25                  30

Cys Asp Lys Pro Leu Leu Cys Cys Tyr Pro Asp Leu Leu Pro Glu Phe
        35                  40                  45

Gly Thr Val Trp Asp Cys Asn Gln Ser Pro Leu Glu Ile Tyr Leu Glu
    50                  55                  60

Ser Ile Leu Gly Asp Asp Glu Trp Ser Ser Thr Phe Glu Ala Ile Asp
65                  70                  75                  80

Pro Val Val Pro Pro Met His Trp Asp Glu Ala Gly Lys Ile Phe Gln
                85                  90                  95

Pro His Pro Gly Val Leu Met His His Leu Ile Asn Gln Val Ala Lys
            100                 105                 110

Ala Trp Asp Pro Asn Leu Pro Leu Phe Arg Leu Glu Ala Asp Asp Gly
        115                 120                 125

Ser Ile Thr Ser Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
```

-continued

```
            180                 185                 190

Leu Gly Pro Leu Leu Asn Pro Tyr Leu Glu His Leu Ala Lys Leu Tyr
        195                 200                 205

Val Ala Trp Ser Gly Ser Val Asp Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asn Pro Val Gln Ser Thr Ser Met Leu Gln Tyr Pro His Val Leu Phe
            245                 250                 255

Asp Ala Arg Gln Val Glu Pro Val Ile Phe Ser Ile Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Ser Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
            325                 330                 335

Val Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Thr Ile Ser Glu Lys Asp Gly
385                 390                 395                 400

Ser Lys Leu Gly Ile Gly Val Ala Met Asp Ser Ile Val Pro Gly Ile
            405                 410                 415

Pro Asp Gly Trp Pro Asp Thr Thr Ile Pro Glu Lys Leu Val Pro Ala
            420                 425                 430

Gly Asn Tyr Ala Ile Ala Asn Gly Thr Gly Asn Asp Ile Thr Thr Ala
        435                 440                 445

Lys Asp Tyr Asp Ser Ala Thr Val Ile Gln Asn Asn Thr Asn Phe Lys
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Thr Arg Ser Asp Asn Thr
            485                 490                 495

Ile Thr Pro Ser Asn Val Ile Asp Pro Thr Lys Ile Ala Val Tyr Gln
            500                 505                 510

Asp Thr His Val Gly Ala Glu Val Gln Thr Ser Asp Asp Thr Leu Ala
        515                 520                 525

Ile Leu Gly Tyr Thr Gly Ile Gly Glu Glu Ala Ile Gly Ala Asp Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
            565                 570                 575

Ile Arg Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605
```

```
Tyr Arg Ile Thr Asp Ser Asn Gly Ser Trp Phe Asp Ile Gly Ile Asp
    610                 615                 620

Ser Asp Gly Phe Ser Phe Val Gly Ala Ser Asn Val Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Ser Met Thr Lys Leu
            660                 665


<210> SEQ ID NO 41
<211> LENGTH: 668
<212> TYPE: PRT
<213> ORGANISM: Feline calicivirus

<400> SEQUENCE: 41

Met Cys Ser Thr Cys Ala Asn Val Leu Lys Tyr Tyr Gly Trp Asp Pro
1               5                   10                  15

His Phe Arg Leu Val Val Asn Pro Asn Lys Phe Leu Ser Val Gly Phe
            20                  25                  30

Cys Asp Asn Pro Leu Met Cys Cys Tyr Pro Asp Leu Leu Pro Glu Phe
        35                  40                  45

Gly Thr Leu Trp Asp Cys Asp Gln Ser Pro Leu Gln Ile Tyr Leu Glu
    50                  55                  60

Ser Ile Leu Gly Asp Asp Glu Trp Ala Ser Thr Tyr Glu Ala Ile Asp
65                  70                  75                  80

Pro Ser Val Pro Pro Met His Trp Asp Ala Met Gly Lys Ile Phe Gln
                85                  90                  95

Pro His Pro Gly Val Leu Met His His Ile Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Ala Pro Glu Gln Gly Thr Val Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Thr Glu Thr Gln Gly Lys Ile Leu Phe Lys Gln Ser
            180                 185                 190

Leu Gly Pro Leu Leu Asn Pro Tyr Leu Glu His Leu Ala Lys Leu Tyr
        195                 200                 205

Val Ala Trp Ser Gly Ser Ile Asp Val Arg Phe Ser Ile Ser Gly Ser
    210                 215                 220

Gly Val Tyr Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Thr Leu Tyr His Leu Ile Ser Asp Thr Asp Thr Thr Ser Leu Val
        275                 280                 285

Ile Met Val Tyr Asn Asp Leu Ile Asn Pro Tyr Ala Ser Asp Thr Asn
    290                 295                 300

Ser Ser Gly Cys Ile Val Thr Val Glu Thr Lys Pro Gly Pro Asp Phe
```

-continued

```
305                 310                 315                 320

Lys Phe His Leu Leu Lys Pro Pro Gly Ser Met Leu Thr His Gly Ser
                325                 330                 335

Ile Pro Ala Asp Leu Ile Pro Lys Ser Ser Ser Leu Trp Ile Gly Asn
            340                 345                 350

Arg Tyr Trp Ser Asp Ile Thr Glu Phe Val Val Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Val Thr Val Ser Glu Ser Gly Gly
385                 390                 395                 400

Ser Lys Leu Gly Ile Gly Val Ala Thr Asp Tyr Ile Val Pro Gly Ile
                405                 410                 415

Pro Asp Gly Trp Pro Asp Thr Thr Ile Pro Glu Lys Leu Thr Pro Ala
            420                 425                 430

Gly Asn Tyr Ala Ile Thr Thr Ser Asn Asn Ser Asp Ile Ala Thr Ala
        435                 440                 445

Thr Glu Tyr Asp His Ala Asp Glu Ile Lys Asn Asn Thr Asn Phe Lys
    450                 455                 460

Ser Met Tyr Ile Cys Gly Ser Leu Gln Arg Ala Trp Gly Asp Lys Lys
465                 470                 475                 480

Ile Ser Asn Thr Ala Phe Ile Thr Thr Ala Val Lys Glu Gly Asn Ser
                485                 490                 495

Ile Thr Pro Ser Asn Thr Ile Asp Met Thr Lys Leu Val Val Tyr Gln
            500                 505                 510

Asp Ala His Val Gly Asn Asp Val Gln Thr Ser Asp Val Thr Leu Ala
        515                 520                 525

Leu Leu Gly Tyr Thr Gly Ile Gly Glu Gln Ala Ile Gly Ser Asp Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Thr Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Pro Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Asp Gly Phe Ser Phe Val Gly Val Ser Ser Leu Pro Thr Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Ser Met Thr Lys Leu
            660                 665


<210> SEQ ID NO 42
<211> LENGTH: 668
<212> TYPE: PRT
<213> ORGANISM: Feline calicivirus

<400> SEQUENCE: 42

Met Cys Ser Thr Cys Ala Asn Val Leu Lys Tyr Tyr Asp Trp Asp Pro
1               5                   10                  15
```

```
His Phe Arg Leu Ile Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Glu Ile Phe Leu Glu
    50                  55                  60

Ser Ile Leu Gly Asp Asp Glu Trp Ala Ser Thr Tyr Glu Ala Ile Asp
65                  70                  75                  80

Pro Val Val Pro Pro Met His Trp Asp Ser Ala Gly Lys Ile Phe Gln
                85                  90                  95

Pro His Pro Gly Val Leu Met His His Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Ser Val Gly Gly Val Ile Ala
    130                 135                 140

Glu Pro Ser Ala Gln Met Ser Thr Ala Ala Asp Met Ala Thr Gly Lys
145                 150                 155                 160

Thr Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Thr His Leu Ala Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Thr Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Ser Leu Trp Ile Gly Asn
            340                 345                 350

Arg Tyr Trp Ser Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Thr Ile Ser Val Lys Glu Ser
385                 390                 395                 400

Ala Lys Leu Gly Thr Gly Val Ala Thr Asp Tyr Ile Val Pro Gly Ile
                405                 410                 415

Pro Asp Gly Trp Pro Asp Thr Thr Ile Pro Glu Glu Leu Thr Pro Ala
            420                 425                 430

Gly Asp Tyr Ala Ile Thr Asn Ser Ser Gly Asn Asp Ile Thr Thr Ala
```

```
        435                 440                 445

Ala Gly Phe Asp Ala Ala Asp Val Ile Lys Asn Asn Thr Asn Phe Arg
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Gly Thr Val Glu Gly Gly Lys
                485                 490                 495

Ile Arg Pro Ser Asn Val Ile Asp Gln Thr Lys Ile Ala Val Phe Gln
            500                 505                 510

Asp Thr His Ala Asn Arg Glu Val Gln Thr Ser Asp Asp Thr Leu Ala
        515                 520                 525

Leu Leu Gly Tyr Thr Gly Ile Gly Glu Glu Ala Ile Gly Ala Asp Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Leu Ala Val
        595                 600                 605

Tyr Arg Ile Thr Asp Ser Asn Gly Ser Trp Phe Asp Ile Gly Ile Asp
    610                 615                 620

Ser Asp Gly Phe Ser Phe Val Gly Val Ser Asn Ile Gly Lys Leu Glu
625                 630                 635                 640

Phe Pro Leu Thr Ala Ser Tyr Met Gly Ile Gln Leu Ala Lys Val Arg
                645                 650                 655

Leu Ala Ser Asn Ile Arg Ser Ser Met Thr Lys Leu
            660                 665


<210> SEQ ID NO 43
<211> LENGTH: 668
<212> TYPE: PRT
<213> ORGANISM: Feline calicivirus

<400> SEQUENCE: 43

Met Cys Ser Thr Cys Ala Asn Val Leu Lys Tyr Tyr Asp Trp Asp Pro
1               5                   10                  15

His Phe Lys Leu Val Ile Asn Pro Asn Lys Phe Leu Pro Ile Gly Phe
            20                  25                  30

Cys Asp Asn Pro Leu Leu Cys Cys Tyr Pro Glu Leu Leu Pro Glu Phe
        35                  40                  45

Gly Thr Val Trp Asp Cys Gly Gln Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Asp Glu Ala Gly Lys Ile Phe Gln
                85                  90                  95

Pro His Pro Gly Val Leu Met Asn Tyr Ile Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Ala Pro Glu Gln Gly Thr Val Val Gly Gly Val Ile Ala
    130                 135                 140
```

-continued

```
Glu Pro Ser Ser Gln Met Ser Thr Ala Ala Asp Met Ala Ser Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Ile Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Asn Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Arg Thr Ser Ser Leu Trp Val Gly Asn
            340                 345                 350

Arg Phe Trp Gly Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Gln Phe Arg Pro Ile Thr Val Thr Ile Ser Val Lys Asn Gly
385                 390                 395                 400

Glu Lys Leu Gly Ile Gly Ile Ala Thr Asp Phe Ile Val Pro Gly Ile
                405                 410                 415

Pro Asp Gly Trp Pro Asp Thr Thr Ile Gly Glu Glu Leu Val Pro Ala
            420                 425                 430

Gly Asp Tyr Ala Ile Thr Thr Ser Ser Gly Asn Asp Ile Thr Thr Ala
        435                 440                 445

Gln Gln Tyr Asp Ala Ala Asp Ile Ile Asn Asn Asn Thr Asn Phe Lys
    450                 455                 460

Ser Met Tyr Ile Cys Gly Ser Leu Gln Arg Ala Trp Gly Asp Lys Lys
465                 470                 475                 480

Ile Ser Asn Thr Ala Phe Ile Thr Thr Ala Thr Val Ser Gly Asn Lys
                485                 490                 495

Leu Ile Pro Ser Asn Val Ile Asp Gln Thr Lys Ile Ala Ile Phe Gln
            500                 505                 510

Asp Thr His Ala Asn Gln Gly Val Gln Thr Ser Asp Asp Thr Leu Ala
        515                 520                 525

Ile Leu Gly Tyr Thr Gly Ile Gly Glu Glu Ala Ile Gly Ala Asn Arg
    530                 535                 540

Glu Arg Val Val Arg Ile Ser Thr Leu Pro Glu Ala Gly Ala Arg Gly
545                 550                 555                 560

Gly Asn His Pro Ile Phe Tyr Lys Asn Thr Met Lys Leu Gly Tyr Val
```

```
                565                 570                 575

Ile Arg Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Thr Asp Ser Asn Gly Ser Trp Phe Asp Ile Gly Ile Asp
    610                 615                 620

Thr Asp Gly Phe Ser Phe Val Gly Val Ser Ser Ile Gly Asn Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Thr Met Thr Lys Leu
            660                 665


<210> SEQ ID NO 44
<211> LENGTH: 668
<212> TYPE: PRT
<213> ORGANISM: Feline calicivirus

<400> SEQUENCE: 44

Met Cys Ser Thr Cys Ala Asn Val Leu Lys Tyr Tyr Asp Trp Asp Pro
1               5                   10                  15

His Ile Gln Leu Val Ile Asn Pro Asn Lys Phe Leu Pro Val Gly Phe
            20                  25                  30

Cys Asp Asn Pro Leu Met Cys Cys Phe Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ala Ser Thr Phe Glu Ala Val Glu
65                  70                  75                  80

Pro Ser Val Pro Pro Met His Trp Asp Glu Ala Gly Lys Ile Phe Gln
                85                  90                  95

Pro His Pro Gly Val Leu Met His His Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Thr His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Ile
225                 230                 235                 240

Asp Pro Val Gln Ser Thr Ser Met Leu Gln Tyr Pro His Val Leu Phe
                245                 250                 255

Asp Ala Arg Gln Val Asp Pro Val Ile Phe Thr Ile Pro Asp Leu Arg
            260                 265                 270
```

```
Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Ser Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Thr Ile Ser Val Asn Asn Ala
385                 390                 395                 400

Ala Lys Leu Gly Thr Gly Val Ala Thr Asp Tyr Ile Val Pro Gly Ile
                405                 410                 415

Pro Asp Gly Trp Pro Asp Thr Thr Ile Pro Ser Glu Leu Thr Pro Ala
            420                 425                 430

Gly Asp Tyr Ala Ile Thr Asn Ser Ser Gly Asn Asp Ile Thr Thr Ala
        435                 440                 445

Val Gly Tyr Asp Thr Ala Asp Glu Ile Lys Asn Asn Thr Asn Phe Arg
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Gly Ile Val Thr Gly Asn Lys
                485                 490                 495

Leu Gln Pro Ser Asn Thr Ile Asp Gln Thr Lys Ile Ala Val Phe Gln
            500                 505                 510

Asp Thr His Ala Asn Lys Asp Pro Gln Thr Ser Asp Asp Thr Leu Ala
        515                 520                 525

Leu Leu Gly Tyr Thr Gly Ile Gly Glu Glu Ala Ile Gly Ala Asp Arg
    530                 535                 540

Asp Arg Val Val Arg Ile Ser Val Leu Pro Glu Ala Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Glu Gly Phe Ser Phe Val Gly Val Ser Ser Ile Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Thr Leu Thr Lys Leu
            660                 665
```

<210> SEQ ID NO 45
<211> LENGTH: 667
<212> TYPE: PRT

<213> ORGANISM: Feline calicivirus

<400> SEQUENCE: 45

```
Met Cys Ser Thr Cys Ala Asn Val Leu Lys Tyr Tyr Asp Trp Asp Pro
1               5                   10                  15

His Phe Arg Leu Ile Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Glu Ile Tyr Leu Glu
    50                  55                  60

Ser Ile Leu Gly Asp Asp Glu Trp Ala Ser Thr Tyr Glu Ala Ile Asp
65                  70                  75                  80

Pro Val Val Pro Pro Met His Trp Asp Ser Ala Gly Lys Ile Phe Gln
                85                  90                  95

Pro His Pro Gly Val Leu Met His His Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Ser Val Gly Gly Val Ile Ala
    130                 135                 140

Glu Pro Ser Ala Gln Met Ser Thr Ala Ala Asp Met Ala Thr Gly Lys
145                 150                 155                 160

Thr Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Thr His Leu Ala Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Gly Val Asp
225                 230                 235                 240

Pro Val Gln Ser Thr Ser Met Leu Gln Tyr Pro His Val Leu Phe Asp
                245                 250                 255

Ala Arg Gln Val Glu Pro Val Ile Phe Thr Ile Pro Asp Leu Arg Ser
            260                 265                 270

Thr Leu Tyr His Leu Met Ser Asp Thr Asp Thr Thr Ser Leu Val Ile
        275                 280                 285

Met Val Tyr Asn Asp Leu Ile Asn Pro Tyr Ala Asn Asp Thr Asn Ser
    290                 295                 300

Ser Gly Cys Ile Val Thr Val Glu Thr Lys Pro Gly Pro Asp Phe Lys
305                 310                 315                 320

Phe His Leu Leu Lys Pro Pro Gly Ser Met Leu Thr His Gly Ser Val
                325                 330                 335

Pro Ser Asp Leu Ile Pro Lys Ser Ser Ser Leu Trp Ile Gly Asn Arg
            340                 345                 350

Tyr Trp Ser Asp Ile Thr Asp Phe Val Ile Arg Pro Phe Val Phe Gln
        355                 360                 365

Ala Asn Arg His Phe Asp Phe Asn Gln Glu Thr Ala Gly Trp Ser Thr
    370                 375                 380

Pro Arg Phe Arg Pro Ile Thr Ile Thr Ile Ser Val Lys Glu Leu Ala
385                 390                 395                 400
```

```
Lys Leu Gly Thr Gly Val Ala Thr Asp Tyr Ile Val Pro Gly Ile Pro
                405                 410                 415

Asp Gly Trp Pro Asp Thr Thr Ile Pro Glu Glu Leu Thr Pro Ala Gly
            420                 425                 430

Asp Tyr Ala Ile Thr Asn Ser Ser Gly Asn Asp Ile Thr Thr Ala Ala
        435                 440                 445

Asp Phe Asp Ala Ala Asp Met Ile Lys Asn Asn Thr Asn Phe Arg Gly
    450                 455                 460

Met Tyr Ile Cys Gly Ser Leu Gln Arg Ala Trp Gly Asp Lys Lys Ile
465                 470                 475                 480

Ser Asn Thr Ala Phe Ile Thr Thr Gly Thr Val Glu Gly Gly Lys Ile
                485                 490                 495

Arg Pro Ser Asn Val Ile Asp Gln Thr Lys Ile Ala Val Phe Gln Asp
            500                 505                 510

Thr His Val Asn Gln Glu Val Gln Thr Ser Asp Asp Thr Leu Ala Leu
        515                 520                 525

Leu Gly Tyr Thr Gly Ile Gly Glu Glu Ala Ile Gly Ala Asp Arg Asp
    530                 535                 540

Arg Val Val Arg Ile Ser Val Leu Pro Glu Thr Gly Ala Arg Gly Gly
545                 550                 555                 560

Asn His Pro Ile Phe Tyr Lys Asn Ser Ile Lys Leu Gly Tyr Val Ile
                565                 570                 575

Arg Ser Ile Asp Val Phe Asn Ser Gln Ile Leu His Thr Ser Arg Gln
            580                 585                 590

Leu Ser Leu Asn His Tyr Leu Leu Ser Pro Asp Ser Leu Ala Val Tyr
        595                 600                 605

Arg Ile Thr Asp Ser Asn Gly Ser Trp Phe Asp Ile Gly Ile Asp Ser
    610                 615                 620

Asp Gly Phe Ser Phe Val Gly Val Ser Asn Ile Gly Lys Leu Glu Phe
625                 630                 635                 640

Pro Leu Thr Ala Ser Tyr Met Gly Ile Gln Leu Ala Lys Val Arg Leu
                645                 650                 655

Ala Ser Asn Ile Arg Ser Ser Met Thr Lys Leu
            660                 665


<210> SEQ ID NO 46
<211> LENGTH: 668
<212> TYPE: PRT
<213> ORGANISM: Feline calicivirus

<400> SEQUENCE: 46

Met Cys Ser Thr Cys Ala Asn Val Leu Lys Tyr Tyr Asp Trp Asp Pro
1               5                   10                  15

His Phe Lys Leu Val Ile Asn Pro Asn Lys Phe Leu Ala Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asn Gln Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Asp Glu Ala Gly Lys Ile Phe Gln
                85                  90                  95

Pro His Pro Gly Val Leu Met His His Leu Ile Gly Glu Val Ala Lys
            100                 105                 110
```

-continued

```
Ala Trp Asp Pro Asn Leu Pro Leu Phe Arg Leu Glu Ala Asp Asp Gly
        115                 120                 125

Ser Ile Thr Thr Pro Glu Gln Gly Thr Ser Val Gly Gly Val Ile Ala
    130                 135                 140

Glu Pro Ser Ala Gln Met Ala Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Thr Glu Thr Gln Gly Lys Ile Leu Phe Lys Gln Ser
            180                 185                 190

Leu Gly Pro Leu Leu Asn Pro Tyr Leu Glu His Leu Ala Ser Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Ile
225                 230                 235                 240

Asn Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Asn Ser Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Thr Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Ser Ser Ser Leu Trp Ile Gly Asn
            340                 345                 350

Arg Tyr Trp Ser Asp Ile Thr Asp Phe Ile Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Val Thr Ile Ser Gln Lys Glu Gly
385                 390                 395                 400

Glu Lys Leu Gly Ile Gly Val Ala Thr Asp Tyr Ile Val Pro Gly Ile
                405                 410                 415

Pro Asp Gly Trp Pro Asp Thr Thr Ile Pro Gly Lys Leu Thr Pro Val
            420                 425                 430

Gly Asn Tyr Ala Ile Thr Asp Glu Ser Gly Ser Asp Ile Val Thr Ala
        435                 440                 445

Ala Glu Phe Asp Ser Ala Thr Gly Ile Lys Asn Asn Thr Glu Phe Arg
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Lys Val Asn Asn Asn Met
                485                 490                 495

Leu Glu Pro Ser Asn Val Ile Asp Gln Thr Lys Ile Ala Ile Phe Gln
            500                 505                 510

Asp Asn His Val Gly Arg Asp Val Gln Thr Ser Asp Asp Thr Leu Ala
        515                 520                 525
```

-continued

```
Leu Leu Gly Tyr Thr Gly Ile Gly Glu Gln Ala Ile Gly Ser Asp Arg
    530                 535                 540

Asp Arg Val Val Arg Ile Ser Ile Leu Pro Glu Ala Gly Ala Arg Gly
545                 550                 555                 560

Gly Asn His Pro Ile Phe Tyr Lys Asn Ser Ile Lys Leu Gly Tyr Val
                565                 570                 575

Leu Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Asp Gly Phe Ser Phe Val Gly Val Ser Ala Ile Gly Lys Leu Glu
625                 630                 635                 640

Tyr Pro Leu Thr Ala Ser Tyr Met Gly Ile Gln Leu Ala Lys Val Arg
                645                 650                 655

Leu Ala Ser Asn Ile Arg Ser Ser Met Thr Lys Leu
            660                 665


<210> SEQ ID NO 47
<211> LENGTH: 669
<212> TYPE: PRT
<213> ORGANISM: Feline calicivirus

<400> SEQUENCE: 47

Met Cys Ser Thr Cys Ala Asn Val Leu Lys Tyr Tyr Asp Trp Asp Pro
1               5                   10                  15

His Phe Arg Leu Val Ile Asp Pro Asn Lys Phe Leu Ser Val Gly Phe
            20                  25                  30

Cys Asn Asn Pro Leu Met Cys Cys Tyr Pro Glu Leu Leu Pro Glu Phe
        35                  40                  45

Gly Thr Val Trp Asp Cys Asp Gln Ala Pro Leu Gln Ile Tyr Leu Glu
    50                  55                  60

Ser Ile Leu Gly Asp Asp Glu Trp Ser Ser Thr Phe Glu Ala Ile Asp
65                  70                  75                  80

Pro Val Val Pro Pro Met His Trp Asn Gly Ala Gly Lys Ile Phe Gln
                85                  90                  95

Pro His Pro Gly Ile Leu Thr His His Leu Leu Ser Glu Val Ala Lys
            100                 105                 110

Gly Trp Asp Pro Asn Leu Pro Leu Phe Arg Leu Glu Gly Asp Ser Asp
        115                 120                 125

Ser Ser Val Thr Thr Pro Glu Gln Gly Thr Met Val Gly Gly Val Ile
    130                 135                 140

Ala Glu Pro Ser Ala Gln Met Ser Thr Ala Ala Asp Met Ala Ser Gly
145                 150                 155                 160

Lys Ser Val Asp Ser Glu Trp Glu Ala Phe Phe Ser Phe His Thr Ser
                165                 170                 175

Val Asn Trp Ser Thr Ser Glu Thr Gln Gly Lys Ile Leu Phe Lys Gln
            180                 185                 190

Ser Leu Gly Pro Leu Leu Asn Pro Tyr Leu Glu His Leu Ala Lys Leu
        195                 200                 205

Tyr Val Ala Trp Ser Gly Ser Ile Glu Val Arg Phe Ser Ile Ser Gly
    210                 215                 220

Ser Gly Val Phe Gly Gly Lys Leu Ala Ala Ile Val Val Pro Pro Gly
225                 230                 235                 240
```

-continued

```
Val Asn Pro Val Gln Ser Thr Ser Met Leu Gln Tyr Pro His Val Leu
                245                 250                 255

Phe Asp Ala Arg Gln Val Glu Pro Val Ile Phe Ser Ile Pro Asp Leu
            260                 265                 270

Arg Ser Thr Leu Tyr His Leu Met Ser Asp Thr Asp Thr Thr Ser Leu
        275                 280                 285

Val Ile Met Val Tyr Asn Asp Leu Ile Asn Pro Tyr Ala Asn Asp Thr
    290                 295                 300

Asn Ser Ser Gly Cys Ile Val Thr Val Glu Thr Lys Pro Gly Pro Asp
305                 310                 315                 320

Phe Arg Phe His Leu Leu Lys Pro Pro Gly Ser Met Leu Thr His Gly
                325                 330                 335

Ser Val Pro Ser Asp Leu Ile Pro Lys Ser Ser Ser Leu Trp Ile Gly
            340                 345                 350

Asn Arg His Trp Thr Asp Ile Thr Asp Phe Val Ile Arg Pro Phe Val
        355                 360                 365

Phe Gln Ala Asn Arg His Phe Asp Phe Asn Gln Glu Thr Ala Gly Trp
    370                 375                 380

Ser Thr Pro Arg Phe Arg Pro Leu Thr Val Thr Ile Ser Gln Lys Asp
385                 390                 395                 400

Gly Asp Lys Leu Gly Thr Gly Val Ala Thr Asp Tyr Ile Val Pro Gly
                405                 410                 415

Ile Pro Asp Gly Trp Pro Asp Thr Thr Ile Pro Gly Glu Leu Ile Pro
            420                 425                 430

Ala Gly Asp Tyr Ala Ile Thr Thr Gly Asn Gly Thr Asp Ile Thr Thr
        435                 440                 445

Ala Gln Val Phe Asp Ser Ala Asp Val Ile Gln Asn Asn Thr Asn Phe
    450                 455                 460

Arg Gly Met Tyr Ile Cys Gly Ser Leu Gln Arg Ala Trp Gly Asp Lys
465                 470                 475                 480

Lys Ile Ser Asn Thr Ala Phe Ile Thr Thr Ala Ile Val Lys Gly Gly
                485                 490                 495

Lys Leu Arg Pro Ser Asn Val Ile Asp Gln Thr Lys Ile Ala Ile Phe
            500                 505                 510

Gln Asp Asn His Val Gln Ala Gly Ile Gln Thr Ser Asp Asp Thr Leu
        515                 520                 525

Ala Val Leu Gly Tyr Thr Gly Ile Gly Glu Gln Ala Ile Gly Ala Asp
    530                 535                 540

Arg Asp Arg Val Val Arg Ile Ser Val Leu Pro Glu Thr Gly Ala Arg
545                 550                 555                 560

Gly Gly Asn His Pro Ile Phe Tyr Lys Asn Ser Ile Lys Leu Gly Tyr
                565                 570                 575

Val Ile Arg Ser Ile Asp Val Phe Asn Ser Gln Ile Leu His Thr Ser
            580                 585                 590

Arg Gln Leu Ser Leu Asn His Tyr Leu Leu Pro Pro Asp Ser Phe Ala
        595                 600                 605

Val Tyr Arg Ile Ile Asp Ser Asn Gly Ser Trp Phe Asp Ile Gly Ile
    610                 615                 620

Asp Ser Asp Gly Phe Ser Phe Val Gly Val Ser Asn Ile Gly Lys Leu
625                 630                 635                 640

Glu Phe Pro Leu Ser Ala Ser Tyr Met Gly Ile Gln Leu Ala Lys Ile
                645                 650                 655
```

-continued

```
Arg Leu Ala Ser Asn Ile Arg Ser Ser Met Thr Lys Leu
            660                 665


<210> SEQ ID NO 48
<211> LENGTH: 668
<212> TYPE: PRT
<213> ORGANISM: Feline calicivirus

<400> SEQUENCE: 48

Met Cys Ser Thr Cys Ala Asn Val Leu Lys Tyr Tyr Asp Trp Asp Pro
1               5                   10                  15

His Phe Arg Leu Ile Ile Asn Pro Asn Lys Phe Leu Pro Ile Gly Phe
            20                  25                  30

Cys Asp Asn Pro Leu Met Cys Cys Tyr Pro Asp Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ala Ser Thr His Glu Ala Ile Asp
65                  70                  75                  80

Pro Ser Val Pro Pro Met His Trp Asp Ser Ala Gly Lys Ile Phe Gln
                85                  90                  95

Pro His Pro Gly Val Leu Met His His Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Ala Val Gly Gly Val Ile Ala
    130                 135                 140

Glu Pro Ser Ala Gln Met Ser Thr Ala Ala Asp Met Ala Ser Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Thr Leu Tyr His Val Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Val Leu Thr His Gly Ser
                325                 330                 335

Ile Pro Ser Asp Leu Ile Pro Lys Ser Ser Ser Leu Trp Ile Gly Asn
            340                 345                 350

Arg Tyr Trp Thr Asp Ile Thr Asp Phe Val Ile Arg Pro Phe Val Phe
        355                 360                 365
```

```
Gln Ala Asn Arg His Phe Asp Phe Asn Gln Glu Thr Ala Gly Trp Ser
    370                 375                 380

Thr Pro Arg Phe Arg Pro Ile Thr Ile Thr Ile Ser Glu Lys Asn Gly
385                 390                 395                 400

Ser Lys Leu Gly Ile Gly Val Ala Thr Asp Tyr Ile Ile Pro Gly Ile
                405                 410                 415

Pro Asp Gly Trp Pro Asp Thr Thr Ile Ala Asp Lys Leu Ile Pro Ala
            420                 425                 430

Gly Asp Tyr Ser Ile Thr Thr Gly Glu Gly Asn Asp Ile Lys Thr Ala
        435                 440                 445

Gln Ala Tyr Asp Thr Ala Ala Val Val Lys Asn Thr Thr Asn Phe Arg
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Ile Arg Asp Gly Asn Glu
                485                 490                 495

Ile Lys Pro Ser Asn Thr Ile Asp Met Thr Lys Leu Ala Val Tyr Gln
            500                 505                 510

Asp Thr His Val Gly Gln Glu Val Gln Thr Ser Asp Asp Thr Leu Ala
        515                 520                 525

Leu Leu Gly Tyr Thr Gly Ile Gly Glu Glu Ala Ile Gly Ser Asn Arg
    530                 535                 540

Asp Arg Val Val Arg Ile Ser Val Leu Pro Glu Ala Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Pro Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Glu Gly Phe Ser Phe Val Gly Val Ser Asp Ile Gly Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Arg Met Thr Lys Leu
            660                 665


<210> SEQ ID NO 49
<211> LENGTH: 668
<212> TYPE: PRT
<213> ORGANISM: Feline calicivirus

<400> SEQUENCE: 49

Met Cys Ser Thr Cys Ala Asn Val Leu Lys Tyr Tyr Asn Trp Asp Pro
1               5                   10                  15

His Ile Lys Leu Ser Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Met Trp Asp Cys Asp Gln Ser Pro Leu Gln Ile Tyr Leu Glu
    50                  55                  60

Ser Ile Leu Gly Asp Asp Glu Trp Ala Ser Thr Tyr Glu Ala Ile Asp
```

```
65                  70                  75                  80

Pro Val Val Pro Pro Met His Trp Asp Glu Met Gly Lys Ile Phe Gln
                85                  90                  95

Pro His Pro Gly Val Leu Met His His Ile Ile Gly Glu Val Ala Lys
            100                 105                 110

Gly Trp Asp Pro Asn Leu Pro Leu Phe Arg Leu Glu Ala Asp Asp Gly
        115                 120                 125

Ser Ile Thr Thr Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Pro Lys Ile Leu Phe Lys Gln Ser
            180                 185                 190

Leu Gly Pro Leu Leu Asn Pro Tyr Leu Gln His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Asp Pro Val Ile Phe Thr Ile Pro Asp Leu Arg
            260                 265                 270

Ser Thr Leu Tyr His Leu Met Ser Asp Thr Asp Thr Thr Pro Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Tyr Arg Pro Ile Thr Val Ser Ile Ser Gln Gln Glu Gly
385                 390                 395                 400

Ala Lys Leu Gly Ile Gly Val Ala Ile Asp Tyr Ile Val Pro Gly Ile
                405                 410                 415

Pro Asp Gly Trp Pro Arg Ser Thr Ile Pro Ser Lys Leu Val Pro Ala
            420                 425                 430

Gly Gly Tyr Ala Ile Thr Ala Lys Asn Gly Asn Asp Ile Thr Thr Ala
        435                 440                 445

Ala Gln Tyr Asp Ala Ala Gly Glu Ile Val Asn Asn Thr Asn Phe Lys
    450                 455                 460

Ser Met Tyr Ile Cys Gly Ala Leu Gln Arg Ala Trp Gly Asp Lys Lys
465                 470                 475                 480

Val Ser Asn Thr Ala Phe Val Thr Thr Ala Thr Val Thr Gly Asn Thr
                485                 490                 495
```

```
Leu Lys Pro Ser Asn Thr Ile Asp Asn Thr Lys Ile Ala Ile Tyr Gln
            500                 505                 510

Asp Asn His Val Asn Ser Asp Val Gln Thr Ser Asp Val Thr Leu Ser
        515                 520                 525

Leu Leu Gly Tyr Thr Gly Ile Gly Glu Glu Ala Val Gly Ala Asp Arg
    530                 535                 540

Asp Lys Leu Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Ile Asp Ala Asn Gly Ser Trp Phe Asp Ile Gly Ile Asp
    610                 615                 620

Ser Asp Gly Phe Ser Phe Val Gly Val Ser Asn Ile Gly Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Thr Met Thr Lys Leu
            660                 665


<210> SEQ ID NO 50
<211> LENGTH: 668
<212> TYPE: PRT
<213> ORGANISM: Feline calicivirus

<400> SEQUENCE: 50

Met Cys Ser Thr Cys Ala Asn Val Leu Lys Tyr Tyr Gly Trp Asp Pro
1               5                   10                  15

His Phe Arg Leu Thr Ile Asn Pro Asn Asp Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asn Asp Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Asp Gln Ala Gly Lys Ile Phe Gln
                85                  90                  95

Pro His Pro Gly Val Leu Met His His Leu Leu Gly Lys Val Ala Lys
            100                 105                 110

Gly Trp Asp Pro Asn Leu Pro Ser Phe Arg Leu Glu Ser Asp Asp Gly
        115                 120                 125

Ser Ile Thr Thr Pro Glu Gln Gly Thr Leu Val Gly Gly Val Ile Ala
    130                 135                 140

Glu Pro Ser Thr Gln Met Ala Thr Ala Ala Asp Met Ala Thr Gly Lys
145                 150                 155                 160

Thr Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Asn
            180                 185                 190

Leu Gly Pro Leu Leu Asn Pro Tyr Leu Glu His Ile Ala Gln Leu Tyr
```

```
        195                 200                 205

Val Ala Trp Ser Gly Ser Val Asp Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Gln Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Asn Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Ile Thr Val Glu Thr Lys Pro Gly Pro Asp Phe
305                 310                 315                 320

Lys Phe His Leu Leu Lys Pro Pro Gly Ser Met Leu Val His Gly Ser
                325                 330                 335

Ile Pro Ser Asn Leu Ile Pro Lys Ser Ser Ser Leu Trp Ile Gly Asn
            340                 345                 350

Arg His Trp Ser Asp Ile Thr Asp Phe Val Ile Arg Pro Ser Val Phe
        355                 360                 365

Gln Ala Asn Arg His Phe Asp Phe Lys Gln Glu Thr Ala Gly Trp Ser
    370                 375                 380

Thr Pro Arg Phe Arg Pro Met Thr Ile Thr Ile Ser Gln Lys Gln Ser
385                 390                 395                 400

Ala Lys Leu Gly Ile Ala Val Ala Leu Glu Ser Ile Val Pro Gly Ile
                405                 410                 415

Pro Asp Gly Trp Pro Asp Thr Thr Ile Asp Ser Asn Leu Ile Pro Ala
            420                 425                 430

Gly Asp Tyr Ala Ile Thr Asn Gln Ala Asp Asn Asp Ile Thr Thr Ala
        435                 440                 445

Met Glu Tyr Asp Ala Ala Thr Glu Ile Lys Asn Asn Thr Asn Phe Arg
    450                 455                 460

Ser Met Tyr Ile Cys Gly Ala Leu Gln Arg Ala Trp Gly Asp Lys Lys
465                 470                 475                 480

Val Ser Asn Thr Ala Phe Ile Thr Thr Ala Asp Leu Asp Gly Asn Thr
                485                 490                 495

Ile Lys Pro Asn Asn Val Ile Asn Gln Ser Arg Ile Ile Val Tyr Gln
            500                 505                 510

Asp Asn His Val Asn Leu Gln Val Gln Thr Ser Glu Val Thr Leu Ala
        515                 520                 525

Met Leu Gly Tyr Thr Gly Ile Gly Glu Glu Val Ile Gly Ala Asn Arg
    530                 535                 540

Asp Arg Val Val Arg Ile Asn Val Leu Pro Glu Val Ser Ala Arg Gly
545                 550                 555                 560

Gly Asn His Pro Ile Tyr Tyr Lys Asn Ser Leu Lys Leu Gly Tyr Val
                565                 570                 575

Ile Arg Ser Ile Asp Val Phe Asn Ser Gln Ile Leu His Thr Ser Arg
            580                 585                 590

Gln Leu Ala Leu Asn Asn Tyr Leu Leu Asp Pro Asp Cys Phe Ala Val
        595                 600                 605

Tyr Arg Ile Thr Asp Ser Asn Gly Ser Trp Phe Asp Ile Gly Ile Asp
    610                 615                 620
```

```
Tyr Ser Gly Phe Ser Phe Val Gly Val Ser Asn Ile Gly Ala Leu Glu
625                 630                 635                 640

Phe Pro Leu Thr Ala Ser Tyr Thr Gly Ile Gln Leu Ala Lys Ile Arg
                645                 650                 655

Leu Ala Ser Asn Ile Arg Ser Ser Met Thr Lys Leu
            660                 665


<210> SEQ ID NO 51
<211> LENGTH: 668
<212> TYPE: PRT
<213> ORGANISM: Feline calicivirus

<400> SEQUENCE: 51

Met Cys Ser Thr Cys Ala Asn Val Leu Lys Tyr Tyr Gly Trp Asp Pro
1               5                   10                  15

His Phe Asp Leu Val Ile Asn Pro Asn Asp Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asn Asp Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Lys Gln Ala Gly Lys Ile Phe Gln
                85                  90                  95

Pro His Pro Gly His Leu Met His His Leu Ile Gly Lys Val Ser Lys
            100                 105                 110

Gly Trp Asp Pro Asn Leu Pro Asn Phe Arg Leu Glu Ala Asp Asp Gly
        115                 120                 125

Ser Ile Thr Ala Pro Glu Gln Gly Thr Leu Val Gly Gly Val Ile Ala
    130                 135                 140

Glu Pro Ser Ala Gln Met Ser Thr Ala Ala Asp Met Ala Thr Gly Lys
145                 150                 155                 160

Thr Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Gly His Leu Ala Gln Leu Tyr
        195                 200                 205

Val Ala Trp Ser Gly Ser Val Asp Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Arg Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Ser Leu Tyr His Leu Met Ser Asp Thr Asp Thr Thr Ser Leu Val
        275                 280                 285

Ile Met Val Tyr Asn Asp Leu Ile Asn Pro Tyr Ala Gly Asp Ser Asn
    290                 295                 300

Ser Ser Gly Cys Ile Ile Thr Val Glu Thr Lys Pro Gly Ala Asp Phe
305                 310                 315                 320

Lys Phe His Leu Leu Lys Pro Pro Gly Ser Val Leu Thr His Gly Ser
```

-continued

```
                325                 330                 335

Val Pro Ser Asp Leu Ile Pro Lys Thr Ser Ser Leu Trp Ile Gly Asn
            340                 345                 350

Arg His Trp Ala Asp Ile Thr Asp Phe Val Ile Arg Pro Ser Val Phe
        355                 360                 365

Gln Ala Asn Arg His Phe Asp Phe Lys Gln Glu Thr Ala Gly Trp Ser
    370                 375                 380

Thr Pro Arg Phe Arg Pro Met Thr Val Thr Ile Ser Gln Ser Gly Gly
385                 390                 395                 400

Ala Lys Leu Gly Ile Gly Ile Ala His Glu Thr Ile Val Pro Gly Ile
                405                 410                 415

Pro Asp Gly Trp Pro Asp Thr Thr Ile Pro Gly Glu Leu Val Pro Ala
            420                 425                 430

Gly Glu Tyr Ala Ile Val Asn Gln Thr Ser Asn Asp Ile Ala Thr Ala
        435                 440                 445

Val Asp Tyr Asp Thr Ala Thr Ala Ile Thr Asn Asn Thr Asn Phe Lys
    450                 455                 460

Ser Met Tyr Ile Cys Gly Ala Leu Gln Arg Ala Trp Gly Asp Lys Lys
465                 470                 475                 480

Ile Ser Asn Thr Ala Phe Ile Thr Thr Ala Asp Leu Asn Gly Asn Lys
                485                 490                 495

Ile Lys Pro Asn Asn Val Ile Asn Gln Gln Arg Ile Val Ile Phe Gln
            500                 505                 510

Asp Asn His Val Gly Ser Glu Ala Gln Thr Ser Asp Val Thr Leu Ala
        515                 520                 525

Met Leu Gly Tyr Thr Gly Ile Gly Glu Glu Val Ile Gly Ala Asp Arg
    530                 535                 540

Asp Arg Val Val Arg Ile Asn Val Leu Pro Glu Val Ser Ala Arg Gly
545                 550                 555                 560

Gly Asn His Pro Ile Phe Tyr Lys Asn Thr Leu Lys Leu Gly Tyr Val
                565                 570                 575

Ile Arg Ser Ile Asp Val Phe Asn Ser Gln Ile Leu His Thr Ser Arg
            580                 585                 590

Gln Leu Ala Leu Asn Asn Tyr Leu Leu Asp Pro Asp Ser Phe Ala Val
        595                 600                 605

Tyr Arg Ile Thr Asp Ser Asn Gly Ser Trp Phe Asp Ile Gly Ile Asp
    610                 615                 620

Tyr Ser Gly Phe Ser Phe Val Gly Val Ser Asn Ile Gly Glu Leu Glu
625                 630                 635                 640

Phe Pro Leu Thr Ala Ser Tyr Met Gly Val Gln Leu Ala Lys Ile Arg
                645                 650                 655

Leu Ala Ser Asn Ile Arg Ser Ser Met Thr Lys Leu
            660                 665


<210> SEQ ID NO 52
<211> LENGTH: 668
<212> TYPE: PRT
<213> ORGANISM: Feline calicivirus

<400> SEQUENCE: 52

Met Cys Ser Thr Cys Ala Asn Val Leu Lys Tyr Tyr Asn Trp Asp Pro
1               5                   10                  15

His Phe Lys Met Val Val Asn Pro Asn Lys Phe Leu Ser Val Gly Phe
            20                  25                  30
```

-continued

Cys Asp Lys Pro Leu Leu Cys Cys Tyr Pro Asp Leu Leu Pro Glu Phe
35 40 45

Gly Thr Val Trp Asp Cys Asn Gln Ser Pro Leu Glu Ile Tyr Leu Glu
50 55 60

Ser Ile Leu Gly Asp Asp Glu Trp Ser Ser Thr Phe Glu Ala Ile Asp
65 70 75 80

Pro Val Val Pro Pro Met His Trp Asp Asp Ala Gly Lys Ile Phe Gln
85 90 95

Pro His Pro Gly Val Leu Met His His Leu Ile Ser Glu Val Ala Lys
100 105 110

Gly Trp Asp Pro Asn Leu Pro Leu Phe Arg Leu Glu Ala Asp Asp Gly
115 120 125

Ser Ile Thr Ala Pro Glu Gln Gly Thr Val Val Gly Gly Val Ile Ala
130 135 140

Glu Pro Ser Pro Gln Met Ala Val Ala Ala Asp Thr Ala Thr Gly Lys
145 150 155 160

Ser Val Asp Ser Glu Trp Glu Ala Phe Phe Ser Phe His Thr Ser Val
165 170 175

Asn Trp Ser Thr Ser Glu Thr Gln Gly Lys Ile Leu Phe Lys Gln Ser
180 185 190

Leu Gly Pro Leu Leu Asn Pro Tyr Leu Glu His Leu Ser Lys Leu Tyr
195 200 205

Val Ala Trp Ser Gly Ser Val Glu Val Arg Phe Ser Ile Ser Gly Ser
210 215 220

Gly Val Phe Gly Gly Lys Leu Ala Ala Ile Val Val Pro Pro Gly Val
225 230 235 240

Asp Pro Val Gln Ser Thr Ser Met Leu Gln Tyr Pro His Val Leu Phe
245 250 255

Asp Ala Arg Gln Val Glu Pro Val Ile Phe Thr Leu Pro Asp Leu Arg
260 265 270

Asn Ser Leu Tyr His Leu Met Ser Asp Thr Asp Thr Thr Ser Leu Val
275 280 285

Ile Met Val Tyr Asn Asp Leu Ile Asn Pro Tyr Ala Asn Asp Ser Asn
290 295 300

Ser Ser Gly Cys Val Val Thr Val Glu Thr Lys Pro Gly Ala Asp Phe
305 310 315 320

Lys Phe His Leu Leu Lys Pro Pro Gly Ser Met Leu Thr His Gly Ser
325 330 335

Val Pro Ser Asp Leu Ile Pro Arg Ser Ser Ser Leu Trp Ile Gly Asn
340 345 350

Arg Tyr Trp Thr Asp Ile Thr Asp Phe Val Ile Arg Pro Phe Val Phe
355 360 365

Gln Ala Asn Arg His Phe Asp Phe Asn Gln Glu Thr Ala Gly Trp Ser
370 375 380

Thr Pro Arg Phe Arg Pro Ile Thr Ile Thr Ile Ser Glu Lys Asn Gly
385 390 395 400

Glu Lys Leu Gly Ile Gly Val Ala Thr Asp Tyr Ile Val Pro Gly Ile
405 410 415

Pro Asp Gly Trp Pro Asp Thr Thr Ile Ala Glu Lys Leu Thr Pro Ala
420 425 430

Gly Asp Tyr Ala Ile Thr Thr Gly Asp Gly Asn Asp Ile Ile Thr Ala
435 440 445

Asn Ala Tyr Asp Thr Ala Asp Val Val Lys Asn Asn Thr Asn Phe Arg

```
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Gly Thr Val Ser Asp Asn Lys
                485                 490                 495

Ile Lys Pro Ser Asn Val Ile Asp Pro Thr Lys Leu Ala Val Phe Gln
            500                 505                 510

Asp Asn His Val Gly Ala Asp Ala Gln Thr Ser Asp Asp Thr Leu Ala
        515                 520                 525

Leu Leu Gly Tyr Thr Gly Ile Gly Glu His Ala Ile Gly Ala Asp Arg
    530                 535                 540

Glu Arg Val Val Arg Ile Ser Thr Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Pro Pro Asp Ser Phe Ala Val
        595                 600                 605

Tyr Arg Ile Ile Asp Ser Asn Gly Ser Trp Phe Asp Ile Gly Ile Asp
    610                 615                 620

Ser Asp Gly Phe Ser Phe Val Gly Val Thr Asn Ile Gly Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Ser Met Ile Lys Leu
            660                 665


<210> SEQ ID NO 53
<211> LENGTH: 668
<212> TYPE: PRT
<213> ORGANISM: Feline calicivirus

<400> SEQUENCE: 53

Met Cys Ser Thr Cys Ala Asn Val Leu Lys Tyr Tyr Asn Trp Asp Pro
1               5                   10                  15

His Phe Lys Leu Val Ile Asn Pro Asn Lys Phe Leu Ser Ile Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Val Val Pro Pro Met His Trp Asn Glu Ala Gly Lys Ile Phe Gln
                85                  90                  95

Pro His Pro Gly Val Leu Met His His Ile Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Ala Pro Glu Gln Gly Thr Val Val Gly Gly Val Ile Ala
    130                 135                 140

Glu Pro Ser Ser Gln Met Ser Thr Ala Ala Asp Met Ala Ser Gly Lys
145                 150                 155                 160
```

-continued

```
Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Ile Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Ser Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Thr Ser Ser Leu Trp Ile Gly Asn
            340                 345                 350

Arg Phe Trp Ser Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Val Thr Ile Ser Glu Lys Asn Gly
385                 390                 395                 400

Ala Lys Leu Gly Val Gly Val Ala Thr Asp Phe Ile Val Pro Gly Ile
                405                 410                 415

Pro Asp Gly Trp Pro Asp Thr Thr Ile Gly Glu Lys Leu Val Pro Ala
            420                 425                 430

Gly Asp Tyr Ala Ile Thr Asn Gly Ser Gly Asn Asp Ile Thr Thr Ala
        435                 440                 445

Asn Gln Tyr Asp Ala Ala Asp Ile Ile Arg Asn Asn Thr Asn Phe Lys
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Thr Val Glu Gly Asn Asp
                485                 490                 495

Leu Ile Pro Ser Asn Val Ile Asp Gln Thr Lys Ile Ala Ile Phe Gln
            500                 505                 510

Asp Asn His Val Gln Asp Glu Val Gln Thr Ser Asp Asp Thr Leu Ala
        515                 520                 525

Leu Leu Gly Tyr Thr Gly Ile Gly Glu Glu Ala Ile Gly Ala Asn Arg
    530                 535                 540

Glu Arg Val Val Arg Ile Ser Thr Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
```

```
            580                 585                 590

Gln Leu Ser Leu Asn His Tyr Leu Leu Pro Pro Asp Ser Phe Ala Val
        595                 600                 605

Tyr Arg Ile Ile Asp Ser Asn Gly Ser Trp Phe Asp Val Gly Ile Asp
    610                 615                 620

Phe Asp Gly Phe Ser Phe Val Gly Val Ser Asp Val Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Thr Met Thr Lys Leu
            660                 665


<210> SEQ ID NO 54
<211> LENGTH: 668
<212> TYPE: PRT
<213> ORGANISM: Feline calicivirus

<400> SEQUENCE: 54

Met Cys Ser Thr Cys Ala Asn Val Leu Lys Tyr Tyr Asp Trp Asp Pro
1               5                   10                  15

His Ile Arg Leu Val Ile Asp Pro Asn Arg Phe Leu Ser Val Ser Phe
            20                  25                  30

Cys Asp Lys Pro Leu Leu Cys Cys Tyr Pro Asp Leu Leu Pro Glu Phe
        35                  40                  45

Gly Thr Val Trp Asp Cys Asn Gln Ser Pro Leu Glu Ile Tyr Leu Glu
    50                  55                  60

Ser Ile Leu Gly Asp Asp Glu Trp Ser Ser Thr Phe Glu Ala Ile Asp
65                  70                  75                  80

Pro Val Val Pro Pro Met His Trp Asp Glu Ala Gly Lys Ile Phe Gln
                85                  90                  95

Pro His Pro Gly Val Leu Met His His Leu Ile Asn Gln Val Ala Lys
            100                 105                 110

Ala Trp Asp Pro Asn Leu Pro Leu Phe Arg Leu Glu Ala Asp Asp Gly
        115                 120                 125

Ser Ile Thr Ser Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ala Lys Leu Tyr
        195                 200                 205

Val Ala Trp Ser Gly Ser Val Asp Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asn Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Thr Leu Tyr His Leu Met Ser Asp Thr Asp Thr Thr Ser Leu Val
        275                 280                 285
```

-continued

```
Ile Met Val Tyr Asn Asp Leu Ile Asn Pro Tyr Ala Ser Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Thr Ile Ser Glu Lys Asp Gly
385                 390                 395                 400

Ser Lys Leu Gly Ile Gly Val Ala Met Asp Ser Ile Val Pro Gly Ile
                405                 410                 415

Pro Asp Gly Trp Pro Asp Thr Thr Ile Pro Glu Lys Leu Val Pro Ala
            420                 425                 430

Gly Asp Tyr Ala Ile Ala Asn Gly Thr Gly Asn Asp Ile Thr Thr Ala
        435                 440                 445

Lys Asp Tyr Asp Ser Ala Thr Val Ile Gln Asn Asn Thr Asn Phe Lys
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Thr Arg Ser Asp Asn Thr
                485                 490                 495

Ile Thr Pro Ser Asn Val Ile Asp Pro Thr Lys Ile Ala Val Tyr Gln
            500                 505                 510

Asp Thr His Val Gly Ala Glu Val Gln Thr Ser Asp Asp Thr Leu Ala
        515                 520                 525

Ile Leu Gly Tyr Thr Gly Ile Gly Glu Glu Ala Ile Gly Ala Asp Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Thr Asp Ser Asn Gly Ser Trp Phe Asp Ile Gly Ile Asp
    610                 615                 620

Ser Asp Gly Phe Ser Phe Val Gly Ala Ser Asn Val Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Ser Met Thr Lys Leu
            660                 665
```

<210> SEQ ID NO 55
<211> LENGTH: 668
<212> TYPE: PRT
<213> ORGANISM: Feline calicivirus

<400> SEQUENCE: 55

-continued

```
Met Cys Ser Thr Cys Ala Asn Val Leu Lys Tyr Tyr Asp Trp Asp Pro
1               5                   10                  15

His Phe Arg Leu Asn Val Asn Pro Asn Glu Phe Leu Ser Val Gly Phe
            20                  25                  30

Cys Asp Lys Pro Leu Met Cys Cys Tyr Pro Glu Leu Leu Pro Glu Phe
        35                  40                  45

Gly Thr Val Trp Asp Cys Ser Arg Ala Pro Leu Glu Ile Tyr Leu Glu
    50                  55                  60

Ser Ile Leu Gly Asp Asp Glu Trp Ser Ser Thr His Glu Ala Ile Asp
65                  70                  75                  80

Pro Val Val Pro Pro Met His Trp Asp Glu Ala Gly Lys Ile Phe Gln
                85                  90                  95

Pro His Pro Gly Val Leu Met His His Leu Ile Asn Lys Val Ala Arg
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Leu Val Gly Gly Val Ile Ala
    130                 135                 140

Glu Pro Ser Ser Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Asp Pro Val Ile Phe Thr Ile Pro Asp Leu Arg
            260                 265                 270

Ser Asn Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Leu Ser Val Thr Ile Ser Gln Ser Gly Gly
385                 390                 395                 400

Ala Lys Leu Gly Ile Gly Ile Ala Thr Asp Tyr Ile Val Pro Gly Ile
                405                 410                 415
```

```
Pro Asp Gly Trp Pro Asp Thr Thr Ile Pro Gly Glu Leu Thr Pro Ala
            420                 425                 430

Gly Asp Tyr Ala Ile Val Asn Gln Asn Asn Ser Asp Ile Ala Thr Lys
        435                 440                 445

Gln Ala Tyr Glu Ser Ala Thr Ser Ile Glu Asn Asn Thr Asn Phe Lys
    450                 455                 460

Ser Met Tyr Ile Cys Gly Ser Leu His Arg Ala Trp Gly Asp Lys Lys
465                 470                 475                 480

Ile Ser Asn Thr Ala Phe Ile Thr Thr Ala Thr Val Asp Gly Asn Asn
                485                 490                 495

Leu Ile Pro Ser Asn Thr Ile Gly Gln Asp Lys Ile Ala Val Phe Gln
            500                 505                 510

Asp Asn His Val Asn Ala Glu Val Gln Thr Ser Asp Val Thr Leu Ala
        515                 520                 525

Thr Leu Gly Tyr Thr Gly Ile Gly Glu Glu Ala Ile Gly Ala Ile Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ala Met Lys Leu Gly Tyr Val
                565                 570                 575

Ile Gly Asp Ile Asp Val Phe Asn Ser Gln Ile Leu His Thr Ser Arg
            580                 585                 590

Gln Leu Ser Leu Asn Asn Tyr Leu Leu Pro Pro Asp Ser Phe Ala Val
        595                 600                 605

Tyr Arg Ile Ile Asp Ser Asn Gly Ser Trp Phe Asp Val Gly Ile Asp
    610                 615                 620

Ser Asp Gly Phe Ser Phe Val Gly Val Ser Ser Ile Pro Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Thr Met Thr Lys Leu
            660                 665


<210> SEQ ID NO 56
<211> LENGTH: 671
<212> TYPE: PRT
<213> ORGANISM: Feline calicivirus

<400> SEQUENCE: 56

Met Cys Ser Thr Cys Ala Asn Val Leu Lys Tyr Tyr Gly Trp Asp Pro
1               5                   10                  15

His Phe Lys Leu Val Ile Asn Pro Asn Asn Phe Leu Pro Val Gly Phe
            20                  25                  30

Cys Ser Asn Pro Leu Met Cys Cys Tyr Pro Glu Leu Leu Pro Glu Phe
        35                  40                  45

Gly Thr Val Trp Asp Cys Asp Arg Ser Pro Leu Glu Ile Tyr Leu Glu
    50                  55                  60

Ser Ile Leu Gly Asp Asp Glu Trp Ala Ser Thr Phe Asp Ala Val Asp
65                  70                  75                  80

Pro Val Val Pro Pro Met His Trp Ser Ala Ala Gly Lys Ile Phe Gln
                85                  90                  95

Pro His Pro Gly Val Leu Met His His Leu Ile Gly Lys Val Ala Ala
            100                 105                 110

Gly Trp Asp Pro Asp Leu Pro Leu Ile Arg Leu Glu Ala Asp Asp Gly
        115                 120                 125
```

-continued

```
Ser Ile Thr Ala Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Ala Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Thr Ser Ser Leu Trp Ile Gly Asn
            340                 345                 350

Arg Tyr Trp Ser Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Ser Val Thr Ile Ser Gln Gln Asp Gly
385                 390                 395                 400

Ala Lys Leu Gly Ile Gly Val Ala Thr Asp Tyr Ile Val Pro Gly Ile
                405                 410                 415

Pro Asp Gly Trp Pro Asp Thr Thr Ile Pro Gly Glu Leu Ile Pro Ala
            420                 425                 430

Gly Asp Tyr Ala Ile Thr Asn Asn Ile Gly Asp Asp Ile Thr Thr Ala
        435                 440                 445

Thr Gly Tyr Asp Thr Ala Asp Ile Ile Lys Asn Asn Thr Asn Phe Lys
    450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Ala Thr Leu Ser Gly Asn Asn
                485                 490                 495

Asn Asn Lys Ile Asn Pro Cys Asn Thr Ile Asp Gln Ser Lys Ile Val
            500                 505                 510

Val Phe Gln Asp Asn His Val Gly Lys Glu Val Gln Thr Ser Asp Asp
        515                 520                 525

Thr Leu Ala Leu Leu Gly Tyr Thr Gly Ile Gly Glu Gln Ala Ile Gly
    530                 535                 540
```

Ser Asp Arg Asp Arg Val Val Arg Ile Ser Thr Leu Pro Glu Thr Gly
545 550 555 560

Ala Arg Gly Gly Asn His Pro Ile Phe Tyr Lys Asn Ser Ile Lys Leu
565 570 575

Gly Tyr Val Ile Arg Ser Ile Asp Val Phe Asn Ser Gln Ile Leu His
580 585 590

Thr Ser Arg Gln Leu Ser Leu Asn His Tyr Leu Leu Pro Pro Asp Ser
595 600 605

Phe Ala Val Tyr Arg Ile Ile Asp Ser Asn Gly Ser Trp Phe Asp Ile
610 615 620

Gly Ile Asp Ser Asp Gly Phe Ser Phe Val Gly Val Ser Gly Phe Gly
625 630 635 640

Lys Leu Glu Phe Pro Leu Ser Ala Ser Tyr Met Gly Ile Gln Leu Ala
645 650 655

Lys Ile Arg Leu Ala Ser Asn Ile Arg Ser Pro Met Thr Lys Leu
660 665 670

<210> SEQ ID NO 57
<211> LENGTH: 668
<212> TYPE: PRT
<213> ORGANISM: Feline calicivirus

<400> SEQUENCE: 57

Met Cys Ser Thr Cys Ala Asn Val Leu Lys Tyr Tyr Asp Trp Asp Pro
1 5 10 15

His Ile Arg Leu Val Ile Asn Pro Asn Lys Phe Leu Pro Ile Gly Phe
20 25 30

Cys Asp Asn Pro Leu Met Cys Cys Tyr Pro Glu Leu Leu Pro Glu Phe
35 40 45

Gly Thr Val Trp Asp Cys Asp Gln Ser Pro Leu Gln Ile Tyr Leu Glu
50 55 60

Ser Ile Leu Gly Asp Asp Glu Trp Ala Ser Thr Tyr Asp Ala Ile Asp
65 70 75 80

Pro Val Val Pro Pro Met His Trp Asp Asp Ala Gly Lys Ile Phe Gln
85 90 95

Pro His Pro Gly Val Leu Met His Phe Leu Ile Asn Glu Val Ala Lys
100 105 110

Gly Trp Asp Pro Ser Leu Pro Ser Phe Arg Leu Glu Ala Asp Asp Gly
115 120 125

Ser Ile Thr Thr Pro Glu Gln Gly Thr Ala Val Gly Gly Val Ile Ala
130 135 140

Gln Pro Ser Ala Gln Met Ser Ala Ala Ala Asp Met Ala Ser Gly Lys
145 150 155 160

Ser Val Asp Ser Glu Trp Glu Glu Phe Phe Ser Phe His Thr Ser Val
165 170 175

Asn Trp Ser Thr Thr Glu Thr Gln Gly Lys Ile Leu Phe Lys Gln Ser
180 185 190

Leu Gly Pro Leu Leu Asn Pro Tyr Leu Glu His Leu Ser Lys Leu Tyr
195 200 205

Val Ala Trp Ser Gly Ser Ile Asp Val Arg Phe Ser Ile Ser Gly Ser
210 215 220

Gly Val Phe Gly Gly Lys Leu Ala Ala Ile Val Val Pro Pro Gly Val
225 230 235 240

Asp Pro Val Gln Ser Thr Ser Met Leu Gln Tyr Pro His Val Leu Phe
245 250 255

-continued

```
Asp Ala Arg Gln Val Glu Pro Val Ile Phe Ser Leu Pro Asp Leu Arg
            260                 265                 270

Asn Ser Leu Tyr His Leu Ile Ser Asp Thr Asp Thr Thr Ser Leu Val
        275                 280                 285

Ile Met Val Tyr Asn Asp Leu Ile Asn Pro Tyr Ala Asn Glu Ala Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Arg Ser Ser Ser Leu Trp Ile Gly Asn
            340                 345                 350

Arg His Trp Thr Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Asn Ile Ser Gln Lys Glu Gly
385                 390                 395                 400

Ala Arg Leu Gly Thr Ala Ile Ala Val Asp Thr Ile Leu Pro Gly Ile
                405                 410                 415

Pro Asp Gly Trp Pro Asp Thr Thr Ile Pro Thr Val Leu Thr Pro Ala
            420                 425                 430

Gly Lys Tyr Ala Ile Thr Ser Gly Asn Asn Ser Asp Ile Leu Thr Arg
        435                 440                 445

Asn Asp Tyr Glu Asn Ala Asp Val Ile Lys Asn Asn Thr Asn Phe Arg
    450                 455                 460

Ser Met Tyr Ile Cys Gly Ser Leu Gln Arg Ala Trp Gly Asp Lys Asp
465                 470                 475                 480

Ile Ser Asn Thr Ala Phe Ile Thr Thr Gly Thr Val Asn Gly Asn Asn
                485                 490                 495

Ile Glu Pro Ser Asn Thr Ile Asp Pro Thr Lys Leu Ala Val Phe Gln
            500                 505                 510

Asp Asn His Val Lys Ser Glu Val Gln Thr Ser Asp Val Thr Leu Ser
        515                 520                 525

Val Leu Gly Tyr Thr Gly Ile Gly Glu Glu Ala Val Gly Ala Asp Arg
    530                 535                 540

Asp Lys Val Val Arg Ile Ser Val Leu Pro Glu Thr Gly Ala Arg Gly
545                 550                 555                 560

Gly Asn His Pro Ile Phe Tyr Lys Asn Ser Met Lys Leu Gly Tyr Val
                565                 570                 575

Ile Ser Ser Ile Asp Val Phe Asn Ser Gln Ile Leu His Thr Ser Arg
            580                 585                 590

Gln Leu Ser Leu Asn His Tyr Leu Leu Pro Pro Asp Ser Phe Ala Val
        595                 600                 605

Tyr Arg Ile Thr Asp Ser Asn Gly Ser Trp Phe Asp Ile Gly Ile Asp
    610                 615                 620

Asn Asp Gly Phe Ser Phe Val Gly Val Ser His Ile Gly Lys Leu Glu
625                 630                 635                 640

Phe Pro Leu Ser Ala Ser Tyr Met Gly Ile Gln Leu Ala Lys Ile Arg
                645                 650                 655

Leu Ala Ser Asn Ile Arg Ser Ser Met Ile Lys Leu
            660                 665
```

<210> SEQ ID NO 58
<211> LENGTH: 668
<212> TYPE: PRT
<213> ORGANISM: Feline calicivirus

<400> SEQUENCE: 58

Met Cys Ser Thr Cys Ala Asn Val Leu Lys Tyr Tyr Asp Trp Asp Pro
1 5 10 15

His Phe Arg Leu Val Ile Asp Pro Asn Lys Phe Leu Ser Val Gly Phe
20 25 30

Cys Asp Asn Pro Leu Met Cys Cys Tyr Pro Glu Leu Leu Pro Glu Phe
35 40 45

Gly Thr Val Trp Asp Cys Asp Gln Ser Pro Leu Gln Ile Tyr Leu Glu
50 55 60

Ser Ile Leu Gly Asp Asp Glu Trp Ala Ser Thr Tyr Glu Ala Ile Asp
65 70 75 80

Pro Ser Val Pro Pro Met His Trp Asp Ser Ala Gly Lys Ile Phe Gln
85 90 95

Pro His Pro Gly Val Leu Met His Tyr Ile Ile Gly Glu Val Ala Lys
100 105 110

Ala Trp Asp Pro Asn Leu Pro Asn Phe Arg Leu Glu Ala Asp Asp Gly
115 120 125

Ser Ile Thr Thr Pro Glu Gln Gly Thr Met Val Gly Gly Val Ile Ala
130 135 140

Glu Pro Ser Ala Gln Met Ala Thr Ala Ala Asp Thr Ala Thr Gly Lys
145 150 155 160

Ser Val Asp Ser Glu Trp Glu Ala Phe Phe Ser Phe His Thr Ser Val
165 170 175

Asn Trp Ser Thr Ser Glu Thr Gln Gly Lys Ile Leu Phe Lys Gln Ser
180 185 190

Leu Gly Pro Leu Leu Asn Pro Tyr Leu Thr His Leu Ala Lys Leu Tyr
195 200 205

Val Ala Trp Ser Gly Ser Ile Glu Val Arg Phe Ser Ile Ser Gly Ser
210 215 220

Gly Val Phe Gly Gly Lys Leu Ala Ala Ile Val Val Pro Pro Gly Ile
225 230 235 240

Asp Pro Val Gln Ser Thr Ser Met Leu Gln Tyr Pro His Val Leu Phe
245 250 255

Asp Ala Arg Gln Val Glu Pro Val Ile Phe Thr Ile Pro Asp Leu Arg
260 265 270

Ser Thr Leu Tyr His Leu Met Ser Asp Thr Asp Thr Thr Ser Leu Val
275 280 285

Ile Met Val Tyr Asn Asp Leu Ile Asn Pro Tyr Ala Asn Asp Ser Asn
290 295 300

Ser Ser Gly Cys Ile Leu Thr Val Glu Thr Lys Pro Gly Pro Asp Phe
305 310 315 320

Lys Phe His Leu Leu Lys Pro Pro Gly Ser Met Leu Thr His Gly Ser
325 330 335

Val Pro Ser Asp Leu Ile Pro Lys Ser Ser Ser Leu Trp Ile Gly Asn
340 345 350

Arg Tyr Trp Ser Asp Ile Asn Asp Phe Val Ile Arg Pro Phe Val Phe
355 360 365

Gln Ala Asn Arg His Phe Asp Phe Asn Gln Glu Thr Ala Gly Trp Ser
370 375 380

```
Thr Pro Arg Phe Arg Pro Ile Thr Val Thr Ile Ser Val Lys Glu Ser
385                 390                 395                 400

Ala Lys Leu Gly Ile Gly Val Ala Thr Asp Tyr Ile Val Pro Gly Ile
                405                 410                 415

Pro Asp Gly Trp Pro Asp Thr Thr Ile Pro Thr Asp Leu Thr Pro Ala
            420                 425                 430

Gly Asp Tyr Ala Ile Thr Asp Ser Thr Gly Asn Asp Ile Thr Thr Pro
        435                 440                 445

Ser Gly Tyr Asp Ser Ala Ile Ser Ile Val Asn Asn Thr Asn Phe Arg
    450                 455                 460

Gly Met Tyr Ile Cys Gly Ser Leu Gln Arg Ala Trp Gly Asp Lys Lys
465                 470                 475                 480

Val Ser Asn Thr Ala Phe Ile Thr Thr Gly Ile Val Thr Gly Asn Lys
                485                 490                 495

Leu Glu Pro Ser Asn Thr Ile Asp Gln Thr Lys Ile Ala Ile Phe Gln
            500                 505                 510

Asp Thr His Ala Asn Arg Asp Thr Gln Ile Ser Asp Asp Thr Leu Ala
        515                 520                 525

Leu Leu Gly Tyr Thr Gly Ile Gly Glu Glu Ala Ile Gly Ala Asp Arg
    530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Phe Ala Val
        595                 600                 605

Tyr Arg Ile Thr Asp Ser Asn Gly Ser Trp Phe Asp Ile Gly Ile Asp
    610                 615                 620

Ser Asp Gly Phe Ser Phe Val Gly Val Asn Asn Ile Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Thr Met Thr Lys Leu
            660                 665
```

<210> SEQ ID NO 59
<211> LENGTH: 7685
<212> TYPE: DNA
<213> ORGANISM: Feline calicivirus

<400> SEQUENCE: 59

```
gtaaaagaaa tttgagacaa tgtctcaaac tctgagcttc gtgcttaaaa ctcacagcgt     60

ccgcaaggac tttgtgcact ccgtcaagct aacgcttgca cggaggcgcg atcttcagta    120

tttctataac aagctctctc gttctatgcg agctgaagct tgtccttctt gtgccagtta    180

tgatgtatgt cctaactgca cttctagtga tatccctgat gatggttcat caacaacgtt    240

gatgccatca tgggaggatg tcacaaaaac ctctacttac tctcttctac tctccgaaga    300

tacttctgac gagttgtctc ctgacgaatt ggttcacgtt gctgctcaca ttcgcaaggc    360

gctttccact cagtctcatc cggccaatgt tgacatgtgc aaagaacagc tcacgtcatt    420

attggtgatg gctgaagcta tgctgcctca acggtcacga gcaacaatcc cacttcatca    480
```

-continued

```
acaacaccag acggctcgca ttgaatggag ggaaaagttc ttctctaagc cccttaactt    540
cattcttgaa aagattggtg tttctaaaga tattcttcag gttactgccc tttggaaaat    600
catcttggag aaagcttgct actgcaaatc ctatggtgaa gagtggttcg atgctgcaaa    660
gaacaaacta agggagatga gaagcttcga aagcaacaca ctcaaaccac tggttggagc    720
tttcattgac ggcttaaggt ttatgactgt ggataacccc aaccctatgg cattcttacc    780
caagctaatt gggcttatca aacccctcaa tttggcaatg ataatcgaca atcatgaaaa    840
cacactatca ggatggatca ttaccctcac tgcaattatg gagttataca acatcacaga    900
atgcacaatt gacataatca cttcactggt aacagcattc tatgacaaaa ttgctaaagc    960
ccctaaattc tacagtcaga tcaaagcact gttcacggga tttaggacag aggatgtggc   1020
taattcattt tggtatatgg ctgctgcaat tctatgttac ctgattacgg gtataatccc   1080
aaacaatggg aggttttcaa agattaaaac ctgcctgtct ggtgcaacga ccctggtatc   1140
gggtataatt gccacacaga aacttgcagc aatgttcgct acatggaact ctgaatccat   1200
tgttaacgaa ttatctgcaa ggacagtggc tatttctgaa ttgaataacc caactactac   1260
ctctgacact gactctgttg agcggttgct cgaattggct aagatcttgc acgaggagat   1320
caaagttcac actctgaatc caattatgca atcatacaac ccaattctta gaaatttaat   1380
gtccacacta gacggtgttg tcacctcatg caacaagaga agagcaattg ccaaaaagag   1440
gcaagtccca gtttgctaca tccttactgg accacctgga tgtggcaaga ccactgcggc   1500
cctagccctt gcaaagaagc tctctgatca agagccatca gtgattaatt tggatgttga   1560
tcatcatgat acttacactg gcaatgaagt gtgcattgtt gatgagtttg attcatcaga   1620
caaagtggac tatgcaaatt ttgtgattgg tatggttaat tcggcaccaa tggttctaaa   1680
ttgtgatatg cttgaaaata agggaaagct ctttacctct aagtacataa taatgacttc   1740
taactctgaa acccctgtaa aaccctcttc taagcgtgca ggtgctttct accgaagagt   1800
tacaatcatt gacgttgcaa accctttggt ggaatctcac aagcgcgcgc gccctggaac   1860
atctgtccct cgaagctgct acaagaagaa cttttcacac ctttcacttg ctaaacgagg   1920
ggctgagtgc tggtgcaagg agtatgtttt ggaccccaag ggacttcagc atcagagtat   1980
caaggctcct cctcccactt ttcttaacat tgattccctt gcccaaacta tgaaacaaga   2040
cttcattctt aagaacatgg catttgaggc agagaatggc tctagtgagc acaggtttgg   2100
ctttgtctgt cagcagagtg aggtcgacac tgttcgcagg ctgcttaatg caataagggc   2160
acggcttaac gcgacattca ctgtgtgcgt tgggcctgag tcctcaaatt ccattgggtg   2220
tactgctcat gtcctcactc ccgatgagcc tttcaatggg aagaggtttg ttgtatctcg   2280
atgcaacgaa gcctcccttg cagcactaga aggaaattgc gtgcagactg cgttgggcgt   2340
atgcatgtcc aacaaggatt taacccacct gtgccatttc ataagaggga agattgtcaa   2400
tgatagtgtc aggctggacg aactacccgc caatcaacat gtggtaaccg tgaattcggt   2460
atttgatttg gcctgggctc ttcgccgtca cctcacacta tctggacagt ttcaagcaat   2520
cagagccgca tatgatgtgc taactgtccc cgacaaaatt ccagctatgt taaggcactg   2580
gatggatgaa acatcctttt cggatgagca tgtagtcaca cagtttgtaa cgccaggtgg   2640
tattgtcatc ttggaatcat gtggtggagc acgtatctgg gctttgggtc acaatgtgat   2700
ccgcgctgga ggtatcactg caacaccaac tggtggttgt gtcagattaa tgggtctctc   2760
tgccccttct atgccatggt ctgaactctt tcgagaactt ttctctttat tgggtaggat   2820
atggtctagt gttaaagtct ccactcttgt tctgaccgct cttggaatgt acgcatctag   2880
```

```
atttagaccc aaatcagaag ctaagggaaa aacaaaatcc aaggttgggc cctacagagg   2940
tcgtggtgta gcgctcactg atgatgagta cgatgaatgg agggaacaca acgccacacg   3000
aaaattggac ttatcagtag aagattttct gatgctgcgc catcgtgcag cacttggtgc   3060
tgatgatgca gatgcagtta aatttagatc atggtggaac tcaagatcaa aattggcgga   3120
tgattttgaa gatgtcaccg tgattggaaa aggtggtgtt aaacatgaaa gaatcagaac   3180
aaacaatctc agagctgtgg agcgtggata tgacgttagc tttgctgaag aatcaggacc   3240
cggcacaaaa ttccacaaaa acgccattgg atctgtaact gatgtttgtg gtgagcacaa   3300
gggatactgt gtccatatgg gtcatggggt gtacgcctca gtagcccatg tggtgaaagg   3360
tgattcattc tttcttggtg agagaatatt tgacctcaaa actaatggtg agttttgctg   3420
ctttcgcagt acaaagatct tgcccagtgc tgcgcctttc ttctcaggca aacccacccg   3480
tgacccgtgg ggctcacctg ttgccacaga atggaagcca aaaccataca ccactacatc   3540
agggaagatt atagggtgtt ttgctacaac ttcaactgaa acccacccag gtgattgtgg   3600
tctaccttac atcgatgaca atggtagagt cactggactg cacacaggat ccggtggacc   3660
caaaactccc agcgcaaaat tggttgtccc ctatgtccat attgatatga aaacaaaatc   3720
tgttactgcc caaaagtatg acattacaaa gcctgatatt agttacaaag gattgatttg   3780
caaacaattg gatgaaattc ggataatacc aaaaggaaca cgcctccacg tttctcctgc   3840
ccacacagat gattatgagg aatgttcgca ccaaccagca tcactaggta gtggtgatcc   3900
acgatgtcca aaatccctta ctgctattgt agttgactcc ttaaaaccct actgtgataa   3960
ggttgagggc cccccccatg atgttttgca tagggttcag aaaatgctaa ttgatcacct   4020
ctctggcttt gttcctatga atatctcttc tgaaaactca atgctctctg catttcacaa   4080
actcaatcat gatacatcct gtggcccata cttaggtgga agaaagaaag atcatatggt   4140
aaatggtgag cctgacaagg cactgttgga tttgctatct tcaaaatgga aacttgccac   4200
tcaagggatt gctctccctc atgagtacac aattgggcta aaagatgaat tgagaccaat   4260
tgagaaagtt caggaaggaa agagaaggat gatctggggt tgtgatgttg gggttgccac   4320
agtttgcgct gctgcattta aaggtgttag tgacgcaata acggcaaacc accagtatgg   4380
acctgttcaa gttgggatta acatggatag ccccagtgtt gaggcacttt accaacgaat   4440
caagagcgct gccaaggttt ttgcggtcga ttactccaag tgggattcga ctcaatcgcc   4500
tcgggttagt gctgcctcaa ttgatattct tagatacttc tctgatagat ctccaattgt   4560
tgattcagct gcaaacacct taaaaagtcc tccaatagcg gtgttcaatg gtgttgcagt   4620
aaaggtttcg tctggtcttc catctggtat gcctctgact tctgtaatta actctttaaa   4680
tcactgccta tatgttggtt gtgctatcct tcaatctctg gaatccaaaa acatacctgt   4740
cacttggaat ctgttctcct catttgacat gatgacttac ggtgatgatg gtgtttacat   4800
gttccctatc atgtttgcta gtgttagtga tcaaatcttt ggaaacctta ctgcttatgg   4860
cttaaaaccc acaagggtcg acaaatcagt tggagctatt gaaccaatcg atcctgaatc   4920
tgttgttttc ctaaaaagaa ccatccaaag gacccctagt ggcattcgag gtcttcttga   4980
tcgcagctca atcctcagac agttctatta cattaaaggt gaaaattcgg atgattggaa   5040
aactcctcca aaagtcatag atcccacctc cagaggtcaa cagctgtgga acgcttgtct   5100
ttatgctagc caacatggtg ttgagtttta caataaggtt ctcaaattgg cccagaaagc   5160
tgttgaatac gaaggattac acctcgaccc cccaagcttc caatcggcat tggaacatta   5220
```

caataaccaa tttagtggtg tggaggcgcg gaatgaccag atcgattcga gtggcatgtc 5280
cgccctacac tgtgatgtgt tcgaagtttg agcatgtgct caacctgcgc taacgtgctt 5340
aaatactatg attgggatcc ccacttcaaa ttggtgatcg accctaataa atttctttct 5400
gttggattct gtgataaccc gcttatgtgt tgctatcctg agttgcttcc agaattcggc 5460
actgtgtggg attgtgatca atctccactg caaatttacc ttgaatctat tcttggtgat 5520
gatgaatggt cttctaccta tgaagccatt gaccctgtcg ttccaccaat gcactgggac 5580
aaaatgggga aaatcttcca acctcaccct ggtatgctaa tgcaccatat catcggtgaa 5640
gttgccaagg gatgggatcc aaacttgcct ttgttccgat tggaggccga tgatggatcg 5700
gtgacaaccc ctgaacaagg aacaatggtt ggcggagtca ttgctgaacc cagcgcccaa 5760
atgtcaactg ctgctgacat ggcctctggg aaaagtgttg actccgaatg ggaggctttc 5820
ttctcatttc acactagtgt aaattggagt acatctgaaa cacaaggaaa gattctattc 5880
aaacaatcac ttggacccct gctaaaccca tatcttgaac acatatctaa gctttatgtt 5940
gcatggtctg gatctataga ggttaggttt tctatttctg gttctggtgt ttttggggga 6000
aaactcgctg ctattgttgt gccgcctggg gtagacccag tgcaaagcac atcaatgcta 6060
cagtatcctc atgttctatt tgatgcccgt caggtagaac ctgttatctt ttcaatacct 6120
gatttgagaa acagcttgta ccatcttatg tcagatactg atactacctc ccttgtaatt 6180
atggtgtaca atgatcttat taatccttat gcaaatgatt ctaactcttc tggatgtatt 6240
gtcactgttg agactaaacc tggaatcgat ttcaagtttc accttctgaa accccctgga 6300
tctatgctta cccatggctc tatcccttca gatttaatac caaaatcttc ttctctttgg 6360
atagggaatc gtcactggac tgacataacc gattttgtca ttaggccttt tgtgttccaa 6420
gcaaaccgtc attttgattt taatcaggaa acagctggtt ggagtacgcc aagattccga 6480
ccactagccg taacggttag ccaaagtaaa ggagcaaaat tggggaatgg tattgcgacc 6540
gactacatcg tgcctgggat tcctgatgga tggccagaca ctacaatccc aacaaaactg 6600
acacccacag gcgattatgc aattacatct agtgatggta atgacattga aacaaaactt 6660
gaatacgaaa atgctgatgt gattaaaaac aacacaaact tcaggagcat gtacatttgt 6720
gggtcgctcc aaagagcctg ggtgataag aagatttcta atactggttt cataactact 6780
ggtgttatct ctgataattc cataagccca agcaatacca ttgatcaaag caaaatcgtg 6840
gtctatcaag acaatcatgt caatagtgaa gttcaaacct cagacatcac acttgcaatt 6900
cttggctaca ctggtattgg tgaggaggca attggcgcca atcgggactc ggttgtacgc 6960
ataagtgtgc tgccagaaac aggtgcccgt gggggaaacc atccaatctt ttataagaat 7020
tctatgaagc ttggttacgt gatcagctcc attgatgtgt ttaattccca gatcttgcac 7080
acctctagac aactatcact gaataactac ttactacctc cagattcttt tgctgtctat 7140
cgaattattg attctaatgg gtcttggttt gatataggca ttgattctga tggattttct 7200
tttgttggtg tctcaagttt tcctaagtta gagtttccac tttctgcctc ctatatggga 7260
attcagttgg caaagattcg tcttgcctct aatattagga gttctatgac taaattatga 7320
attcaatatt aggcttaatt gacactgtta caaatacaat tggcaaagct caacaaattg 7380
aattagataa agctgcactt ggtcaacaac gcgaactggc tttgcaacga attaaccttg 7440
atcgccaggc gttgaacaac caagttgagc aatttaacaa aattcttgag caaagggtac 7500
aaggccccat ccagtctgtg cggctcgcac gtgctgctgg atttagggtt gacccttact 7560
catacacaaa tcaaaatttt tacgatgacc aattgaatgc aattagacta tcttatagga 7620

```
atttgtttaa ataattggcc acaagtatcc cttcgggctg ccgcatttgc gcctaacccc   7680

agggc                                                               7685


<210> SEQ ID NO 60
<211> LENGTH: 7690
<212> TYPE: DNA
<213> ORGANISM: Feline calicivirus

<400> SEQUENCE: 60

gtaaaagaaa tttgagacaa tgtctcaaac tctgagcttc gtgcttaaaa ctcacagtgt     60

ccgaaaggac tttgtgcact ctgtcaagtt aacacttgca cggaggcgcg atcttcagta    120

tatttataac aagctctcac gcactatacg tgctgaggct tgcccttctt gtgctagtta    180

cgacgtatgt cctaactgca cctctggtga cgtcccggat gacgggtctt cgacaatgtc    240

gattccatca tgggaggatg tcacaaagtc ttcaacctac tctctcctgc tctctgagga    300

cacctccgac gagttatgcc ctgaggactt ggttaatgtg gctgctcata tccgtaaggc    360

gctatccact cagtcccacc cggctaatgc tgaaatgtgc aaagaacagc tcactttctt    420

attagtcatg gctgaggcga tgctgcccca acgatcccga gcgtcaatcc cactgcacca    480

acaacacacg gctgcacggt tggaatggag ggagaaattc ttctctaaac ctcttgactt    540

tctccttgaa agagttggtg tgtcaaaaga tattctccaa actactgcga tttggaaaat    600

tatcttggaa aaagcatgct attgtaaatc ctatggagag cagtggttca ctgctgccaa    660

acaaaagtta agggaaatga aaaactttga gagtgatacg ctaaaacctc ttattggtgg    720

atttatagat ggtctacggt tcttgaccgt ggacaaccca aacccgatgg gtttcctccc    780

aaaactcata gggcttgtaa aacccctgaa tttggcgatg attattgata atcatgaaaa    840

cacaatatct ggctggatca tcacattaac cgcaataatg gagctataca acatcaccga    900

atgcaccata gatattataa catcagtcat tacggctttc tatgataaaa ttggcaaggc    960

aaccaaattt tacagttgtg ttaaggcgct gttcactgga tttagatctg aggacgtagc   1020

gaattccttt tggtacatgg cagcagcgat tctatgttac ctgatcactg ggttaatccc   1080

aaacaacggc agattttcaa agataaaagc ttgcctggcc ggagcgacaa ctcttgtatc   1140

aggtatagtt gccacacaaa agctagctgc aatgttcgca acatggaact ctgagtccat   1200

tgttaatgag ttgtcagcaa gaactgttgc cctatcagag ctaaacaatc caacaacaac   1260

gtctgacacg gattcggtag aacgactgct agaattggct aagatcttgc atgaggagat   1320

caagattcat actctaaacc ccatcatgca atcatacaat ccaatcttga gaaatttaat   1380

gtcaaccttg gacggtgtta taacatcatg caacaagagg aaagctattg ctcggaagag   1440

acaggtgcca gtttgttaca tattaactgg cccacctgga tgtgggaaaa caaccgcagc   1500

tcaagcatta gctaagaaat tgtctgatca agagccgtcg gtaattaacc ttgatgttga   1560

tcatcatgac acatatactg gaaatgaggt atgtatcatt gatgagtttg attcgtctga   1620

caaggtagac tatgcaaatt ttgtgattgg gatggtaaac tctgctccta tggtgttaaa   1680

ttgtgacatg cttgagaaca agggaaagct cttcacctca aagtatataa ttatgacttc   1740

caactctgaa actccagtga aaccctcttc caagcgcgca ggtgcattct accgaagggt   1800

tactatcatc gatgtaacta acccttttgt ggagtcgcac aagcgtgcaa ggcctgggac   1860

gtctgttcct cgtagctgct ataagaaaaa cttctcccat ctctcacttg ctaaacgagg   1920

ggccgagtgc tggtgcaagg aatacgttct tgaccctaag ggcttcaac accaaagcat    1980
```

-continued

```
gaaggctccc cctcctacct ttcttaacat tgactcttta gctcagacga tgaagcaaga   2040
cttcttgctc aagaacatgg cttttgaggc tgaagatggg tgcgcagaac atcgatatgg   2100
gtttgtgtgt caacaggaag aggttgaaac tgttcgcagg ctcctcaacg cggttagggc   2160
aaggatgaat gctaccttca ctgtgtgtgt tggacccgag acctcgcact cgattggttg   2220
cactgcgcac gtgttaactc ccaatgagac ctttaatgga aagaagtttg ttgtgtcacg   2280
atgtaacgaa gcatcacttt ctgcccttga aggtaactgt gtaaagtcag ctttgggcgt   2340
gtgtatgtca gataaggatc tcactcattt atgccacttc attaaaggga aaattgtcaa   2400
tgacagtgtt aggttggatg aactacccgc caatcagcat gtggtaaccg ttaattcggt   2460
gtttgatttg gcctgggctg ttcgtcgtca tctcacactg gcagggcagt ttcaagctat   2520
cagagccgca tatgatgtgc ttactgtccc cgacaagatc cctgcaatgt tgcgtcactg   2580
gatggatgag acctcctttt ctgatgacca cgttgtaaca caatttgtaa cacctggtgg   2640
catagtcatc ctggagtctt gcggtggtgc acgcatctgg gctttaggtc gcaacgtgat   2700
ccgagcagga ggtgtcaccg caaccccaac cggaggatgt gttaggttaa tgggattatc   2760
tgcgccaacc atgccatggt ccgagatctt tcgtgagctc ttctctctct taggtagaat   2820
ttggtcatct gtcaaagtat cagccctagt actaactgct cttggaatgt acgcatctag   2880
atttagacca aaatcggaag caaaaggaaa aaccaaattg aagattggga catacagggg   2940
tcgcggtgta gcgctgactg atgacgagta cgatgagtgg cgcgaacaca acgcctccag   3000
aaaattggat ttgtcagtgg aggatttctt aatgttgcgc catcgtgccg ctctaggagc   3060
cgacgacaat gatgcagtaa aattccggtc gtggtggaac tccagaacca aaatggccaa   3120
tgattatgag gatgtcaccg taattggcaa aggtggcgtc aaacatgaaa agatcagaac   3180
caatacccta aaagctgtgg atcgtggtta tgacgtcagc tttgctgagg aatcaggacc   3240
aggcaccaag ttccacaaga atgcaattgg atctgtcaca gatgtttgtg gggagcacaa   3300
aggctattgc atccacatgg gccacggtgt ttacgcatcc gtagctcacg tggtgaaagg   3360
ggattcattt ttcttgggtg aaaggatttt tgatcttaag actaatggtg aattttgctg   3420
ctttcgcagc acgaaaattc tacctagtgc tgcacctttc ttttctggga agcccactcg   3480
tgatccgtgg ggatcccccg tggcaactga gtggaagcct aaaatgtaca caacaacctc   3540
tggaaagatt ctggggtgct ttgcaacaac ttcaactgaa actcacccgg gagactgtgg   3600
cctcccatat attgatgaca acgggagggt gaccggcctc cacactggct ctgggggacc   3660
caaaacccca agtgccaagt tggtggtgcc atatgtgcat attgacatga agactaaatc   3720
cgtcactgct caaaagtatg acgtaacaaa gcctgatata agttacaaag gcttaatttg   3780
taagcaattg gatgagatta ggattatacc aaaaggcaca cgtctccatg tctccccagc   3840
ccacactgag gattatcaag aatgctcaca ccaacccgca tcacttggaa gcggggatcc   3900
ccgctgtcca aaatctctca ctgctatagt tgttgattct ctaaaaccat actgtgagaa   3960
cgttgagggt cctccacatg atgttttgca cagagttcaa aagatgctta tcgaccacct   4020
ttcaggcttt gtccctatga acatttcctc ggaaacctct atgctctcag ctttccacaa   4080
actcaatcat gatacttcct gtggaccata cttgggtggc agaaagaaag atcacatggc   4140
taacggtgag ccggacaagc agttattgga tctcctgtct gcaaaatgga aattggcaac   4200
ccaaggcata gcactaccac atgagtacac aattgggcta aaggacgagt taaggcccgt   4260
ggagaaggtt agtgaaggga agagaaggat gatttggggt tgtgatgttg gcgtcgctac   4320
tgtctgtgca gctgcgttca agggtgttag cgatgccatc acagcaaacc accagtacgg   4380
```

-continued

```
gcctatacag gttggtatca acatggatag ccccagcgtc gaagcgctgt tccaaaggat   4440
caaaagcgcg gccaaggtat ttgcggtcga ttattccaaa tgggattcga cccaatcgcc   4500
tcgtgtcagt gcagcttcaa ttgacatcct tcgttacttt tccgatcgct ctccaattgt   4560
tgactcagcc tctaacacac tgaagagccc tcctgttgca atctttaatg gtgttgctgt   4620
aaaagtgtcc tctggcttac catctggaat gcctcttacc tcagtaatca attcccttaa   4680
tcattgtctg tatgttgggt gtgccattct tcaatcccta gaagctaagg ccattcccgt   4740
cacttggaac cttttctcaa cttttgatat catgacttac ggggatgatg gtgtctacat   4800
gtttcctatt atgtatgcaa gtattagtga ccaaattttt ggaaatcttt cttcctatgg   4860
cctgaaacca actcgggttg acaagtccgt tggagcaatt gagcctattg atcctgactc   4920
tgttgttttc ttgaagagaa caatcacaag gacacctcag ggataagggg gtttacttga   4980
tcgcagctct ataataagac aattctatta tattaaaggt gagaactccg atgactggaa   5040
gagccccccca aaacatattg acccaacatc tcgagggcaa cagctttgga atgcctgtct   5100
gtacgctagc caacatggct tggagttttt caacaaggtt tacaggctgg ccgagagggc   5160
tgttgaatat gaagagctgc actttgaacc cccaacatat gcttcggctt tggatcatta   5220
caacagccag ttcaatggcg tggaggcgcg gtctgaccag atcgactcga gtggcatgac   5280
cgccctacac tgtgatgtgt tcgaagtttg agcatgtgct caacctgcgc taacgtgctt   5340
aaatattatg attgggaccc ccatttcaaa ttggtaatca accccaacaa cttcctctct   5400
gttggctttt gtagtaaccc tttaatgtgt tgctacccag aactccttcc ggaatttgga   5460
actgtttggg attgcgatcg gtcaccactt gaaatttacc tagaatcaat acttggtgat   5520
gatgaatggg catccacttt tgacgctgtt gacccagtcg ttccccccaat gcactggggt   5580
gctgctggaa aaattttcca gccacacccc ggtgttctca tgcaccatct cattggtaag   5640
gttgctgcag gttgggaccc cgatctgcct ctaattcgac tcgaggcgga tgacgggtca   5700
atcacagcac ccgagcaagg aacaatggtt ggcggcgtca tcgctgaacc cagcgcccag   5760
atgtcaacag ctgctgatat ggccaccggg aaaagcgttg attctgagtg ggaggcattc   5820
ttctcctttc acaccagcgt caattggagt acatctgaaa cccaaggaaa gattctcttc   5880
aaacaatcct taggcccttt gctcaaccca tatctagaac accttgctaa gctatatgtt   5940
gcgtggtctg ggtcgattga ggttaggttc tctatctctg gctctggtgt ctttggtggg   6000
aagctcgcag ctattgttgt acctcctggg gttgatccag tgcagagtac ttcgatgcta   6060
caatacccc atgttttgtt tgatgctcgt caggtggaac cagttatctt ctgtcttcct   6120
gatctaagaa gcaccctgta ccaccttatg tctgacactg acactacatc cttggtcatt   6180
atggtgtaca atgatctcat caatccctat gccaatgatg ccaactcttc tgggtgtatt   6240
gtcactgtcg agacaaaacc tggccctgac ttcaagtttc acctccttaa gccacccgga   6300
tctatgctaa cccatggctc tatcccttct gatttaattc ccaaaacatc ttcgctctgg   6360
atcggtaacc gctactggtc agacataact gattttgtga ttcggccgtt tgtcttccaa   6420
gcaaatcgtc attttgactt taatcaagag accgcagggt ggagcacacc acggtttcgg   6480
cctatatctg ttaccattac tgaacagaac ggagcaaaat tgggcattgg ggtggcaaca   6540
gattacatag tgcctggaat ccctgatggc tggcctgaca ccacaattcc tggggagttg   6600
ataccagctg gtgattacgc aatcaccaat ggtactggca atgacatcac cacggctaca   6660
ggatatgaca ctgctgatat aattaagaac aataccaact ttaggggcat gtacatatgt   6720
```

-continued

```
ggttcgctcc agcgtgcctg gggtgataag aaaatttcca acactgcctt tatcaccact   6780

gccaccctag atggtgacaa caacaacaag atcaatccct gtaataccat agaccagtca   6840

aagatcgtcg tgtttcaaga caaccatgtt ggaaagaaag cgcaaacctc agacgataca   6900

ttggccctgc ttggttacac tggcattggt gagcaggcca tcgggtctga tagggaccgg   6960

gttgtgcgca tcagcactct ccctgaaact ggtgctcgag gcggtaacca cccaattttc   7020

tacaagaact ccattaaatt gggatatgta attaggtcta ttgatgtctt taattcacaa   7080

atcttgcaca cttccagaca gttatcgcta aatcattacc tactcccacc tgattctttt   7140

gccgtctata gaataattga ctcaaatggc tcgtggtttg atattggaat tgatagtgat   7200

gggttctctt ttgttggtgt ttctggcttt ggtaaattag aatttcccct ttctgcctcc   7260

tacatgggaa tacaattggc aaagatccgg cttgcctcta acattaggag tcccatgact   7320

aagttatgaa ttcaatatta ggcctgattg atactgttac taacactatt ggtaaagctc   7380

agcagattga attggacaaa gctgcacttg gtcaacagcg tgaattggct ctccagcgca   7440

ttggcttgga ccgccaagcc ttaaacaacc aagttgagca gtttaacaaa attcttgagc   7500

aaagggtaca aggcccaatc caatccgttc gccttgcgcg cgcggctgga tttagggttg   7560

acccttactc atacacaaac caaaactttt atgacgatca attaaatgca attagactat   7620

catataaaaa tttgtttaaa atttgatcat atatcccttt gggctgccgc acctgcgcct   7680

aaccccaggg                                                          7690
```

<210> SEQ ID NO 61
<211> LENGTH: 7690
<212> TYPE: DNA
<213> ORGANISM: Feline calicivirus

<400> SEQUENCE: 61

```
gtaaaagaaa tttgagacaa tgtctcaaac tctgagcttc gtgcttaaaa ctcacagcgt     60

ccgcaaggac tttgtgcact ccgtcaagct aacgcttgca cggaggcgcg atcttcagta    120

tttctataac aagctctctc gttctatgcg agctgaagct tgtccttctt gtgccagtta    180

tgatgtatgt cctaactgca cttctagtga tatccctgat gatggttcat caacaacgtt    240

gatgccatca tgggaggatg tcacaaaaac ctctacttac tctcttctac tctccgaaga    300

tacttctgac gagttgtctc ctgacgaatt ggttcacgtt gctgctcaca ttcgcaaggc    360

gctttccact cagtctcatc cggccaatgt tgacatgtgc aaagaacagc tcacgtcatt    420

attggtgatg gctgaagcta tgctgcctca acggtcacga gcaacaatcc cacttcatca    480

acaacaccag acggctcgca ttgaatggag ggaaaagttc ttctctaagc cccttaactt    540

cattcttgaa aagattggtg tttctaaaga tattcttcag gttactgccc tttggaaaat    600

catcttggag aaagcttgct actgcaaatc ctatggtgaa gagtggttcg atgctgcaaa    660

gaacaaacta agggagatga gaagcttcga aagcaacaca ctcaaaccac tggttggagc    720

tttcattgac ggcttaaggt ttatgactgt ggataacccc aaccctatgg cattcttacc    780

caagctaatt gggcttatca aacccctcaa tttggcaatg ataatcgaca atcatgaaaa    840

cacactatca ggatggatca ttaccctcac tgcaattatg gagttataca acatcacaga    900

atgcacaatt gacataatca cttcactggt aacagcattc tatgacaaaa ttgctaaagc    960

ccctaaattc tacagtcaga tcaaagcact gttcacggga tttaggacag aggatgtggc   1020

taattcattt tggtatatgg ctgctgcaat tctatgttac ctgattacgg gtataatccc   1080

aaacaatggg aggttttcaa agattaaaac ctgcctgtct ggtgcaacga ccctggtatc   1140
```

-continued

```
gggtataatt gccacacaga aacttgcagc aatgttcgct acatggaact ctgaatccat   1200
tgttaacgaa ttatctgcaa ggacagtggc tatttctgaa ttgaataacc caactactac   1260
ctctgacact gactctgttg agcggttgct cgaattggct aagatcttgc acgaggagat   1320
caaagttcac actctgaatc caattatgca atcatacaac ccaattctta gaaatttaat   1380
gtccacacta gacggtgttg tcacctcatg caacaagaga agagcaattg ccaaaaagag   1440
gcaagtccca gtttgctaca tccttactgg accacctgga tgtggcaaga ccactgcggc   1500
cctagccctt gcaaagaagc tctctgatca agagccatca gtgattaatt tggatgttga   1560
tcatcatgat acttacactg gcaatgaagt gtgcattgtt gatgagtttg attcatcaga   1620
caaagtggac tatgcaaatt ttgtgattgg tatggttaat tcggcaccaa tggttctaaa   1680
ttgtgatatg cttgaaaata agggaaagct ctttacctct aagtacataa taatgacttc   1740
taactctgaa acccctgtaa aaccctcttc taagcgtgca ggtgctttct accgaagagt   1800
tacaatcatt gacgttgcaa acccttggt ggaatctcac aagcgcgcgc gccctggaac   1860
atctgtccct cgaagctgct acaagaagaa cttttcacac ctttcacttg ctaaacgagg   1920
ggctgagtgc tggtgcaagg agtatgtttt ggaccccaag ggacttcagc atcagagtat   1980
caaggctcct cctcccactt ttcttaacat tgattccctt gcccaaacta tgaaacaaga   2040
cttcattctt aagaacatgg catttgaggc agagaatggc tctagtgagc acaggtttgg   2100
ctttgtctgt cagcagagtg aggtcgacac tgttcgcagg ctgcttaatg caataagggc   2160
acggcttaac gcgacattca ctgtgtgcgt tgggcctgag tcctcaaatt ccattgggtg   2220
tactgctcat gtcctcactc ccgatgagcc tttcaatggg aagaggtttg ttgtatctcg   2280
atgcaacgaa gcctcccttg cagcactaga aggaaattgc gtgcagactg cgttgggcgt   2340
atgcatgtcc aacaaggatt taacccacct gtgccatttc ataagaggga agattgtcaa   2400
tgatagtgtc aggctggacg aactacccgc caatcaacat gtggtaaccg tgaattcggt   2460
atttgatttg gcctgggctc ttcgccgtca cctcacacta tctggacagt ttcaagcaat   2520
cagagccgca tatgatgtgc taactgtccc cgacaaaatt ccagctatgt taaggcactg   2580
gatggatgaa acatcctttt cggatgagca tgtagtcaca cagtttgtaa cgccaggtgg   2640
tattgtcatc ttggaatcat gtggtggagc acgtatctgg gctttgggtc acaatgtgat   2700
ccgcgctgga ggtatcactg caacaccaac tggtggttgt gtcagattaa tgggtctctc   2760
tgccccttct atgccatggt ctgaactctt tcgagaactt ttctctttat tgggtaggat   2820
atggtctagt gttaaagtct ccactcttgt tctgaccgct cttggaatgt acgcatctag   2880
atttagaccc aaatcagaag ctaagggaaa aacaaaatcc aaggttgggc cctacagagg   2940
tcgtggtgta gcgctcactg atgatgagta cgatgaatgg agggaacaca acgccacacg   3000
aaaattggac ttatcagtag aagattttct gatgctgcgc catcgtgcag cacttggtgc   3060
tgatgatgca gatgcagtta aatttagatc atggtggaac tcaagatcaa aattggcgga   3120
tgattttgaa gatgtcaccg tgattggaaa aggtggtgtt aaacatgaaa gaatcagaac   3180
aaacaatctc agagctgtgg agcgtggata tgacgttagc tttgctgaag aatcaggacc   3240
cggcacaaaa ttccacaaaa acgccattgg atctgtaact gatgtttgtg gtgagcacaa   3300
gggatactgt gtccatatgg gtcatggggt gtacgcctca gtagcccatg tggtgaaagg   3360
tgattcattc tttcttggtg agagaatatt tgacctcaaa actaatggtg agttttgctg   3420
ctttcgcagt acaaagatct tgcccagtgc tgcgcctttc ttctcaggca aacccacccg   3480
```

```
tgacccgtgg ggctcacctg ttgccacaga atggaagcca aaaccataca ccactacatc   3540
agggaagatt atagggtgtt ttgctacaac ttcaactgaa acccacccag gtgattgtgg   3600
tctaccttac atcgatgaca atggtagagt cactggactg cacacaggat ccggtggacc   3660
caaaactccc agcgcaaaat tggttgtccc ctatgtccat attgatatga aaacaaaatc   3720
tgttactgcc caaaagtatg acattacaaa gcctgatatt agttacaaag gattgatttg   3780
caaacaattg gatgaaattc ggataatacc aaaaggaaca cgcctccacg tttctcctgc   3840
ccacacagat gattatgagg aatgttcgca ccaaccagca tcactaggta gtggtgatcc   3900
acgatgtcca aaatccctta ctgctattgt agttgactcc ttaaaaccct actgtgataa   3960
ggttgagggc ccccccatg atgttttgca tagggttcag aaaatgctaa ttgatcacct   4020
ctctggcttt gttcctatga atatctcttc tgaaaactca atgctctctg catttcacaa   4080
actcaatcat gatacatcct gtggcccata cttaggtgga agaaagaaag atcatatggt   4140
aaatggtgag cctgacaagg cactgttgga tttgctatct tcaaaatgga aacttgccac   4200
tcaagggatt gctctccctc atgagtacac aattgggcta aaagatgaat tgagaccaat   4260
tgagaaagtt caggaaggaa agagaaggat gatctggggt tgtgatgttg gggttgccac   4320
agtttgcgct gctgcattta aaggtgttag tgacgcaata acggcaaacc accagtatgg   4380
acctgttcaa gttgggatta acatggatag ccccagtgtt gaggcacttt accaacgaat   4440
caagagcgct gccaaggttt ttgcggtcga ttactccaag tgggattcga ctcaatcgcc   4500
tcgggttagt gctgcctcaa ttgatattct tagatacttc tctgatagat ctccaattgt   4560
tgattcagct gcaaacacct taaaaagtcc tccaatagcg gtgttcaatg gtgttgcagt   4620
aaaggtttcg tctggtcttc catctggtat gcctctgact tctgtaatta actctttaaa   4680
tcactgccta tatgttggtt gtgctatcct tcaatctctg gaatccaaaa acatacctgt   4740
cacttggaat ctgttctcct catttgacat gatgacttac ggtgatgatg gtgtttacat   4800
gttccctatc atgtttgcta gtgttagtga tcaaatcttt ggaaacctta ctgcttatgg   4860
cttaaaaccc acaagggtcg acaaatcagt tggagctatt gaaccaatcg atcctgaatc   4920
tgttgttttc ctaaaaagaa ccatccaaag gacccctagt ggcattcgag gtcttcttga   4980
tcgcagctca atcctcagac agttctatta cattaaaggt gaaaattcgg atgattggaa   5040
aactcctcca aaagtcatag atcccacctc cagaggtcaa cagctgtgga acgcttgtct   5100
ttatgctagc caacatggtg ttgagtttta caataaggtt ctcaaattgg cccagaaagc   5160
tgttgaatac gaaggattac acctcgaccc cccaagcttc caatcggcat tggaacatta   5220
caataaccaa tttagtggtg tggaggcgcg gaatgaccag atcgattcga gtggcatgac   5280
cgccctacac tgtgatgtgt tcgaagtttg agcatgtgct caacctgcgc taacgtgctt   5340
aaatattatg attgggaccc ccatttcaaa ttggtaatca accccaacaa cttcctctct   5400
gttggctttt gtagtaaccc tttaatgtgt tgctacccag aactccttcc ggaatttgga   5460
actgtttggg attgcgatcg gtcaccactt gaaatttacc tagaatcaat acttggtgat   5520
gatgaatggg catccacttt tgacgctgtt gacccagtcg ttcccccaat gcactggggt   5580
gctgctggaa aaattttcca gccacacccc ggtgttctca tgcaccatct cattggtaag   5640
gttgctgcag gttgggaccc cgatctgcct ctaattcgac tcgaggcgga tgacgggtca   5700
atcacagcac ccgagcaagg aacaatggtt ggcggcgtca tcgctgaacc cagcgcccag   5760
atgtcaacag ctgctgatat ggccaccggg aaaagcgttg attctgagtg ggaggcattc   5820
ttctcctttc acaccagcgt caattggagt acatctgaaa cccaaggaaa gattctcttc   5880
```

aaacaatcct taggcccttt gctcaaccca tatctagaac accttgctaa gctatatgtt 5940
gcgtggtctg ggtcgattga ggttaggttc tctatctctg gctctggtgt ctttggtggg 6000
aagctcgcag ctattgttgt acctcctggg gttgatccag tgcagagtac ttcgatgcta 6060 caatacccc atgtcttgtt tgatgctcgt caggtggaac cagttatctt ctctattcct 6120
gatctaagaa gcaccctgta ccaccttatg tctgacactg acactacatc cttggtcatt 6180
atggtgtaca atgatctcat caatccctat gccaatgatg ccaactcttc tgggtgtatt 6240
gtcactgtcg agacaaaacc tggccctgac ttcaagtttc acctccttaa gccacccgga 6300
tctatgctaa cccatggttc tgtcccttct gatttaattc ccaaaacatc ttcgctctgg 6360
atcggtaacc gctactggtc agacataact gattttgtga ttcggccgtt tgtcttccaa 6420
gcaaatcgtc attttgactt taatcaagag accgcagggt ggagcacacc acggtttcgg 6480
cctatatctg ttaccattac tgaacagaac ggagcaaaat tgggcattgg agtggcaaca 6540
gattacatag tgcctggaat ccctgatggc tggcctgaca ccacaattcc tggggagttg 6600
ataccagctg gcgattacgc aatcaccaat ggtactggca atgacatcac cacggctaca 6660
ggatatgaca ctgctgatat aattaagaac aataccaact ttaggggcat gtacatatgt 6720
ggttcgctcc agcgtgcctg gggtgataag aaaatttcca acactgcctt tatcaccact 6780
gccaccctag atggtgacaa caacaacaag atcaatccct gtaataccat agaccagtca 6840
aagatcgtcg tgtttcaaga caaccatgtt ggaaagaaag tgcaaacctc agacgataca 6900
ttggccctgc ttggttacac tggcattggt gagcaggcca tcgggtctga tagggaccgg 6960
gttgtgcgca tcagcactct ccctgaaact ggtgctcgag gcggtaacca cccaattttc 7020
tacaagaact ccattaaatt gggatatgta attaggtcta ttgatgtctt taattcacaa 7080
atcttgcaca cttccagaca gttatcgcta aatcattacc tactcccacc tgattctttt 7140
gccgtctata gaataattga ctcaaatggc tcgtggtttg atattggaat tgatagtgat 7200
gggttctctt ttgttggtgt ttctggcttt ggtaaattag aatttcccct ttctgcctcc 7260
tacatgggaa tacaattggc aaagatccgg cttgcctcta acattaggag tcccatgact 7320
aagttatgaa ttcaatatta ggcctgattg atactgttac taacactatt ggtaaagctc 7380
aacagattga attggacaaa gctgcacttg gtcaacagcg tgaattggct ctccagcgca 7440
ttggcttgga ccgccaagcc ttaaacaacc aagttgagca gtttaacaaa attcttgagc 7500
aaagggtaca aggcccaatc caatccgttc gccttgcacg cgcggctgga tttagggttg 7560
acccttactc atacacaaac caaaactttt atgacgatca attaaatgca attagactat 7620
catataaaaa tttgtttaaa atttgatcat atatcccttt gggctgccgc acctgcgcct 7680
aaccccaggg 7690

<210> SEQ ID NO 62
<211> LENGTH: 7684
<212> TYPE: DNA
<213> ORGANISM: Feline calicivirus
<220> FEATURE:
<221> NAME/KEY: misc_feature
<222> LOCATION: (5829)..(5829)
<223> OTHER INFORMATION: n is a, c, g, or t

<400> SEQUENCE: 62
gtaaaagaaa tttgagacaa tgtctcaaac tctgagcttc gtgcttaaaa ctcacagtgt 60
ccgaaaggac tttgtgcact ctgtcaagtt aacacttgca cggaggcgcg atcttcagta 120

-continued tatttataac aagctctcac gcactatacg tgctgaggct tgcccttctt gtgctagtta 180
cgacgtatgt cctaactgca cctctggtga cgtcccggat gacgggtctt cgacaatgtc 240
gattccatca tgggaggatg tcacaaagtc ttcaacctac tctctcctgc tctctgagga 300
cacctccgac gagttatgcc ctgaggactt ggttaatgtg gctgctcata tccgtaaggc 360
gctatccact cagtcccacc cggccaatgc tgaaatgtgc aaagaacagc tcacttcctt 420
attagtcatg gctgaggcga tgctgcccca acgatcccga gcgtcaatcc cactgcacca 480
acaacacacg gctgcacggt tggaatggag ggagaaattc ttctctaaac ctcttgactt 540
tctccttgaa agagttggtg tgtcaaaaga tattctccaa actactgcga tttggaaaat 600
tatcttggaa aaagcatgct attgtaaatc ctatggagag cagtggttca ctgctgccaa 660
gcaaaagtta agggaaatga aaaactttga gagtgatacg ctaaaacctc ttattggtgg 720
atttatagat ggtctacggt tcttgaccgt ggacaaccca aacccgatgg gtttcctccc 780
aaaactcata gggcttgtaa aacccctgaa tttggcgatg attattgata atcatgaaaa 840
cacaatatct ggctggatca tcacattaac cgcaataatg gagctataca acatcaccga 900
atgcaccata gatattataa catcagtcat tacggctttc tatgataaaa ttggcaaggc 960
aaccaaattt tacagttgtg ttaaggcgct gttcactgga tttagatctg aggacgtagc 1020
gaattccttt tggtacatgg cagcagcgat tctatgttac ctgatcactg ggttaatccc 1080
aaacaatggc agattttcaa agataaaagc ttgcctggcc ggagcgacaa ctcttgtatc 1140
aggtatagtt gccacacaaa agctagctgc aatgttcgca acatggaact ctgagtccat 1200
tgttaatgag ttgtcagcaa gaactgttgc cctatcagag ctaaacaatc caacaacaac 1260
gtctgacacg gattcggtag aacgactgct agaattggct aagatcttgc atgaggagat 1320
caagattcat actctaaacc ccatcatgca atcatacaat ccaatcttga gaaatttaat 1380
gtcaaccttg gacggtgtta taacatcatg caacaagagg aaagctattg ctcggaagag 1440
acaggtgcca gtttgttaca tattaactgg cccacctgga tgtgggaaga caaccgcagc 1500
tcaagcatta gctaagaaat tgtctgatca agagccgtcg gtaattaacc ttgatgttga 1560
tcatcatgac acatatactg gaaatgaggt atgtatcatt gatgagtttg attcgtctga 1620
caaggtagac tatgcaaatt ttgtgattgg gatggtaaac tctgctccta tggtgttaaa 1680
ttgtgacatg cttgagaaca agggaaagct cttcacctca aagtatataa ttatgacttc 1740
caactctgaa actccagtga aacccctcttc caagcgcgca ggtgcattct accgaagggt 1800
tactatcatc gatgtaacta accctttggt ggagtcgcac aagcgtgcaa ggcctgggac 1860
gtctgttcct cgtagctgct ataagaaaaa cttctcccat ctctcacttg ctaaacgagg 1920
ggccgagtgc tggtgcaagg aatacgttct tgaccctaag ggcttcaac accaaagcat 1980 gaaggctccc cctcctacct ttcttaacat tgactcttta gctcagacga tgaagcaaga 2040
cttcttgctc aagaacatgg cttttgaggc tgaagatggg tgcgcagaac atcgatatgg 2100
gtttgtgtgt caacaggaag aggttgaaac tgttcgcagg ctcctcaacg cggttagggc 2160
aaggatgaat gctaccttca ctgtgtgtgt tggacccgag acctcgcact cgattggttg 2220
cactgcgcac gtgttaactc ccaatgagac ctttaatgga aagaagtttg ttgtgtcacg 2280
atgtaacgaa gcatcacttt ctgcccttga aggtaactgt gtaaagtcag ctttgggcgt 2340
gtgtatgtca gataaggatc tcactcattt atgccacttc attaaaggga aaattgtcaa 2400
tgacagtgtt aggttggatg aactacccgc caatcagcat gtggtaaccg ttaattcggt 2460
gtttgatttg gcctgggctc ttcgtcgtca tctcacactg gcagggcagt ttcaagctat 2520

```
cagagccgca tatgatgtgc ttactgtccc cgacaagatc cctgcaatgt tgcgtcactg   2580
gatggatgag acctcctttt ctgatgacca cgttgtgaca caatttgtaa cacctggtgg   2640
catagtcatc ctggagtctt gcggtggtgc acgcatctgg gctttaggtc acaacgtgat   2700
ccgagcagga ggtgtcaccg caaccccaac cggaggatgt gttaggttaa tgggattgtc   2760
tgccccaacc atgccatggt ccgagatctt tcgtgagctc ttctctctct taggtagaat   2820
ttggtcatct gtcaaagtat cagccctagt actaactgct cttggaatgt acgcatctag   2880
atttagacca aaatcggaag caaaaggaaa aaccaaattg aagattggaa catacagggg   2940
tcgcggtgta gcgctgactg atgacgagta cgatgagtgg cgcgaacaca acgcctccag   3000
aaaattggat ttgtcagtgg aggatttctt aatgttgcgc catcgtgccg ctctaggagc   3060
cgacgacaat gatgcagtaa aattccggtc gtggtggaac tccagaacca aaatggccaa   3120
tgattatgag gatgtcaccg taattggcaa aggtggcgtc aaacatgaaa agatcagaac   3180
caatacccta aaagctgtgg atcgtggtta tgacgtcagc tttgctgagg aatcaggacc   3240
aggcaccaag ttccacaaga atgcaattgg atctgtcaca gatgtttgtg gggagcacaa   3300
aggctattgc atccacatgg gccacggtgt ttacgcatcc gtagctcacg tggtgaaagg   3360
ggattcattt ttcttgggtg aaaggatttt tgatcttaag actaatggtg aattttgctg   3420
ctttcgcagc acgaagattc tacctagtgc tgcacctttc ttttctggga agcccactcg   3480
tgatccgtgg ggatcccccg tggcaactga gtggaagcct aaaatgtaca caacaacctc   3540
tggaaagatt ctggggtgct ttgcaacaac ttcaactgaa actcacccgg gagactgtgg   3600
cctcccatat attgatgaca acgggagggt gaccggcctc cacactggct ctgggggacc   3660
caaaacccca agtgccaagt tggtggtgcc atatgtgcat attgacatga agactaaatc   3720
cgtcactgct caaaagtatg acgtaacaaa gcctgatata agttacaaag gcttaatttg   3780
taagcaattg gatgagatta ggattatacc aaaaggcaca cgtctccatg tctccccagc   3840
ccacactgag gattatcaag aatgctcaca ccaacccgca tcacttggaa gcggggatcc   3900
ccgctgtcca aaatctctca ctgctatagt tgttgattct ctaaaaccat actgtgagaa   3960
ggttgagggt cctccacatg atgttttgca cagagttcaa aagatgctta tcgaccacct   4020
ttcaggcttt gtccctatga acatttcctc ggaaacctct atgctctcag ctttccacaa   4080
actcaatcat gatacttcct gtggaccata cttgggtggc agaaagaaag atcacatggc   4140
taacggtgag ccggacaagc agttattgga tctcctgtct gcaaaatgga aattggccac   4200
ccaaggcata gcactaccac atgagtacac aattgggcta aaggacgagt taaggcccgt   4260
ggagaaggtt agtgaaggga agagaaggat gatttggggt tgtgatgttg gcgtcgctac   4320
tgtctgtgca gctgcgttca agggtgttag cgatgccatc acagcaaacc accagtacgg   4380
gcctatacag gttggtatca acatggatag ccccagcgtc gaagcgctgt tccaaaggat   4440
caaaagcgcg gccaaggtat ttgcggtcga ttattccaaa tgggattcga cccaatcgcc   4500
tcgtgtcagt gcagcttcaa ttgacatcct tcgttacttc tctgatcgct ctccaattgt   4560
tgactcagcc tctaacacac tgaagagccc tcctgttgca atctttaatg gtgttgctgt   4620
aaaagtgtcc tctggcttac catctggaat gcctcttacc tcagtaatca attcccttaa   4680
tcattgtctg tatgttgggt gtgccattct tcaatcccta gaagctaagg ccattcccgt   4740
cacttggaac cttttctcaa cttttgatat catgacttac ggggatgatg gtgtctacat   4800
gtttcctatt atgtatgcaa gtattagtga ccaaattttt ggaaatcttt cgtcctatga   4860
```

-continued

```
cctgaaacca actcgggttg acaagtccgt tggagcaatt gagcctattg atcctgactc   4920
tgttgttttc ttgaagagaa caatcacaag gacacctcag gggataaggg gtttacttga   4980
tcgcagctct ataataagac aattctatta tattaaaggt gagaactccg atgactggaa   5040
gagcccccca aaacatattg acccaacatc tcgagggcaa cagctttgga atgcctgtct   5100
gtacgctagc caacatggct tggagttttt caacaaggtt tacaggctgg ccgagagggc   5160
tgttgaatat gaagagctgc actttgaacc cccaacatat gcttcggctt tggatcatta   5220
caacagccag ttcaatggcg tggaggcgcg gtctgaccag atcgactcga gtggcatgac   5280
cgccctacac tgtgatgtgt tcgaagtttg agcatgtgct caacctgcgc taacgtgctt   5340
aaatactatg attgggatcc ccacttcaaa ttggtgatcg accctaataa atttctttct   5400
gttggattct gtgataaccc gcttatgtgt tgctatcctg agttgcttcc agaattcggc   5460
actgtgtggg attgtgatca atctccactg caaatttacc ttgaatctat tcttggtgat   5520
gatgaatggt cttctaccta tgaagccatt gaccctgtcg ttccaccaat gcactgggac   5580
aaaatgggga aaatcttcca acctcaccct ggtatgctaa tgcaccatat catcggtgaa   5640
gttgccaagg gatgggatcc aaacttgcct ttgttccgat tggaggccga tgatggatcg   5700
gtgacaaccc ctgaacaagg aacaatggtt ggcggagtca ttgctgaacc cagcgcccaa   5760
atgtcaactg ctgctgacat ggcctctggg aaaagtgttg actccgaatg ggaggctttc   5820
ttctcattnc acactagtgt aaattggagt acatctgaaa cacaaggaaa gattctattc   5880
aaacaatcac ttggacccct gctaaaccca tatcttgaac acatatctaa gctttatgtt   5940
gcatggtctg gatctataga ggttaggttt tctatttctg gttctggtgt ttttgggggga   6000
aaactcgctg ctattgttgt gccgcctggg gtagacccag tgcaaagcac atcaatgcta   6060
cagtatcctc atgttctatt tgatgcccgt caggtagaac ctgttatctt ttcaatacct   6120
gatttgagaa acagcttgta ccatcttatg tcagatactg atactacctc ccttgtaatt   6180
atggtgtaca atgatcttat taatccttat gcaaatgatt ctaactcttc tggatgtatt   6240
gtcactgttg agactaaacc tggaatcgat ttcaagtttc accttctgaa accccctgga   6300
tctatgctta cccatggctc tatcccttca gatttaatac caaaatcttc ttctctttgg   6360
atagggaatc gtcactggac tgacataacc gattttgtca ttaggccttt tgtgttccaa   6420
gcaaaccgtc attttgattt taatcaggaa acagctggtt ggagtacgcc aagattccga   6480
ccactagccg taacggttag ccaaagtaaa ggagcaaaat tggggaatgg tattgcgacc   6540
gactacatcg tgcctgggat tcctgatgga tggccagaca ctacaatccc aacaaaactg   6600
acacccacag gcgattatgc aattacatct agtgatggta atgacattga aacaaaactt   6660
gaatacgaaa atgctgatgt gattaaaaac aacacaaact tcaggagcat gtacatttgt   6720
gggtcgctcc aaagagcctg gggtgataag aagatttcta atactggttt cataactact   6780
ggtgttatct ctgataattc cataagccca agcaatacca ttgatcaaag caaaatcgtg   6840
gtctatcaag acaatcatgt caatagtgaa gttcaaacct cagacatcac acttgcaatt   6900
cttggctaca ctggtattgg tgaggaggca attggcgcca atcgggactc ggttgtacgc   6960
ataagtgtgc tgccagaaac aggtgcccgt gggggaaacc atccaatctt ttataagaat   7020
tctatgaagc ttggttacgt gatcagctcc attgatgtgt ttaattccca gatcttgcac   7080
acctctagac aactatcact gaataactac ttactacctc cagattcttt tgctgtctat   7140
cgaattattg attctaatgg gtcttggttt gatataggca ttgattctga tggattttct   7200
tttgttggtg tctcaagttt tcctaagtta gagtttccac tttctgcctc ctatatggga   7260
```

-continued

```
attcagttgg caaagattcg tcttgcctct aatattagga gttctatgac taaattatga   7320

attcaatatt aggcttaatt gacactgtta caaatacaat tggcaaagct caacaaattg   7380

aattagataa agctgcactt ggtcaacaac gcgaactggc tttgcaacga attaaccttg   7440

atcgccaggc gttgaacaac caagttgagc aatttaacaa aattcttgag caaagggtac   7500

aaggccccat ccagtctgtg cggctcgcac gtgctgctgg atttagggtt gacccttact   7560

catacacaaa tcaaaatttt tacgatgacc aattgaatgc aattagacta tcttatagga   7620

atttgtttaa ataattggcc acaagtatcc cttcgggctg ccgcatttgc gcctaacccc   7680

aggg                                                                7684


<210> SEQ ID NO 63
<211> LENGTH: 24
<212> TYPE: DNA
<213> ORGANISM: Feline Calicivirus

<400> SEQUENCE: 63

catcgatcga tgtcgacgga tcca                                            24


<210> SEQ ID NO 64
<211> LENGTH: 25
<212> TYPE: DNA
<213> ORGANISM: Feline Calicivirus

<400> SEQUENCE: 64

gtgcatccgt cgacatcgat cgatg                                           25


<210> SEQ ID NO 65
<211> LENGTH: 45
<212> TYPE: DNA
<213> ORGANISM: Feline Calicivirus

<400> SEQUENCE: 65

tcgaggatcc gccaccatgg ccgatgatgg atcggtgaca acccc                     45


<210> SEQ ID NO 66
<211> LENGTH: 46
<212> TYPE: DNA
<213> ORGANISM: Feline Calicivirus

<400> SEQUENCE: 66

tcgactcgag tcataattta gtcatagaac tcctaatatt agaggc                    46
```

FELINE CALICIVIRUS VACCINE

CROSS-REFERENCE TO RELATED APPLICATIONS

This application is a national stage entry under 35 U.S.C. § 371 of PCT/EP2016/082330 filed on Dec. 22, 2016, which claims priority to EP15202594.6 filed on Dec. 23, 2015, the contents of which are hereby incorporated by reference in their entireties.

The present invention relates to a new feline calicivirus capsid protein, to live attenuated feline calicivirus comprising that capsid protein, to live recombinant carrier viruses and live attenuated hybrid feline calicivirus comprising that capsid protein, to vaccines comprising such live attenuated feline caliciviruses, live recombinant carrier viruses and live attenuated hybrid feline calicivirus, and to methods for the preparation of such viruses.

Feline calicivirus (FCV) is a single-stranded positive-sense RNA virus that belongs to the genus Vesivirus in the family Calicivirus. The virus is highly contagious and causes upper respiratory tract disease (URD) and oral ulceration in felines. The virus is also associated with chronic gingivitis and stomatitis. More recently, a virulent systemic feline calicivirus commonly referred to as VS-FCV emerged that causes high mortality, edematous and ulcerative skin lesions and jaundice. Transmission of FCV is largely by contact with nasal or oral secretions (Scherk, M. A. et al., Journal of Feline Medicine and Surgery (2013) 15, Supplementary File).

The genome and genomic organization of the calicivirus family is well-known in the art. A general overview is i.a. published by Clarke, J. et al. (Inf. Diseases 181 (Suppl. 2): S309-316 (2000)). The first complete genome sequence of a feline calicivirus was published already in 1992 (Carter, M. J. et al., Virology 190: 443-448 (1992)), and in later years the complete genome sequences of many more feline caliciviruses have been published (i.a. by Oka, T. et al., GenomeA, May/June 2013, vol. 1, issue 3, e00349-13, Genomea.asm.org) and are available through i.a. Genbank.

The genome of FCV comprises only three open reading frames; ORF 1, 2 and 3. ORF1 encodes a large non-structural polyprotein. ORF3, a short 3'-terminal ORF, encodes a minor protein that is thought to be involved in encapsidation of genomic RNA.

ORF 2 is the open reading frame that encodes the FCV capsid protein. It is known that the capsid protein is the protein that triggers protective immune response in the host. Thus, the capsid protein is the target protein for the development of vaccines for the protection of felines against FCV infection.

FCV strains comprise only one serotype and predominantly one serogroup worldwide. However, there is a considerable genetic, and thus antigenic, variation between strains. This high level of antigenic variation makes it difficult to obtain a broad protection in felines against FCV: although vaccination with a homologous strain is very efficient, the level of cross-protection of one strain against another strain is quite variable. (Coyne C. P. et al., J. Virol. 86: 11356-11367 (2012)).

At this moment, modified live and inactivated vaccines are available and they are usually administered systemically. Originally, vaccines used to be single vaccines, mostly based on strain FCV F9 or FCV 255. However, they all suffer from the problem identified above: the lack of broad cross-protection.

Currently, this problem is to a certain extent circumvented, at least partially, by administering bivalent vaccines that comprise two different FCV strains such as FCV 431 and FCV G1. Such (inactivated) bivalent vaccines are currently commercially available both in the USA and in Europe. (Poulet H, et al., Vaccine 26: 3647-3654 (2008), Chengjin Huang et al., Journal of Feline Medicine and Surgery February 12: 129-137 (2010)).

An alternative for live attenuated and inactivated vaccines was developed by McCabe V. J. et al. who constructed a live attenuated recombinant carrier virus (LARCV), in this case a myxomavirus, expressing the FCV capsid protein and successfully administered this recombinant myxomavirus as an LARCV vaccine to felines.

Such recombinant myxoma-carrier based vaccines have the advantage that the carrier is attenuated, does not replicate in felines and only carries the FCV ORF that encodes the FCV capsid protein. Therefore, there is no shedding of FCV or the carrier virus into the environment after vaccination.

Another example of a live attenuated recombinant carrier virus expressing the FCV capsid protein is the Feline Herpesvirus carrier as described by Yokoyama, N. et al. (J. Vet. Med. Sci. 60:717-723 (1998)). This carrier was also used in the vaccination of felines against FCV.

However, a live attenuated FCV vaccine or recombinant carrier based vaccine that is both safe and shows a broad level of cross-protection has not been developed yet.

It is an objective of the present invention to provide FCV vaccines that are safe and still show a broad level of cross-protection.

It was surprisingly found that a hitherto unknown FCV stain exists of which the capsid protein shows a remarkably broad spectrum of cross-protection against many FCV field strains. An example of the capsid protein of a representative of this strain is depicted in SEQ ID NO: 34. The representative of this novel FCV strain of which the capsid protein sequence is shown in SEQ ID NO: 34 is further referred to as FCV strain Kalem Crouch.

Table 1 shows the cross-neutralising properties of antiserum raised against the novel FCV strain according to the invention with 31 other FCV strains. The $\log_{10}$ reduction in virus titre is shown. A reduction in titre of >1.5 $\log_{10}$ is considered significant.

As follows from this table, antiserum raised against the novel FCV strain Kalem Crouch surprisingly neutralises 26 out of the 31 FCV strains tested. A comparisson was made to the commonly used F9 strain. As can be seen in table 1, it is seen that antiserum raised against F9 only show a significant reduction of titer for 3 out of 22 FCV strains tested.

The amino acid sequence of the capsid protein of this new FCV strain has been compared with the known amino acid sequence of 24 other FCV capsid proteins and it can be concluded that the sequence differs quite significantly from the known FCV capsid proteins. As can be seen from FIG. 5, the overall sequence identity between the capsid protein of the new strain and that of known FCV strains is around 87%. In addition, several unique amino acids of the new capsid protein are identified K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636. In addition, the sequence KLEYEN of amino acid 447-452, and GVISD of amino acid 489-493 are also unique.

It will be understood that, for the amino acid sequence of SEQ ID NO: 34 and the DNA encoding the protein, minor natural variations may exist between individual representatives of this strain. First of all, at the nucleotide level, there is the so-called "wobble in the second and third base" explaining that nucleotide changes may occur that remain unnoticed in the amino acid sequence they encode: e.g. triplets TTA, TTG, TCA, TCT, TCG and TCC all encode Leucine. In addition, there may be minor variations at the nucleotide level between representatives of FCV that may lead to minor variations in amino acid sequence. These variations can be reflected by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al. in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between identical proteins. Such amino acid substitutions of the exemplary embodiments of this invention, as well as variations having deletions and/or insertions are within the scope of the invention as long as the resulting proteins retain their immune reactivity. This explains why an FCV capsid protein according to the invention, when isolated from different field isolates, may have an identity level of about 90%, while still representing a protein with a comparable immunological cross-reactivity.

Thus, a first embodiment of the present invention relates to a feline calicivirus capsid protein that has a sequence identity of at least 90% with the amino acid sequence as given in SEQ ID NO: 34.

Optionally the capsid protein has a sequence identity of at least 91%, 92%, 93%, 94%, 95%, 96%, 97%, 98%, 99% or 100% with the amino acid sequence as given in SEQ ID NO: 34 in increasing order of preference.

Another embodiment of the present invention and/or embodiments thereof relates to a live attenuated FCV comprising a capsid protein that has a sequence identity of at least 90% with the amino acid sequence as given in SEQ ID NO: 34.

Another embodiment of the present invention and/or embodiments thereof relates to a live attenuated FCV comprising a capsid protein according to the present invention and/or any embodiment thereof.

Optionally the FCV has a capsid protein has a sequence identity of at least 91%, 92%, 93%, 94%, 95%, 96%, 97%, 98%, 99% or 100% with the amino acid sequence as given in SEQ ID NO: 34 in increasing order of preference.

In addition, the present invention relates to a feline calicivirus capsid protein that comprises at least one of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636. Suitably the feline calicivirus capsid protein according to the invention and/or embodiments there of comprises at least one or more of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636. Suitably the feline calicivirus capsid protein according to the invention and/or embodiments there of comprises at least one, two, three, four, five or more of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636.

In addition, the present invention relates to a feline calicivirus capsid protein that comprises at least one of the following amino acids I317, L390, A391, V392, Q396, S397, K398, N404, T426, T431, S438, S437, D440, E445, K447, L448, E451, N452, G484, G489, I491, N516, S517, E518, I524, or S545. Suitably the feline calicivirus capsid protein according to the invention and/or embodiments there of comprises at least one or more of the following amino acids I317, L390, A391, V392, Q396, S397, K398, N404, T426, T431, S438, S437, D440, E445, K447, L448, E451, N452, G484, G489, I491, N516, S517, E518, I524, or S545. Suitably the feline calicivirus capsid protein according to the invention and/or embodiments there of comprises at least one, two, three, four, five or more of the following amino acids I317, L390, A391, V392, Q396, S397, K398, N404, T426, T431, S438, S437, D440, E445, K447, L448, E451, N452, G484, G489, I491, N516, S517, E518, I524, or S545.

In addition, the present invention relates to a feline calicivirus capsid protein that comprises at least one of the following amino acids L390, A391, V392, Q396, S397, K398, N404, T426, T431, S438, S437, D440, E445, K447, L448, E451, N452, G484, G489, I491, N516, S517, E518, or I524. Suitably the feline calicivirus capsid protein according to the invention and/or embodiments there of comprises at least one or more of the following amino acids L390, A391, V392, Q396, S397, K398, N404, T426, T431, S438, S437, D440, E445, K447, L448, E451, N452, G484, G489, I491, N516, S517, E518, or I524. Suitably the feline calicivirus capsid protein according to the invention and/or embodiments there of comprises at least one, two, three, four, five or more of the following amino acids L390, A391, V392, Q396, S397, K398, N404, T426, T431, S438, S437, D440, E445, K447, L448, E451, N452, G484, G489, I491, N516, S517, E518, or I524.

Suitably the feline calicivirus capsid protein according to the invention and/or embodiments there of comprises the following amino acids K89, M90, and M100.

Suitably the feline calicivirus capsid protein according to the invention and/or embodiments there of comprises the following amino acid I317.

Suitably the feline calicivirus capsid protein according to the invention and/or embodiments there of comprises the following amino acids L390, A391, V392, Q396, S397, K398, and N404.

Suitably the feline calicivirus capsid protein according to the invention and/or embodiments there of comprises the following amino acids T426, T431, S438, S437, D440, E445, K447, L448, E451, and N452.

Suitably the feline calicivirus capsid protein according to the invention and/or embodiments there of comprises the following amino acids G484, G489, and I491.

Suitably the feline calicivirus capsid protein according to the invention and/or embodiments there of comprises the following amino acids N516, S517, E518, and I524.

Suitably the feline calicivirus capsid protein according to the invention and/or embodiments there of comprises the following amino acids S545.

Suitably the feline calicivirus capsid protein according to the invention and/or embodiments there of comprises the following amino acids S634, F635, and P636.

It is expressly envisioned for the feline calicivirus capsid protein according to the invention and/or embodiments thereof to comprise combinations of the above indicated groups of amino acids. For example the feline calicivirus capsid protein according to the invention and/or embodiments there of comprises the following amino acids L390, A391, V392, Q396, S397, K398, N404 and I317. Another example relates to a feline calicivirus capsid protein according to the invention and/or embodiments there of that comprises the following amino acids N516, S517, E518, I524 and S545.

In addition, the present invention relates to a feline calicivirus capsid protein wherein amino acids 447-452 are KLEYEN and/or wherein amino acid 489-493 are GVISD. Suitably the present invention relates to a feline calicivirus capsid protein wherein amino acids 447-452 are KLEYEN and amino acid 489-493 are GVISD. Suitably a feline calicivirus capsid protein wherein amino acids 447-452 are KLEYEN and/or wherein amino acid 489-493 are GVISD also comprises at least one of the following amino acids K89, M90, M100, I317, L390, A391, V392, Q396, S397, K398, N404, T426, T431, S438, S437, D440, E445, G484, N516, S517, E518, I524, S545, S634, F635, or P636.

Another embodiment of the present invention and/or embodiments thereof relates to a live attenuated FCV comprising a capsid protein that has a sequence identity of at least 90% with the amino acid sequence as given in SEQ ID NO: 34 and at least one of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636.

A capsid protein or the region encoding the capsid protein according to the invention such as ORF2 or a fragment thereof may be used in several ways in the preparation of vaccines for the protection of felines against FCV.

A DNA fragment comprising the region encoding a capsid protein according to the invention and/or embodiments thereof may e.g. be used for the preparation of non-FCV recombinant carrier viruses comprising the capsid protein according to the invention and/or embodiments thereof. It may also be used for the preparation of hybrid FCV, as described below.

Thus, a third embodiment of the present invention relates to a DNA fragment characterized in that it comprises a region encoding a capsid protein according to the invention and/or embodiments thereof.

In cases where a recombinant carrier is used as a carrier for a DNA fragment comprising the region encoding a capsid protein according to the invention and/or embodiments thereof, the expression of the capsid protein would usually be obtained by placing the DNA fragment comprising the region encoding a capsid protein according to the invention and/or embodiments thereof under the control of a suitable heterologous promoter.

A suitable promoter is a promoter that is capable of driving the transcription of a coding region that is located downstream of the promoter in the host cell; in this case a eukaryotic, more specific a feline cell. A large number of suitable promoters for the expression of the FCV capsid protein are known in the art, which are recognized for their efficient level of expression. Such promoters include classic promoters such as the (human) cytomegalovirus immediate early promoter (Sun-Young Lee et al., Journal of Biomedical Science 6: 8-17 (1999), Seed, B. et al., Nature 329, 840-842, 1987; Fynan, E. F. et al., PNAS 90, 11478-11482, 1993; Ulmer, J. B. et al., Science 259, 1745-1748, 1993), the Human Cytomegalovirus enhancer-promoter (Donofrio G., et al., Clinical and Vaccine Immunology 13: 1246-1254, (2006)), the Mouse Cytomegalovirus immediate early (MCMViel) promoter, the Mouse Cytomegalovirus early (MCMVel) promoter, SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2, the β-actin promoter (Tang et al., Nature 356, 152-154, 1992) and the CAG promoter. (Miyazaki, J; Takaki, S; Araki, K; Tashiro, F; Tominaga, A; Takatsu, K; Yamamura, K., Gene 79 (2): 269-277 (1989), and Niwa, H; Yamamura, K; Miyazaki, J., Gene 108 (2): 193-199 (1991)).

Suitably the region encoding the capsid protein is placed under the control of a suitable promoter.

The DNA fragment comprising a region encoding a capsid protein according to the invention and/or embodiments thereof may e.g. be a plasmid. This plasmid may be in a circular or linear form.

Given the broad protection provided by the capsid protein according to the invention and/or embodiments thereof, it is attractive to use the region encoding the capsid protein according to the invention and/or embodiments thereof in a live recombinant carrier virus.

Such live attenuated recombinant carrier viruses (LARCVs) are recombinant viruses capable of infecting a host animal, in this case a feline species, and carrying a foreign gene, in this case the region encoding the capsid protein according to the invention and/or embodiments thereof, under the control of a suitable promoter.

LARCVs and their uses have been reviewed i.a. by Souza, A. P. D. et al., in Braz. J. Med. Biol. Res, 38: 509-522 (2005). Examples of such live recombinant carrier viruses are: poxviruses (i.a. vaccinia virus), adenoviruses, herpesviruses, myxomaviruses and more recently alphaviruses.

Thus, a fourth embodiment of the present invention relates to live attenuated recombinant carrier viruses (LARCV) comprising the region encoding the capsid protein according to the invention, under the control of a promoter.

An example of such an attenuated live recombinant carrier virus is provided by McCabe et al who describe the use of myxomavirus as LARCV for the capsid protein of FCV strain F9 (vide supra).

Another example of a live attenuated recombinant carrier virus expressing the FCV capsid protein is the Feline Herpesvirus carrier expressing the FCV capsid protein such as described by Yokoyama, N. et al., (vide supra).

Suitably the live attenuated recombinant carrier virus is a myxomavirus or a Feline Herpesvirus.

Another embodiment of the present invention and/or embodiments thereof relates to a live attenuated recombinant carrier virus according to the invention and/or embodiments thereof, for use in the protection of felines against infection with FCV.

The capsid protein and its coding region may also allow another approach for the protection of felines against FCV. This approach relates to a hybrid FCV.

It is known in the art that live attenuated vaccines exist for the protection of felines against FCV infection. An example of such a live attenuated FCV is FCV strain F9, known to provide a safe live vaccine when administered systemically. However, as mentioned above, FCV strains in general and also the F9 strain do not provide broad cross-protection against infection of felines with other FCV strains.

It was now surprisingly found, that hybrid FCV strains that comprise a region encoding a capsid protein according to the invention and/or embodiments thereof and an ORF1 from an attenuated FCV provide both a high level of safety and a broad cross-protection.

Another embodiment relates to a live attenuated hybrid FCV, characterised in that said FCV comprises a region encoding a capsid protein according to the invention and/or embodiments thereof and comprises a region encoding an attenuation from open reading frame 1 (ORF1) from an attenuated FCV.

Suitably the live attenuated hybrid FCV of the present invention and/or embodiments thereof comprises an open reading frame 2 (ORF2) encoding a capsid protein according to the invention and/or embodiments thereof and comprises an open reading frame 1 (ORF1) from an attenuated FCV.

Methods for the construction of hybrid caliciviruses are well-known in the art. For feline calicivirus, Neill et al. described capsid protein domain exchanges between distinct FCV strains (Neill, D. J. et al., J. Virol 74:1079-1084 (2000)). Further methods for the recovery of recombinant viruses from cells after transfection of cRNA or cDNA constructs were already described in 2002 by Thumfart J. O. and Meyers G. (J. Virol. 76: 6398-6407 (2002)). Aubry, F. et al., have recently described even faster methods to generate single-stranded positive-sense RNA viruses using subgenomic amplicons (J. Gen. Virol 95:2462-2467 (2014)).

Attenuated viruses may e.g. be obtained by growing the viruses according to the invention and/or embodiments thereof in the presence of a mutagenic agent, followed by selection of virus that shows a decrease in progeny level and/or in replication speed. Many such agents are known in the art.

Another frequently used method for attenuation is serial in vitro passage. During this process, viruses get adapted to the cell line used for the serial passage. As a consequence, they behave attenuated when subsequently administered to the natural host again as a vaccine.

Still another way of obtaining attenuated viruses is to subject them to growth under temperatures deviating from the temperature of their natural habitat. Selection methods for temperature sensitive mutants (Ts-mutants) are well-known in the art. Such methods comprise growing viruses in the presence of a mutagen followed by growth at a sub-optimal temperature and at the optimal temperature, titration of progeny virus on cell layers and visual selection of those plaques that grow slower at the optimal temperature. Such small plaques comprise slow-growing and thus desired live attenuated viruses.

A more direct and predictable method for the generation of attenuated single-stranded positive-sense RNA viruses is e.g. described by Weeks, S. A. et al., in the J. of Biol. Chem., 287: 31618-31622 (2014).

Optionally, the skilled person would use a region encoding an attenuation from open reading frame 1 (ORF1) or the ORF1 from already available attenuated FCV strains. A well-known example of such a live attenuated virus is FCV strain F9.

Kalunda et al. AJVR (1975) 36:353-356 described the properties of the strain FCV-F9 as a vaccine. See also Bittle, et al., Ibid. (1976) 37:275-278.

Suitably the invention and/or embodiments thereof relate to a live attenuated hybrid FCV according to the invention that comprises a region encoding an attenuation from open reading frame 1 (ORF1) or an open reading frame 1 (ORF1) that is obtained from FCV strain F9.

In the Example-section, a method for the preparation of a hybrid FCV according to the invention and/or embodiments thereof as described above is described in detail.

Again another embodiment of the present invention relates to live attenuated hybrid FCV according to the invention and/or embodiments thereof, for use in the protection of felines against infection with FCV.

Mammalian cells, suitable for the cultivation of live recombinant carrier viruses are known in the art. Such cells are the cells that support the growth of the known LARCVs, such as poxviruses, adenoviruses, herpesviruses, myxomaviruses and more recently alphaviruses.

Attenuated recombinant myxoma-based carrier virus expressing the FCV capsid protein may e.g. be grown on RK13 cells. Attenuated recombinant Feline Herpesvirus-based carrier virus expressing the FCV capsid may e.g. be grown on Crandell-Rees feline kidney (CRFK) cells.

Equally, cells suitable for the cultivation of live attenuated FCV and live attenuated hybrid FCV are known in the art. The most common cells for growing FCV are CRFK cells.

Thus, again another embodiment of the present invention relates to a cell culture comprising a live attenuated FCV according to the invention and/or embodiments thereof, a LRCV according to the invention or a live attenuated hybrid FCV according to the invention.

As indicated above, the FCV capsid protein according to the invention and/or embodiments thereof provides a broad level of cross-protection against a variety of different FCV strains.

For this reason, live attenuated FCVs according to the invention and/or embodiments thereof, live recombinant carrier viruses according to the invention and/or embodiments thereof and live attenuated hybrid FCVs according to the invention and/or embodiments thereof provide a very suitable basis for vaccines for the protection of felines against FCV.

Thus, still another embodiment of the present invention relates to vaccines for the protection of felines against FCV, wherein such vaccines comprises a live attenuated FCV according to the invention and/or embodiments thereof and a pharmaceutically acceptable carrier, and/or a live attenuated recombinant carrier virus according to the invention and/or embodiments thereof and a pharmaceutically acceptable carrier and/or a live attenuated hybrid FCV according to the invention and/or embodiments thereof and a pharmaceutically acceptable carrier.

Protection in this respect should be interpreted in a broad sense: protection of felines against FCV is considered to comprise vaccination in order to prevent the disease, vaccination to diminish the signs of the disease and therapeutic vaccination after the disease is diagnosed.

Examples of pharmaceutically acceptable carriers that are suitable for use in a vaccine for use according to the invention are sterile water, saline, aqueous buffers such as PBS and the like. In addition a vaccine according to the invention may comprise other additives such as stabilizers and/or anti-oxidants.

As mentioned above, the virulence of FCV isolated from the field is relatively high: feline calicivirus infection is a cause of upper respiratory tract infection and when a virulent FCV is administered oropharyngeal it causes pyrexia, oculonasal discharge, gingivo-stomatitis, glossitis, weight loss and poor body condition. The virulent systemic form of FCV causes pyrexia, vasculitis, oedema, ulcerative lesions on limbs, jaundice and death. (There is sporadic information that even the vaccine strain of FCV F9 when administered oropharyngeally does cause gingivo-stomatitis).

A live attenuated virus as defined herein is a virus that has a decreased level of virulence when compared to virus isolated from the field. Vaccination with a live attenuated virus, a live attenuated hybrid virus or LRCV according to the invention and/or embodiments thereof at least reduces the severity of infection (reduction in the clinical signs and symptoms) in terms of duration of pyrexia, oral ulcers, weight loss and/or days virus excreted, when compared to infection of non-vaccinated animals with a wild-type FCV.

Usually, live attenuated FCV, LRCV and live attenuated hybrid FCV based vaccines may be used without the addition of adjuvants. Nevertheless, if so required, an adjuvant may be included in the vaccine.

An adjuvant is an immune stimulatory substance boosting the immune response of the host in a non-specific manner. The adjuvant may be a hydrophilic adjuvant, e.g. aluminum hydroxide or aluminum phosphate, or a hydrophobic adjuvant, e.g. a mineral oil based adjuvant.

Live attenuated FCV, LRCV and live attenuated hybrid FCV based vaccines according to the invention and/or embodiments thereof may comprise a stabilizer. A stabilizer may be added to a vaccine according to the invention and/or embodiments thereof e.g. to protect it from degradation, to enhance the shelf-life, or to improve freeze-drying efficiency. Useful stabilizers are i.a. SPGA (Bovarnik et al., 1950, J. Bacteriology, vol. 59, p. 509), skimmed milk, gelatin, bovine serum albumin, carbohydrates e.g. sorbitol, mannitol, trehalose, starch, sucrose, dextran or glucose, lactoses, proteins such as albumin or casein or degradation products thereof, and buffers, such as alkali metal phosphates. To reconstitute a freeze-dried composition, it is suspended in a physiologically acceptable diluent. Such a diluent may e.g. be as simple as sterile water, or a physiological salt solution. In a more complex form the freeze-dried vaccine may be suspended in an emulsion e.g. as described in EP 1,140,152.

The dosing scheme for the application of a vaccine according to the invention and/or embodiments thereof to the target organism may be the application of single or multiple doses and in such an amount as will be immunologically effective.

What constitutes an "immunogenically effective amount" for a vaccine according to the invention that is based upon a virus according to the invention and/or embodiments thereof is dependent on the desired effect. The term "immunogenically effective amount" as used herein relates to the amount of live attenuated FCV, live attenuated carrier virus or live attenuated hybrid FCV according to the invention that is necessary to induce an immune response in felines to the extent that it decreases the pathological effects caused by infection with a wild-type FCV virus, when compared to the pathological effects caused by infection with a wild-type FCV in non-immunized felines.

It is well within the capacity of the skilled person to determine whether a treatment is "immunologically effective", for instance by administering an experimental challenge infection to vaccinated animals and next determining a target animal's clinical signs of disease, serological parameters or by measuring re-isolation of the pathogen, followed by comparison of these findings with those observed after challenge of non-vaccinated felines.

The amount of virus administered will depend on the route of administration, possibly the presence of an adjuvant and the moment of administration.

A preferred amount of a live vaccine comprising a live attenuated FCV or live attenuated hybrid virus according to the invention and/or embodiments thereof is expressed for instance as Tissue Culture Infectious Dose ($TCID_{50}$). For instance for such a live attenuated virus a dose range between $10^2$ and $10^8$ $TCID_{50}$ per animal dose may advantageously be used; preferably a range between $10^4$ and $10^6$ $TCID_{50}$ is used.

A preferred amount of a live recombinant carrier virus based upon myxomavirus in a vaccine would be in the range of $10^4$-$10^8$ plaque-forming units (PFU).

A preferred amount of a live recombinant carrier virus based upon Feline Herpesvirus in a vaccine would also be in the range of $10^4$-$10^8$ plaque-forming units (PFU).

Several ways of administration may be applied, all known in the art. Vaccines according to the invention are preferably administered to felines via injection, preferably intramuscular injection. The protocol for the administration can be optimized in accordance with standard FCV or live recombinant carrier virus vaccination practice.

Domesticated felines are usually vaccinated against several diseases. For reasons of ease of administration, and also for economic reasons, it is desirable to administer several vaccines at the same time, preferably as a combination vaccine. Such combination vaccines would then comprise a live attenuated FCV according to the invention and/or embodiments thereof and/or a live attenuated hybrid FCV according to the invention and/or embodiments thereof and/or a live recombinant carrier virus according to the invention and/or embodiments thereof, and in addition to this at least one other feline-pathogenic microorganism or feline-pathogenic virus and/or at least one other immunogenic component and/or genetic material encoding said other immunogenic component of said feline-pathogenic microorganism or feline-pathogenic virus.

Thus a preferred form of this embodiment relates to vaccines for the protection of felines against FCV, wherein such vaccines comprise a live attenuated FCV according to the invention and a pharmaceutically acceptable carrier, and/or a live Recombinant Carrier Virus according to the invention and a pharmaceutically acceptable carrier and/or a live attenuated hybrid FCV according to the invention and a pharmaceutically acceptable carrier, and at least one other feline-pathogenic microorganism or feline-pathogenic virus and/or at least one other immunogenic component and/or genetic material encoding said other immunogenic component of said feline-pathogenic microorganism or feline-pathogenic virus.

In a more preferred form of this embodiment, the at least one other feline-pathogenic microorganism or cat-pathogenic virus is selected from the group consisting of feline panleucopenia virus, *Chlamydia psittaci, Bordetella bronchiseptica*, feline parvovirus, rabies virus and feline herpes virus.

In the Examples section, a detailed example is provided of the construction of a live attenuated hybrid FCV according to the invention. Basically, the method comprises the step of assembling a first and a second amplicon, each comprising a part of the full length viral genome, preferably using overlap extension, resulting in an amplicon that comprises the full length viral genome. Suitably, the first FCV amplicon comprises the full ORF1 region and an adjacent 5'-part of the ORF2 region of an attenuated FCV and the second FCV amplicon comprises a 3'-part of the ORF1 region and the full adjacent ORF2//ORF3 region wherein the ORF2 is an ORF2 encoding an FCV capsid protein according to the invention and/or embodiments thereof.

There thus exists an overlapping region spanning a 5'-part of the ORF1 region and a 3'-part of the ORF2 region that is present in both amplicons. This would allow for assembly of the first and second amplicon through overlap extension.

Therefore, still another embodiment relates to methods for obtaining a live attenuated hybrid FCV according to the invention that comprise the steps of:

a. Preparation of a first FCV amplicon comprising the full ORF1 region and an adjacent 5'-part of the ORF2 region of an attenuated FCV,
b. Preparation of a second FCV amplicon comprising a 3'-part of the ORF1 region and the full adjacent ORF2//ORF3 region wherein the ORF2 is an ORF2 according to the invention,
c. Assembly of the first and second amplicon using overlap extension,
d. Generation of infectious FCV,
e. Infection of susceptible cells with the infectious FCV,
f. Recovery of infectious progeny FCV

LEGEND TO THE FIGURES

Figure 2:
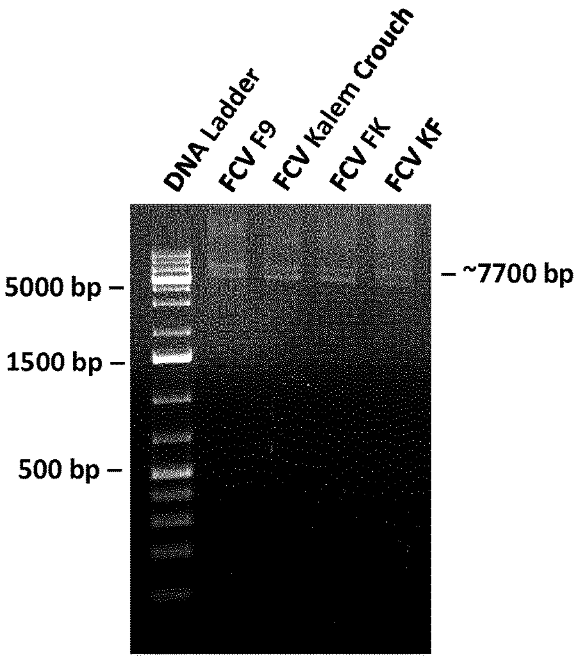

FIG. 1: amplicons covering 5349 bp from the 5' end of the FCV genome, or 2422 and 2416 bp from the 3' end of the FCV F9 and Kalem Crouch genomes respectively were amplified with PCR from FCV cDNA FIG. 2: full-length overlap extension assemblies of FCV F9 (SEQ ID NO: 60), Kalem Crouch (SEQ ID NO: 59), FK (SEQ ID NO: 62) and KF (SEQ ID NO: 61) were generated and resolved on a 1% agarose gel. FCV F9 and Kalem Crouch were made from their respective 5' and 3' amplicons as controls to demonstrate correct design of overlap FIG. 3: full-length recombinant FK and KF FCV DNA was amplified with PCR and resolved on a 1% agarose gel.

Figure 4:
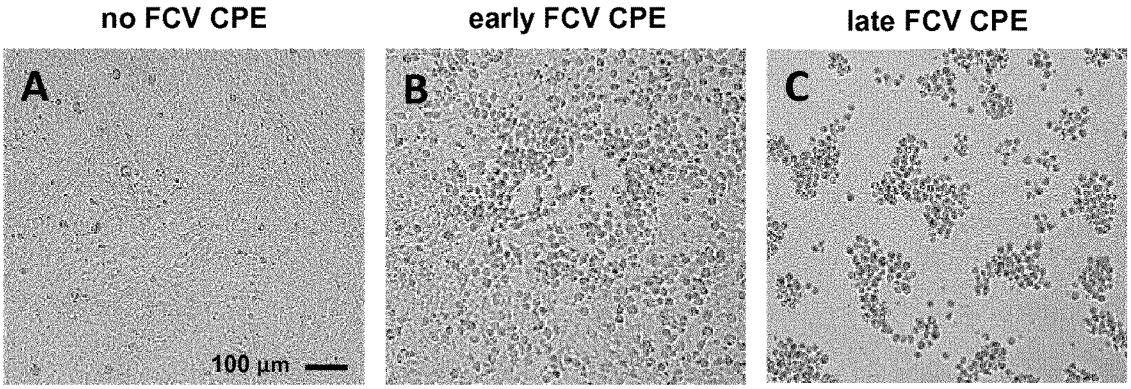

FIG. 4: an example of the typical CPE (cytopathic effect) of FCV in CrFK cells infected with FCV Kalem Crouch.

FIG. 5-1 to FIG. 5-11: Alignment of FCV Kalem Crouch (SEQ ID NO: 34) and F9 (SEQ ID NO: 35) capsid protein sequence to published FCV sequences (SEQ ID NO: 36-58). Numbering of the amino acids is on nucleotide level.

FIG. 6-1 to FIG. 6-22: Sequence alignment of the FCV F9 (SEQ ID NO: 59) and Kalem Crouch strains (SEQ ID NO: 60) to recombinant FCV FK (SEQ ID NO: 61) and KF strains. (SEQ ID NO: 62).

FIG. 7-1 to FIG. 7-11: Alignment of FCV Kalem Crouch (SEQ ID NO: 34) and F9 (SEQ ID NO: 35) capsid protein sequence to published FCV sequences (SEQ ID NO: 36-58). Numbering of the amino acids is on amino acid level.

FIG. 8: Map of the p22m-GFP plasmid with the mutation in the NcoI site of the MCS indicated.

FIG. 9: Comparison of the p22m-GFP and p22m-4a constructs derived from p22-GFP plasmid.

FIG. 10: A diagram of the whole MR24-Kalem Crouch clone genome with a highlighted pMCPK insert.

EXAMPLES

Example 1

Hyper-immune sera raised in cats to strains FCV F9 and Kalem Crouch were used to determine the neutralisation index of the several FCV strains. The experiment is performed as described in section 8 below. The data is shown in table 1. It becomes clear from the table that serum raised against Kalem Crouch has a broad cross protection against many other FCV strains. For serum against Kalem Crouch a significant $Log_{10}$ reduction (i.e. >1.5) is seen against 16 out of 31 FCV strains. Table 1 also shows that the cross-protection of the normally used F9 strain is much less. Serum raised against F9 shows a significant $Log_{10}$ reduction (i.e. >1.5) for 3 out of 22 FCV strains. It should be noted that the 2 FCV strains that are neutralized or at least significantly reduced by the F9 serum, 3809, 6420, CV-21, are F9-like viruses. Thus not only provides Kalem Crouch cross-protection for many more FCV strains than F9 does, it also provides cross-protection for non-F9 strains.

TABLE 1

$Log_{10}$ Reduction by sera

| FCV strain | $Log_{10}$ reduction in titre by FCV Kalem Crouch antisera | $Log_{10}$ reduction in titre by F9 Sera |
|---|---|---|
| 6410 | 3.0 | 0.33 |
| 0708 | 1.51 | 1.45 |
| 3808 | 1.0 | 1.34 |
| 5611 | 1.67 | 1.0 |
| 2218 | 0.49 | 1.2 |
| 5006 | >4.0 | 0.79 |
| 1307 | 1.51 | 0.69 |
| 3809* | 1.82 | 3.15 |
| 1803 | 4.0 | 1.46 |
| 6721 | 3.2 | 0.67 |
| 6420* | 2.0 | Neutralised |
| 4009 | 3.38 | 1.25 |
| 93629-11 | 1.51 | 0.8 |
| 142433-11 | 0.33 | 0.33 |
| 141478-11 | 0.0 | 0.0 |
| 155391-12 | 1.8 | 0.84 |
| 90392-12 | 1.15 | 1.04 |
| CV-21* | 2.66 | 3.2 |
| MD-3 | 2.55 | Not done |
| CV-13 | 2.85 | Not done |
| CV-17 | >4.0 | Not done |
| Tina | 3.0 | Not done |
| Kalem | 3.18 | 1.2 |
| S.W. | >4.0 | 0.8 |
| A.R. | 2.79 | 0.25 |
| R.V. | 3.08 | 0.58 |
| 1703 | 1.54 | Not done |
| 2305 | 3.2 | Not done |
| 3909 | 2.0 | Not done |
| 4505 | 2.66 | Not done |
| 4819 | 2.85 | Not done |
| 5903 | 4.17 | Not done |

Example 2

Construction of Hybrid FCV-Clones

1. Cell Culture

All cell lines were maintained in tissue culture flasks at 37° C., 5% $CO_2$.

Crandell-Rees Feline kidney (CrFK) cells were grown in medium M6B8 supplemented with 5% Foetal Bovine Serum, 0.15% Sodium bicarbonate, 2 mM L-Glutamine, 100 U/ml of Penicillin, 10 μg/ml of Streptomycin and 2 μg/ml of Fungizone.

BsRT7 cells were maintained in medium DMEM supplemented with 5% Foetal Bovine Serum, 2 mM L-Glutamine, 1 mM Sodium Pyruvate and 1 mg/ml Geneticin (G418). Geneticin was removed at cell seeding prior to transfection.

2. Virus Isolation

Oro-pharyngeal/nasal swabs were collected from cats and transported in medium M6B8. The swabs were vortexed briefly and the virus suspension inoculated onto confluent CrFK cells and incubated at 37° C. with 5% $CO_2$ until CPE specific to FCV was observed. Infected flasks were freeze thawed to lyse cells, clarified to remove cellular debris and stored as aliquots at −70° C.

3. Growth of FCV

An appropriate dilution of virus was adsorbed to infect a confluent CrFK monolayer. Cells were incubated at 37° C., 5% $CO_2$ until CPE specific to FCV was observed. Infected flasks were freeze thawed to lyse cells, clarified to remove cellular debris and stored as aliquots at −70° C.

4. RNA Isolation

Clarified viral suspension was centrifuged at 131500×g, 4° C. using a SW28 rotor for approximately 16 hours. RNA was extracted from the resulting pellet using an RNeasy® Miniprep Kit (Qiagen, Hilden, Germany). RNA was eluted in 50 μl RNase free water, aliquoted and stored at −70° C. until use.

5. cDNA Synthesis

FCV RNA was used as a template for cDNA synthesis. cDNA was synthesised using an INVITROGEN Superscript II® kit (Carlsbad, Calif.) and primers Fr2F (SEQ ID NO: 32) and Fr4R (SEQ ID NO: 33).

6. Virus Titration

Serial tenfold dilution of the virus (100 μl/well, 5 wells per dilution) in growth medium was used to infect a confluent monolayer of CrFK cells in 96 well plates. Infected CrFK cells were incubated at 37° C., 5% $CO_2$ for up to 5 days and examined for CPE specific for FCV. The number of wells in which CPE was present was recorded and titres were calculated using Reed Muench method. Titres were expressed as $TCID_{50}$/ml.

7. Preparation of FCV Antibodies

Antibodies to FCV strains were raised in cats. Each treatment group consisted of 3 cats housed separately. Cats were either infected by the oro-pharyngeal route or by subcutaneous injections. Cats were hyperimmunized with a second dose of the virus by the oro-phryngeal route. Plasma was collected from cats three weeks post second inoculation.

8. Virus Neutralisation Assay

Serial dilution of the viruses were mixed with an equal volume of a constant amount of plasma dilution or growth medium and incubated for 1 hour at 37° C. The virus or virus serum mixture was inoculated on confluent CrFK cells (5 wells per dilution) in a 96 well plate. Plates were incubated at 37° C., 5% $CO_2$ for 5 days. The neutralisation index was determined by calculating the difference in the titer observed.

9. Design of Primers to Generate Overlapping DNA Amplicons from FCV cDNA

The PCR reactions to generate an amplicon covering 5349 bp from the 5' of the FCV genome were performed using the Phusion polymerase (NEB, Ipswich, Mass.) with oligonucleotide primer pair FKP1F (SEQ ID NO: 5) and FKP1R (SEQ ID NO: 6), and the PCR conditions described in Table 4. Similarly, PCR reactions to generate an amplicon covering the 2422 bp from the 3' end of FCV F9 and 2416 bp from the 3' end of FCV Kalem Crouch were also performed using the Phusion polymerase (NEB, Ipswich, Mass.) with oligonucleotide primer pair FKP2F (SEQ ID NO: 7) and FKP2R (SEQ ID NO: 8) using the Phusion polymerase (NEB, Ipswich, Mass.), and the PCR conditions described in Table 5.

10. Purification of DNA from PCR Reactions

All amplified DNA was purified using QIAquick® PCR Purification Kit (Qiagen, Hilden, Germany) using two column washes. The concentration and purity of eluted DNA was determined using a Nanodrop instrument (Thermo Scientific, Waltham, Mass.).

11. Combining of FCV Amplicons to Generate Full Length FCV

An equimolar mix was made with 0.1, 0.25, or 0.5 pmol of each FCV amplicons generated as described in methods section 9, and purified as described in methods section 10. A sufficient amount of such a mix, typically 5 μL, was used as template for the overlap extension PCR described in Table 6, using the Phusion polymerase (NEB, Ipswich, Mass.).

12. Generation of Full Length Infectious FCV DNA

A sufficient amount of cDNA reaction, prepared as described in section 5 above, or overlap extension PCR reaction, prepared as described in section 11, typically between 1 and 5 μL, was used as template to generate full length infectious FCV DNA. Th Phusion polymerase (NEB, Ipswich, Mass.) was used together with oligonucleotide primer pairs MBL 446 (SEQ ID NO: 1) and MBL 447 (SEQ ID NO: 2) or FCVT7f (SEQ ID NO: 3) and FCVpAr (SEQ ID NO: 4), and the PCR conditions described in Tables 7 and 8 respectively.

13. Transfection of Full Length Infectious FCV DNA into BsRT7 Cells

BsRT7 cells, cultured as described in section 1 to approximately 50-70% confluence in 24 well plates, were transfected with full length infectious FCV DNA generated as described in section 12 using the INVITROGEN® Lipofectamine® 3000. Typically 3 μg of DNA was used per well. Cells were incubated with the DNA-lipofectamine complex for up to 72 hours.

14. Infection of CrFK Cells with Lysate from Transfected BsRT7 Cells

Transfected BsRT7 cells were lysed by freeze-thawing. The cell-lysate was used to infect a confluent monolayer of CrFK cells.

15. Immunofluorescence Staining of FCV

CrFK cells infected with FCV were fixed with methanol and washed with PBS. Fixed cells were incubated sequentially with a polyclonal anti FCV serum and anti-Cat FITC antibody conjugate or a mouse monoclonal antibody NCL-1G9 (Leica Microsystems, UK) and anti-mouse FITC antibody conjugate. Fluorescence was observed using a DM1L microscope (Leica Microsystems, UK) with the I3 filter.

16. Sequence Analysis of FCV

Full length FCV DNA was made from cDNA using the oligonucleotide primers MBL 446 (SEQ ID NO: 1) and MBL 447 (SEQ ID NO: 2) together with the Phusion polymerase (NEB, Ipswich, Mass.) and PCR conditions described in Table 4. The resulting full length FCV DNA was purified as described in methods section 11 and sequenced using any combination of oligonucleotide primers from Table 3. DNA samples were sequenced by GATC-biotech, UK. 30-100 ng/μl of plasmid or 10-50 ng/μl of PCR product were sent with 10 pmol/μl of sequencing primer.

TABLE 1

PCR primers to generate full length infectious FCV DNA.

| Name | Legacy | Sequence 5' to 3' |
|---|---|---|
| SEQ ID 1 | MBL 446 | CATGGTACCTAATACGACTCACTATAGGGTAAAAGAAATTTGAGACAATG |
| SEQ ID 2 | MBL 447 | TCGACCACCGGTGATTAATTTTTTTTTTTTTTTTTTTTTTTTCCCTGGG |
| SEQ ID 3 | FCVT7f | TACCTAATACGACTCACTATAGGGTAAAAGAAATTTGAGACAATGTCTCAAACTCTGAGCTTCGTGC |
| SEQ ID 4 | FCVT7r | TTTTTTTTTTTTTTTTTTTTTTTTTCCCTGGGGTTAGGCGCAGGTGCGG |

TABLE 2

PCR primers used to generate FCV amplicons.

| Name | Legacy | Sequence |
|---|---|---|
| SEQ ID 5 | FKP1F | GTAAAAGAAATTTGAGACAATGTCTCAAACTCTGAGCTTCGTGC |
| SEQ ID 6 | FKP1R | ATAGTATTTAAGCACGTTAGCGCAGGTTGAGCACATGCTCAAACTTCGAACAC |
| SEQ ID 7 | FKP2F | GAGTGGCATGACCGCCCTACACTGTGATGTGTTCGAAGTTTGAGCATGTGCT |
| SEQ ID 8 | FKP2R | TTTTTTTTTTTTCCCTGGGGTTAGGCGCAGGTGCGG |

TABLE 3

PCR primers for sequencing the full length of the recombinant FCV genome.

| Name | Legacy | Sequence |
|---|---|---|
| SEQ ID 9 | Seg2F | CTTGGTACCGAGCTGTAAAAGAAATTTGAGACAATG |
| SEQ ID 10 | SCJ1R | TGAGCTGTTCTTTGCACA |
| SEQ ID 11 | MBL 228 | CTCCTTGAAAGAGTTGGTGTG |
| SEQ ID 12 | MBL 234 | CTATGGTGCATTCGGTGATG |
| SEQ ID 13 | MBL 230 | GCGACAACTCTTGTATCAGG |
| SEQ ID 14 | MBL 233 | GACATGCTTGAGAACAAGGG |
| SEQ ID 15 | Seg3F | GAACTACCCGCCAATC |
| SEQ ID 16 | Seg2R | GAGCCCAGGCCAAAT |
| SEQ ID 17 | MBL 344 | GATCGGTCGACGAGCTCTTCTCTCTCTTAGG |
| SEQ ID 18 | MBL 220 | GTATGACGTAACAAAGCCTG |
| SEQ ID 19 | MBL 221 | GGAAATTGGCAACCCAAGGC |
| SEQ ID 20 | MBL 222 | GCTGTAAAAGTGTCCTCTGG |
| SEQ ID 21 | Seg4F | CACTGTGATGTGTTCGAAG |
| SEQ ID 22 | Seg3R | TATTTAAGCACGTTAGCG |
| SEQ ID 23 | SCJ7F | CATCTTATGTCAGATACTGA |
| SEQ ID 24 | SCJ8F | TTTTCTTTTGTTGGTGTCTC |
| SEQ ID 25 | Seg4R | CGAGCGGCCGCCACTGTGCCCTGGGGTTAGGCGC |
| SEQ ID 26 | SCJ2F | GGGAGATGAGAAGCTTCG |
| SEQ ID 27 | SCJ3F | GCCCAAACTATGAAACAAG |
| SEQ ID 28 | SCJ4F | AACGCCATTGGATCTGTAAC |
| SEQ ID 29 | SCJ6F | ATTGAACCAATCGATCCTGA |
| SEQ ID 30 | SCJ5R | TCAGGATCGATTGGTTCAAT |
| SEQ ID 31 | MBL 341 | TTCCAGGTACCTCCGGAAGGAGTTCTGGGTAG |
| SEQ ID 32 | Fr2F | AGAGCTCTCTGGCTAACGTAAAAGAAATTTGAGACAATGTCTCAAACTCTGAG |
| SEQ ID 33 | Fr4R | GGCAACTAGAAGGCACAGCCCTGGGGTTAGGCGC |

TABLE 4

| PCR conditions to generate an amplicon of FCV covering 5349 bp from the 5' end. | | | | |
|---|---|---|---|---|
| PCR mix | | PCR program | | |
| Mix components | Volumes (μL) | Step | Time | Temperature (° C.) |
| NF water | 31.0 | Initial denaturation | 30 sec | 98.0 |
| 5X PCR buffer | 10.0 | | | |
| dNTP mix (10 mM) | 1.0 | Number of cycles: 35 | | |
| F primer, SEQ ID 9 (10 μM) | 1.0 | Start of cycle | | |
| R primer, SEQ ID 10 (10 μM) | 1.0 | Denaturation | 10 sec | 98.0 |
| DMSO (final conc. 9%) | 4.5 | Annealing | 10 sec | 69.0 |
| Polymerase | 0.5 | Extension | 1 min 30 sec | 72.0 |
| Template (cDNA) | 1.0 | End of cycle | | |
| | | Final extension | 5 min | 72.0 |
| Final volume | 50.0 | Storage | indefinitely | 4.0 |

TABLE 5

| PCR conditions to generate an amplicon of FCV covering up to 2422 bp from the 3' end. | | | | |
|---|---|---|---|---|
| PCR mix | | PCR program | | |
| Mix components | Volumes (μL) | Step | Time | Temperature (° C.) |
| NF water | 31.0 | Initial denaturation | 30 sec | 98.0 |
| 5X PCR buffer | 10.0 | | | |
| dNTP mix (10 mM) | 1.0 | Number of cycles: 35 | | |
| F primer, SEQ ID 11 (10 μM) | 1.0 | Start of cycle | | |
| R primer, SEQ ID 12 (10 μM) | 1.0 | Denaturation | 10 sec | 98.0 |
| DMSO (final conc. 9%) | 4.5 | Annealing | 10 sec | 69.0 |
| Polymerase | 0.5 | Extension | 45 sec | 72.0 |
| Template (cDNA) | 1.0 | End of cycle | | |
| | | Final extension | 5 min | 72.0 |
| Final volume | 50.0 | Storage | indefinitely | 4.0 |

TABLE 6

| PCR conditions to carry out an overlap extension PCR that combines FCV amplicons to generate full length FCV DNA template. | | | | |
|---|---|---|---|---|
| PCR mix | | PCR program | | |
| Mix components | Volumes (μL) | Step | Time | Temperature (° C.) |
| NF water | 29.0 | Initial denaturation | 30 sec | 98.0 |
| 5X PCR buffer | 10.0 | | | |
| dNTP mix (10 mM) | 1.0 | Number of cycles: 35 | | |
| F primer (none) | — | Start of cycle | | |
| R primer (none) | — | Denaturation | 10 sec | 98.0 |
| DMSO (final conc. 9%) | 4.5 | Annealing | — | — |
| Polymerase | 0.5 | Extension | 3 min | 72.0 |
| Template (cDNA) | 5.0 | End of cycle | | |
| | | Final extension | 5 min | 72.0 |
| Final volume | 50.0 | Storage | indefinitely | 4.0 |

TABLE 7

PCR conditions to amplify full length FCV DNA from cDNA and add a 5' T7 promoter and 3' polyA tract.

| PCR mix | | PCR program | | |
|---|---|---|---|---|
| Mix components | Volumes (μL) | Step | Time | Temperature (° C.) |
| NF water | 34.0 | Initial denaturation | 30 sec | 98.0 |
| 5X PCR buffer | 10.0 | | | |
| dNTP mix (10 mM) | 1.0 | Number of cycles: 35 | | |
| F primer, SEQ ID 1 (10 μM) | 1.0 | Start of cycle | | |
| R primer, SEQ ID 2 (10 μM) | 1.0 | Denaturation | 10 sec | 98.0 |
| DMSO (final conc. 3%) | 1.5 | Annealing | 30 sec | 51.0 |
| Polymerase | 0.5 | Extension | 4 min | 72.0 |
| Template (cDNA) | 1.0 | End of cycle | | |
| | | Final extension | 5 min | 72.0 |
| Final volume | 50.0 | Storage | indefinitely | 4.0 |

TABLE 8

PCR conditions to amplify full length FCV DNA from overlap extension PCR template material and add a 5' T7 promoter and 3' polyA tract.

| PCR mix | | PCR program | | |
|---|---|---|---|---|
| Mix components | Volumes (μL) | Step | Time | Temperature (° C.) |
| NF water | 31.0 | Initial denaturation | 30 sec | 98.0 |
| 5X PCR buffer | 10.0 | | | |
| dNTP mix (10 mM) | 1.0 | Number of cycles: 35 | | |
| F primer, SEQ ID 3 (10 μM) | 1.0 | Start of cycle | | |
| R primer, SEQ ID 4 (10 μM) | 1.0 | Denaturation | 10 sec | 98.0 |
| DMSO (final conc. 9%) | 4.5 | Annealing | — | — |
| Polymerase | 0.5 | Extension | 3 min | 72.0 |
| Template (cDNA) | 1.0 | End of cycle | | |
| | | Final extension | 5 min | 72.0 |
| Final volume | 50.0 | Storage | indefinitely | 4.0 |

2. Preparation of Myxo-Kalem Crouch Construct

The pMCPK (processed portion of the major capsid protein of the Kalem Crouch FCV isolate) was cloned using the BamHI and XhoI sites on the p22m-GFP (a derivative of p22-GFP) plasmid MCS (multiple cloning site). See FIG. 8.

To avoid adding extra C-terminal AAs (amino acids) to pMCPK, translation from the start codon in the NcoI site of the MCS in p22-GFP was removed by introducing a point mutation (CCATGG→CCATCG, FIG. 1). Site directed mutagenesis was used to mutate the p22-GFP plasmid using the following primers:

```
p22sdmF:
                              SEQ ID NO: 63
5'-CATCGATCGATGTCGACGGATCCA-3'

p22sdmR:
                              SEQ ID NO: 64
5'-GTGCATCCGTCGACATCGATCGATG-3'
```

PCR program: 30"@98° C., 20×[10"@98° C., 10"@58.3° C., 2'@72° C.], 5'@72° C., ∞@4° C., and the Phusion polymerase (NEB, cat: M0530L).

Template p22-GFP plasmid was removed from the reaction with DpnI digestion prior to transformation into XL10 gold *E. coli* (cat: 200315). Several of the resulting *E. Coli* colonies were picked to set up miniprep cultures that were screened by digesting the extracted plasmid DNA (QiaPrep Spin Miniprep kit, cat: 27104) with NcoI. On a 1% agarose gel, a unique band corresponding to linearized plasmid indicated successful mutation (as the only remaining NcoI site in the p22m-GFP plasmid is present upstream of the GFP gene). A 342 bp fragment, in addition to linearized plasmid after digestion, indicated the presence of two NcoI sites and therefore intact p22-GFP plasmid. Sequencing was subsequently used to confirm the mutation.

Insert pMCPK was made using PCR, with primers:

(KApBamHIF:
SEQ ID NO: 65
5'TCGAGGATCCGCC*ACCATGGCC*GATGATGGATCGGTGACAACCCC-3',

KpXhoInR:
SEQ ID NO: 66
5'-TCGACTCGAGTCATAATTTAGTCATAGAACTCCTAATATTAGAGGC-3', which include a start codon in a Kozac sequence at the 5' end of pMCPK. The PCR program used was: 30"@98° C., 35×[10"@98° C., 10"@55° C., 40"@72° C.], 5'@72° C., ∞@4° C., while the template was cDNA prepared from total RNA isolated from CRFK cells infected with Kalem Crouch FCV. After confirming correct amplicon size on a 1% agarose gel, the insert DNA in the PCR reaction was purified (Qiagen PCR clean-up kit) and digested with BamHI and XhoI parallel with the p22m-GFP plasmid. Upon ligation, this procedure results in the replacement of the GFP insert and 5' and 3' RHDV repeat flanks with pMCPK (FIG. 2). The digested insert and plasmid DNA were loaded on a 1% agarose gel and bands of 1664 bp (insert) and 4031 bp (plasmid backbone) were excised and purified using the StrataPrep DNA Gel extraction kit (cat: 400766). The backbone and insert were ligated overnight at 4° C., and 2 uL of this ligation was subsequently transformed into XL10 gold *E. coli* (cat: 200315). Miniprep cultures were set up and the extracted DNA was screened by digesting with both BamHI and XhoI. The identity of the insert was confirmed using the same PCR reaction that generated the pMCPK insert (see above), and subsequently sequencing. Construct p22m-4a was chosen for use in subsequent steps.

50 uL of MR24 material diluted in 1 mL M6B8+5% FBS media was applied to a 6 cm dish with ~80% confluent RK13 cells over 5 h prior to washing away all unabsorbed MR-24 virus, supplementing with an additional 3 mL of the same media, and transfecting with ~4.5 ug of p22m-4a plasmid using Lipofectamine 3000. After ~17 h, part of the cells were harvested by gentle scraping and saved together with the media. The remaining half of cells on the plate were fixed (100% EtOH), and stained for immunofluoresence with FCV-antisera followed by with FITC-labelled anti-cat antibody, to confirm expression of pMCPK. Stained cells indicated enhanced pMCPK expression and the possible recombination between p22m-4a and MR-24 to give MR-24-Kalem Crouch, since control cells transfected with p22m-4a alone, or infected with MR-24 alone, did not stain (see FIG. 10 for a diagram of the recombinant MR24-Kalem Crouch virus).

Enrichment of MR-24-Kalem Crouch recombinant myxoma virus was carried out through successive rounds of titration, immunofluoresence detection of expressed pMCPK, and dilution of enriched samples. Briefly, a series of 96-well tissue culture dishes seeded with RK-13 cells were infected with virus from the infection/transfection at a range of dilutions. After 3 days, all the 96-well dishes were frozen and retained as the first round stocks. A second series of RK-13 seeded 96-well dishes were then infected with material from the first round stocks (5-10 μl from each well). After 2-3 days these duplicate dishes were fixed with ice cold methanol and stained first with a cat anti-FCV polyclonal antiserum and then a goat anti-feline IgG FITC labelled second antibody. Wells containing fluorescing foci of infection were identified and the corresponding wells on the first round stock dishes taken, then diluted and used to infect a second series of 96-well dishes, which became the second round stocks. This procedure was repeated until virus stocks contained majority recombinant virus. The final purification was achieved by three rounds of single focus isolation. The three best staining clones (i.e. B8, A9, and A10) were expanded, and clone A9 was used to in further experiments to determine clonal purity (i.e. lack of wild-type MR24 growing in the background) and insert (i.e. pMCPK) sequence stability. MR24-Kalem Crouch was passed 5 times in RK13 cells by inoculating each time at 0.001 MOI.

To determine the stability of the pMCPK insert, MR24-Kalem Crouch DNA from pass 1 and MR24-Kalem Crouch DNA from pass 5 were compared. No mutations were detected in either p22m-4a vs MR24-Kalem Crouch-pass1, or MR24-Kalem Crouch-pass1 vs MR-24-Kalem Crouch-pass5, indicating that the pMCPK in p22m-4a recombined successfully with MR24 and remained stable over 5 passages of the virus.

Taken together, these experiments show that the processed major capsid protein of FCV Kalem Crouch (pMCPK) has been inserted into, and is expressed from, the MGF site of the MR24-Kalem Crouch clone A9.

Results

1. Isolation and Growth of FCV Kalem Crouch

Feline Calicivirus (FCV) strain Kalem Crouch was isolated from a swab taken during an FCV outbreak in Jersey in December 2010. The swab originated from a neutered male, 2 years 6 months, named Kalem Crouch and was collected by New Era Veterinary Surgery, St Saviour, Jersey. The swab was vortexed briefly and the virus suspension inoculated onto confluent CrFK cells and incubated at 37° C. with 5% $CO_2$ until CPE specific to FCV was observed. The infected flask was freeze thawed to lyse cells, clarified to remove cellular debris and stored at −70° C. The titer of the virus was $10^{6.91}$ $TCID_{50}$/ml.

The nucleotide sequence of the isolate was determined. The sequence is annotated in SEQ ID NO: 60.

The amino acid sequence of the capsid protein was aligned with other FCV sequences available in the public domain. The sequence alignment is annotated in FIGS. 5 and 7.

2. Generating Recombinant FCV Virus

2.1. Preparation of FCV Amplicons

FCV F9 or Kalem Crouch cDNA, made as described in methods section 5, was used as template in PCR reactions with the Phusion polymerase (NEB, Ipswich, Mass.), oligonucleotide primer pair FKP1F (SEQ ID NO: 9) and FKP1R (SEQ ID NO: 10), and the conditions described in Table 4 to generate an amplicon covering 5349 bp from the 5' end of FCV genome. Similarly, the oligonucleotide primer pair FKP2F (SEQ ID NO: 11) and FKP2R (SEQ ID NO: 12) and the PCR conditions described in Table 5 were used to generate amplicons covering 2422 bp from the 3' end of FCV F9 and 2416 bp from the 3' end of FCV Kalem Crouch. These amplicons and 5 μL of GeneRuler 1 kb Plus DNA ladder (Thermo Scientific, Waltham, Mass.) were resolved by carrying out electrophoresis in 1×TBE buffer (Sigma-Aldrich, St. Louis, Mo.) at 120V over 1 h. Bands of the expected size are shown in FIG. 1.

2.2. Assembly of FCV Amplicons Using Overlap Extension PCR

The FCV amplicons generated in results section 2 were purified using the QIAquick® PCR Purification Kit (Qiagen, Hilden, Germany). These amplicons were used to make hybrid viruses: Hybrid virus FK comprises the Kalem Crouch capsid in the F9 background and hybrid virus KF comprises the F9 capsid in the Kalem Crouch background.

To make FCV FK and KF template DNA, equimolar mixtures containing between 0.1 and 0.5 pmol of each amplicon were made with either FCV F9 5' end and FCV Kalem Crouch 3' end amplicons, or FCV Kalem Crouch 5' end and FCV F9 3' end amplicons. These mixtures were used as templates in overlap extension PCR reactions with conditions described in Table 6. The expected sizes of the assembled FK and KF DNA amplicons were 7685 and 7702 bp respectively. The assembled DNA in these samples and 5 μL of GeneRuler 1 kb Plus DNA ladder (Thermo Scientific, Waltham, Mass.) were resolved by carrying out electrophoresis in 1×TBE buffer (Sigma-Aldrich, St. Louis, Mo.) at 120V over 1 h. The resulting assembled DNA of F9, Kalem Crouch, FK, and KF is shown in FIG. 2.

2.3. Generation of Infectious FCV Virus

Figure 3:
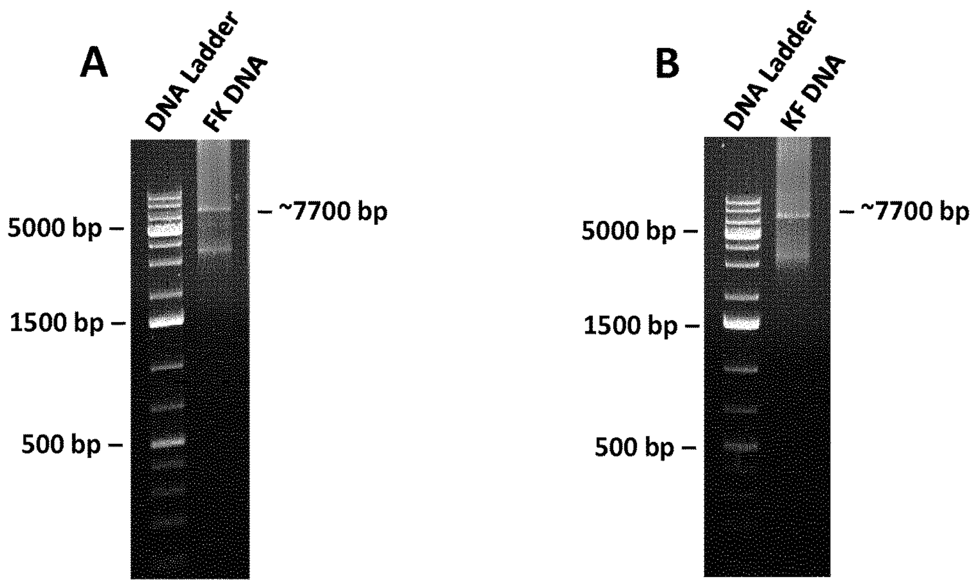

Infectious FCV FK or KF DNA was made using the Phusion polymerase (NEB, Ipswich, Mass.) and the oligonucleotide primer pair FCVT7f (SEQ ID NO: 3) and FCV-pAr (SEQ ID NO: 4) with the PCR conditions described in Table 8. The expected sizes of infectious FCV FK and KF DNA are 7728 and 7737 bp respectively. The infectious FCV DNA in these samples and 5 μL of GeneRuler 1 kb Plus DNA ladder (Thermo Scientific, Waltham, Mass.) were resolved by carrying out electrophoresis in 1×TBE buffer (Sigma-Aldrich, St. Louis, Mo.) at 120V over 1 h. The full length infectious DNA of FK and KF is shown in FIG. 3 parts A and B respectively.

2.4. Recovery of Infectious FCV Virus

Infectious FCV FK and KF DNA was purified from full-length the full length PCR reactions using the QIAquick® PCR Purification Kit (Qiagen, Hilden, Germany), and transfected onto 50-90% confluent BsRT7 cells growing on a 24-well plate using the Invitrogen® Lipofectamine® 3000 Reagent (Carlsbad, Calif.) as described in methods section 13. Transfected BsRT7 cells were incubated with transfection complexes under normal growth conditions for 24-72 h prior to lysis by freeze-thawing. BsRT7 lysate from each well was then applied to a well growing CrFK cells to confluency between 50 and 100%. CrFK cells grown in the presence of BsRT7 cell lysate were incubated under normal growth conditions, as described in methods section 1. The presence of a virus was typically detected by the formation of plaques in the monolayer of CrFK cells, similar to those shown in FIG. 4.

2.5. Sequence of FCV FK and KF Viruses

The recombinant FCV viruses were sequenced.

These sequences have been compared with the sequences of FCV F9 and Kalem Crouch in FIG. 6. The recombinant FK virus is denoted SEQ ID NO: 61 and comprises the Kalem Crouch capsid. The recombinant KF virus is denoted SEQ ID NO: 62 and comprises the F9 capsid.

2.6 Efficacy of Myxo-Kalem Crouch Construct in Cats

Experimental Design

Fifteen domestic short hair cats between 8-11 weeks of age were divided into two groups. A group of 10 cats vaccinated subcutaneously, twice, three weeks apart with recombinant Myxo-Kalem Crouch construct described above (pass 5) ($10^{6.23}$ $TCID_{50}$ per dose) and a group of 5 control cats. Four weeks post second vaccination, cats were swabbed and two of the control unvaccinated cats were challenged intra-nasally with virulent FCV strain Kalem Crouch ($10^{4.0}$ $TCID_{50}$ per cat) and mixed with the rest of the cats for contact challenge. All cats were swabbed daily from day 1 post challenge to day 17 post challenge. Clinical observations, including body weights and temperatures were recorded. The clinical findings were scored as below, see table 8. (An anti-pyretic was administered to alleviate the pyrexia and suffering. In a previous experiment, it was proved that administration of an antipyretic had no effect on virus excretion)

TABLE 8

Overview of scoring of clinical sign

| Clinical sign | Score |
|---|---|
| Mild malaise (MA+) | 1 |
| Pronounced malaise (Ma++) | 2 |
| Ulcers present (regardless of number or size) | 1 |
| Lameness/limping (regardless of number of affected limbs) | 2 |
| Virus shedding | 1 |
| Pyrexia (temperature above ≥39.5° C.) | 1 |
| Antipyretic administered to alleviate pyrexia and suffer (administered when temperature is above 40° C.) | 10 (per administration) |
| Weight loss compared to previous day | 1 |

Results

Cats were devoid of antibodies prior to vaccination (Day-1). A strong sero-conversion was not observed in cats post vaccination (Day 48). A strong sero-conversion was observed in cats post challenge (Day 66).

TABLE 9

Titer of antibodies

| | | F9-specific virus neutralising antibodies | | | Kalem Crouch-specific virus neutralising antibodies | | |
|---|---|---|---|---|---|---|---|
| Cat Id | Group | Day -1 | Day 48 | Day 66 | Day -1 | Day 48 | Day 66 |
| 6346 | 1 | ≤4 | ≤4 | 170 | ≤4 | ≤4 | 256 |
| 7229 | 1 | ≤4 | ≤4 | 102 | ≤4 | ≤4 | 386 |
| 4297 | 1 | ≤4 | 13 | 323 | ≤4 | ≤4 | 406 |
| 5530 | 1 | ≤4 | 16 | 412 | ≤4 | ≤4 | 4871 |
| 8817 | 1 | ≤5 | ≤6 | 1176 | ≤4 | ≤4 | 256 |
| 9449 | 1 | ≤4 | ≤4 | 61 | ≤4 | ≤4 | 406 |
| 6644 | 1 | ≤4 | ≤4 | 82 | ≤4 | ≤4 | 215 |
| 0498 | 1 | ≤5 | ≤4 | 128 | ≤4 | ≤4 | 724 |
| 0566 | 1 | ≤4 | ≤4 | 395 | ≤4 | ≤4 | 304 |
| 6622 | 1 | ≤4 | ≤4 | 64 | ≤4 | ≤4 | 64 |
| 2987 | 2 | ≤4 | ≤4 | 62 | ≤4 | ≤4 | 4096 |
| 6446 | 2 | ≤4 | ≤4 | 181 | ≤4 | ≤4 | 329 |
| 3854 | 2 | ≤4 | ≤4 | 1080 | ≤4 | ≤4 | 5270 |
| 8741 | 2 | ≤5 | ≤4 | 304 | ≤4 | ≤4 | 724 |
| 5139 | 2 | ≤5 | ≤4 | 512 | ≤4 | ≤4 | 1337 |

Virus could not be isolated from the cats at the beginning of the experiment or on the day prior to challenge. Virus could be isolated from all cats of groups 1 and 2, clinical signs associated with FCV were observed in cats belonging to both groups indicating a substantial challenge.

TABLE 10

Clinical scores

| Cat Identity | Group/ Treatment | Pyrexia score | Anti-pyretic score | Clinical score | Body weight | Days virus excreted | Total |
|---|---|---|---|---|---|---|---|
| 9449 | 1 | 1 | 0 | 16 | 6 | 8 | 31 |
| 8817 | Vaccinated | 0 | 0 | 10 | 6 | 15 | 31 |
| 0498 | | 6 | 10 | 17 | 4 | 13 | 50 |
| 4297 | | 0 | 0 | 11 | 6 | 14 | 31 |
| 6346 | | 0 | 0 | 10 | 5 | 13 | 28 |
| 0566 | | 3 | 0 | 11 | 6 | 14 | 34 |
| 6644 | | 1 | 0 | 12 | 4 | 14 | 31 |
| 5530 | | 10 | 20 | 13 | 6 | 12 | 61 |

TABLE 10-continued

| Clinical scores | | | | | | | |
|---|---|---|---|---|---|---|---|
| Cat Identity | Group/ Treatment | Pyrexia score | Anti-pyretic score | Clinical score | Body weight | Days virus excreted | Total |
| 6622 | | 1 | 0 | 12 | 2 | 16 | 31 |
| 7229 | | 0 | 0 | 9 | 4 | 10 | 23 |
| 2987 | 2 | 8 | 10 | 10 | 6 | 13 | 47 |
| 6446 | Challenge | 5 | 10 | 16 | 4 | 14 | 49 |
| 3854 | control | 11 | 20 | 19 | 7 | 10 | 67 |
| 5139 | | 4 | 10 | 14 | 3 | 10 | 41 |
| 8741 | | 7 | 0 | 14 | 5 | 16 | 42 |

TABLE 11

| clinical signs per group: | | | | | | |
|---|---|---|---|---|---|---|
| | Pyrexia score | | Antipyretic score | | Clinical score | |
| Group | Mean | Median | Mean | Median | Mean | Median |
| 1 | 2.20 | 1.00 | 3.00 | 0.00 | 12.10 | 11.50 |
| 2 | 7.0 | 7.0 | 10.00 | 10.00 | 14.60 | 14.00 |
| | Body weight | | Days virus excreted | | Total score | |
| | Mean | Median | Mean | Median | Mean | Median |
| 1 | 4.90 | 5.50 | 12.90 | 13.50 | 35.10 | 31.00 |
| 2 | 5.00 | 5.00 | 12.6 | 13.0 | 49.20 | 47.00 |

A Kruskal-Wallis non parametric test on the data showed statistically significant difference between the vaccinated cats and control cats for total score (P=0.037) and pyrexia score (P=0.020) indicating that the Myxo-Kalem Crouch construct was able to induce immunity against FCV challenge infection (reduction in the clinical scores in cats post challenge).

Experimental Design

2.7 Study to Raise Hyperimmune Serum to FK and KF Hybrid Viruses of FCV

The study comprised six domestic short haired cats between 229 and 432 days of age. These were split into two groups of 3 cats with a relatively even split of toms between groups. Each group was housed separately. After acclimatization, cats belonging to group 1 were inoculated subcutaneously with $10^{4.6}$ $TCID_{50}$/dose of FCV strain FK. Cats belonging to group 2 were inoculated subcutaneously with $10^{4.6}$ $TCID_{50}$/dose of FCV strain KF.

All cats then received a second dose of the same virus at $10^5$ $TCID_{50}$/dose intranasally two weeks later (day 14). Serum was collected three weeks post second inoculation.

Serum was heat inactivated and a virus neutralisation test carried out. Virus neutralisation was assessed by a reduction of virus-induced cytopathic effect (CPE) on CrFK cells. Five-fold replicates of 32-316 $TCID_{50}$ of virus were mixed with an equal volume of serial dilutions of sera (commencing at 1:4). Virus/sera mixtures were then incubated for at least 60 min at 37° C. 100 μl of the virus-serum mixtures were then added to 96-well tissue culture dishes seeded with CrFK cells in 100 μl growth medium. Incubation was continued for 5 days. The VN titer is expressed as the inverse of the highest serum dilution at which virus-induced CPE was completely absent.

Results

TABLE 12

| VN titers post first inoculation (s.c.) | | | | | |
|---|---|---|---|---|---|
| Vaccine | Cat number | Anti F9 | Anti Kalem Crouch | Anti KF | Anti FK |
| FK | 8086 | ≥39 | >64 | NT | >64 |
| | 7978 | 16 | >64 | NT | >64 |
| | 5466 | ≤6 | ≤6 | NT | ≤6 |
| KF | 2274 | 23 | ≤6 | >64 | NT |
| | 9915 | 46 | ≤6 | >64 | NT |
| | 8394 | 23 | ≤6 | >64 | NT |

NT: Not Tested

TABLE 13

| VN titers post second inoculation (i.n.) | | | | | |
|---|---|---|---|---|---|
| vaccine | Cat number | Anti F9 | Anti Kalem Crouch | Anti KF | Anti FK |
| FK | 8086 | 56 | 724 | 2896 | 16394 |
| | 7978 | 21 | 215 | 334 | 2580 |
| | 5466 | 64 | 645 | 1625 | 19484 |
| KF | 2274 | 54 | ≤6 | 1505 | ≤5 |
| | 9915 | 1024 | ≤6 | 50935 | 73 |
| | 8394 | 512 | ≤6 | 50935 | 40 |

The data shows that recombinant viruses FK and KF are immunogenic in cats. The antibodies developed in the cats were functional (neutralizing). The cross reactivity of the antibodies showed a hierarchy similar to the hierarchy observed between FCV strain F9 and FCV strain Kalem Crouch such that inoculation of cats with hybrid strain KF (F9 capsid) induced virus neutralising antibodies against strains F9 but not against strain Kalem Crouch whilst inoculation with hybrid strain FK (Kalem Crouch capsid) resulted in the induction of virus neutralising antibodies against both strains F9 and Kalem Crouch.

2.8 Neutralisation Index

Hyper-immune sera raised in cats to strains FCV F9 and Kalem Crouch were used to determine the neutralisation index of the recombinant FCV strains FK and KF. The data is shown in table 7.

It becomes clear from the table that FCV strain FK is indeed neutralized strongly by anti-FCV Kalem Crouch hyperimmune serum whereas FCV strain KF is indeed neutralized strongly by anti-FCV F9 hyperimmune serum.

TABLE 14

| Neutralising Index of the FCV F9 and Kalem Crouch anti-sera to recombinant FCV FK and KF. | | | |
|---|---|---|---|
| FCV sample | Neutralising ability of anti-FCV F9 hyper-immune serum | Neutralising ability of anti-FCV Kalem Crouch hyper-immune serum | Virus titre ($log_{10}$/ml) |
| FCV FK hybrid | 0.34 | 6.67 | 6.67 |
| FCV KF hybrid | 3.33 | 2.67 | 7 |
| FCV F9 X + 2 | 3.17 | 1.83 | 7.5 |
| FCV Kalem Crouch #4063 | 1 | 5.5 | 5.5 |

Table 14 and the data obtained from sera generated from FK and KF inoculated cats (Table 13) demonstrate that there is a one way hierarchy to virus neutralisation. F9 and KF (F9 capsid) antisera do not neutralise Kalem Crouch or FK (Kalem Crouch capsid) viruses efficiently while the serum from cats vaccinated with Kalem Crouch and FK (Calem Crouch capsid) neutralise self and also neutralise F9 and KF (F9 capsid) viruses significantly.

The invention claimed is:

1. A feline calicivirus (FCV) capsid protein comprising a sequence identity of at least 90% with the amino acid sequence of SEQ ID NO: 34.

2. A feline calicivirus (FCV) capsid protein comprising at least one of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636, wherein the numbering is according to SEQ ID NO: 34.

3. A live attenuated FCV comprising a capsid protein comprising a sequence identity of at least 90% with the amino acid sequence of SEQ ID NO: 34.

4. A live attenuated feline calicivirus (FCV) comprising a capsid protein wherein the capsid protein comprises at least one of the following amino acids K89, M90, M100, I317, L390, A391, V392, Q396, S397, K398, N404, T426, T431, S438, S437, D440, E445, K447, L448, E451, N452, G484, G489, I491, N516, S517, E518, I524, S545, S634, F635, P636.

5. A DNA fragment wherein said DNA fragment comprises a region encoding said capsid protein of claim 1.

6. A DNA fragment of claim 5, wherein said region encoding said capsid protein is placed under the control of a suitable promoter.

7. A live attenuated recombinant carrier virus (LARCV), wherein said LARCV comprises a region encoding a feline calicivirus (FCV) capsid protein of claim 1, under the control of a suitable promoter.

8. A live attenuated recombinant carrier virus according to claim 7, wherein said LARCV is a myxomavirus or a Feline Herpesvirus.

9. A method of protecting felines against FCV comprising administering a live attenuated recombinant carrier virus of claim 7.

10. A live attenuated hybrid FCV, wherein said FCV comprises an open reading frame 2 (ORF2) encoding a capsid protein comprising a sequence identity of at least 90% with the amino acid sequence of SEQ ID NO: 34, or said DNA fragment of claim 5, and comprises an open reading frame 1 (ORF1) from an attenuated FCV.

11. A live attenuated hybrid FCV of claim 10, wherein said FCV comprises an ORF1 from FCV strain F9.

12. A method of protecting felines against FCV comprising administering a live attenuated hybrid FCV of claim 10.

13. A cell culture comprising a live attenuated FCV of claim 3.

14. A cell culture comprising a LARCV of claim 7.

15. A cell culture comprising a live attenuated hybrid FCV of claim 10.

16. A vaccine for the protection of felines against FCV, wherein said vaccine comprises a live attenuated FCV comprising a capsid protein comprising a sequence identity of at least 90% with the amino acid sequence of SEQ ID NO: 34, or a live recombinant carrier virus of claim (LARCV), wherein said LARCV comprises a region encoding a feline calicivirus (FCV) capsid protein comprising a sequence identity of at least 90% with the amino acid sequence of SEQ ID NO: 34, under the control of a suitable promoter, or a live attenuated hybrid FCV of claim 10, and a pharmaceutically acceptable carrier.

17. A vaccine of claim 16, wherein said vaccine comprises at least one other feline-pathogenic microorganism or feline-pathogenic virus and/or at least one other immunogenic component and/or genetic material encoding said other immunogenic component of said feline-pathogenic microorganism or feline-pathogenic virus.

18. A vaccine of claim 17, wherein said other feline-pathogenic microorganism or feline-pathogenic virus is selected from the group consisting of feline panleucopenia virus, *Chlamydia psittaci, Bordetella bronchiseptica*, feline parvovirus, rabies virus and feline herpes virus.

19. A method for obtaining a live attenuated hybrid FCV of claim 10 comprising:

a. preparation of a first FCV amplicon comprising the full ORF1 region and an adjacent 5'-part of the ORF2 region of an attenuated FCV, b. preparation of a second FCV amplicon comprising a 3'-part of the ORF1 region and the full adjacent ORF2//ORF3 region wherein the ORF2 is an ORF2 encoding an FCV capsid protein comprising a sequence identity of at least 90% with the amino acid sequence of SEQ ID NO: 34, c. assembly of the first and second amplicon using overlap extension, d. generation of infectious FCV, e. infection of susceptible cells with the infectious FCV, and f. recovery of infectious progeny FCV.

* * * * *